US012709760B2

(12) United States Patent
Pattnaik et al.

(10) Patent No.: US 12,709,760 B2

(45) Date of Patent: Aug. 18, 2026

(54) KIR 7.1 GENE THERAPY VECTORS AND METHODS OF USING THE SAME

(71) Applicant: WISCONSIN ALUMNI RESEARCH FOUNDATION, Madison, WI (US)

(72) Inventors: Bikash Pattnaik, Middleton, WI (US); Pawan Shahi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1146 days.

(21) Appl. No.: 17/284,408

(22) PCT Filed: Oct. 10, 2019

(86) PCT No.: PCT/US2019/055635

§ 371 (c)(1),
(2) Date: Apr. 9, 2021

(87) PCT Pub. No.: WO2020/077091

PCT Pub. Date: Apr. 16, 2020

(65) Prior Publication Data

US 2021/0348196 A1 Nov. 11, 2021

Related U.S. Application Data

(60) Provisional application No. 62/743,623, filed on Oct. 10, 2018.

(51) Int. Cl.

| | |
|---|---|
| ***C12N 15/86*** | (2006.01) |
| ***A61K 9/00*** | (2006.01) |
| ***A61K 48/00*** | (2006.01) |
| ***C07K 14/705*** | (2006.01) |

(52) U.S. Cl.

CPC ............ *C12N 15/86* (2013.01); *A61K 9/0048* (2013.01); *C07K 14/705* (2013.01); *A61K 48/00* (2013.01); *C12N 2740/15043* (2013.01); *C12N 2740/15071* (2013.01); *C12N 2750/14143* (2013.01); *C12N 2750/14171* (2013.01)

(58) Field of Classification Search

None

See application file for complete search history.

(56) References Cited

U.S. PATENT DOCUMENTS

| | | | |
|---|---|---|---|
| 5,670,488 | A | 9/1997 | Gregory |
| 5,824,544 | A | 10/1998 | Armentano |
| 5,851,826 | A | 12/1998 | Fraefel |
| 5,871,747 | A | 2/1999 | Gengoux-Sedlik |
| 5,879,934 | A | 3/1999 | DeLuca |
| 5,932,210 | A | 8/1999 | Gregory |
| 5,981,719 | A | 11/1999 | Woiszwillo |
| 6,022,564 | A | 2/2000 | Takechi |
| 6,090,925 | A | 7/2000 | Woiszwillo |
| 6,210,707 | B1 | 4/2001 | Papahadjopoulos |
| 6,264,987 | B1 | 7/2001 | Wright |
| 6,309,569 | B1 | 10/2001 | Farrar |
| 6,379,704 | B2 | 4/2002 | Wright |
| 6,528,087 | B2 | 3/2003 | Papahadjopoulos |
| 6,534,092 | B2 | 3/2003 | Wright |
| 6,565,777 | B2 | 5/2003 | Farrar |
| 6,884,435 | B1 | 4/2005 | O'Hagan |
| 6,913,767 | B1 | 7/2005 | Cleland |
| 7,396,664 | B2 | 7/2008 | Daly |
| 8,252,324 | B2 | 8/2012 | Petrenko |
| 2003/0036648 | A1 | 2/2003 | Miller |
| 2006/0051331 | A1 | 3/2006 | Mallet et al. |
| 2006/0105364 | A1 | 5/2006 | Petrukhin et al. |
| 2007/0081972 | A1 | 4/2007 | Sandler |
| 2008/0019946 | A1 | 1/2008 | Nenoi et al. |
| 2010/0273256 | A1 | 10/2010 | Miller et al. |
| 2013/0035475 | A1 | 2/2013 | MacKinnon |
| 2014/0066388 | A1 | 3/2014 | Anderson |
| 2014/0357590 | A1 | 12/2014 | Saasov |
| 2017/0096683 | A1 * | 4/2017 | Scaria ..................... A61P 43/00 |
| 2018/0057795 | A1 | 3/2018 | Childs |
| 2019/0255192 | A1 | 8/2019 | Kirn et al. |
| 2019/0255193 | A1 | 8/2019 | Groendahl et al. |

FOREIGN PATENT DOCUMENTS

| | | | |
|---|---|---|---|
| EP | 0922763 | A1 | 6/1999 |
| WO | 2012054425 | A2 | 4/2012 |
| WO | 2012115806 | A1 | 8/2012 |
| WO | 2017197355 | A2 | 11/2017 |
| WO | 2020077091 | A1 | 4/2020 |

OTHER PUBLICATIONS

ABSSBlast (NCBI Blast Results; https://blast.ncbi.nlm.nih.gov/; accessed Mar. 22, 2024). (Year: 2024).*

(Continued)

*Primary Examiner* — Maria G Leavitt

*Assistant Examiner* — Alexandra F Connors

(74) *Attorney, Agent, or Firm* — Quarles & Brady LLP

(57) ABSTRACT

The present invention is directed to gene therapy constructs and pharmaceutical compositions for the expression of Kir7.1. The gene therapy constructs include a vector comprising a promoter operably connected to a polynucleotide encoding a Kir7.1 polypeptide. Methods of treating a subject having a condition associated with insufficient expression or function of a Kir7.1 polypeptide are also provided.

16 Claims, 40 Drawing Sheets

(38 of 40 Drawing Sheet(s) Filed in Color)

Specification includes a Sequence Listing.

(56) References Cited

OTHER PUBLICATIONS

NCBISeq1 (NCBI, GenBank AAH37290.1; accessed Mar. 22, 2024) (Year: 2024).*
Wang et al. J. Cell. Mol. Med. Vol 21, No. 11, 2017 pp. 3044-3054 (Year: 2017).*
NCBI Ref (inward rectifier potassium channel 13 isoform 1 [*Homo sapiens*]—Protein—NCBI; NP_00233.2.; Date Accessed Sep. 10, 2024) (Year: 2024).*
Shahi et al. Investigative Ophthalmology & Visual Science Jun. 2017, vol. 58, 4091 (Year: 2017).*
NCBI Ref MG (MG840310.1; submitted Jan. 24, 2018) (Year: 2018).*
Balaggan et al. Gene Therapy (2012) 19, 182-188 (Year: 2012).*
www.calculator.net/exponent-calculator.html; last visited Sep. 11, 2024 (SEQ ID 1 variants) (Year: 2024).*
www.calculator.net/exponent-calculator.html; last visited Sep. 11, 2024 (SEQ ID 3 variants) (Year: 2024).*
www.calculator.net/exponent-calculator.html; last visited Sep. 11, 2024 (SEQ ID 4 variants) (Year: 2024).*
www.calculator.net/exponent-calculator.html; last visited Sep. 11, 2024 (SEQ ID 5 variants) (Year: 2024).*
www.calculator.net/exponent-calculator.html; last visited Sep. 11, 2024 (SEQ ID 6 variants) (Year: 2024).*
Seitz et al. Retinal Gene Transfer and Biodistribution Profile of Subretinal Versus Intravitreal Delivery of AAV8 in Nonhuman Primates, Invest Ophthalmol Vis Sci, Nov. 1, 2017;58(13):5792-5801 (Year: 2017).*
Lu et al. AAV dose-dependent transduction efficiency in retinal ganglion cells and functional efficacy of optogenetic vision restoration, Gene Ther 31, 572-579 (2024) (Year: 2024).*
Varin et al. Risk Mitigation of Immunogenicity: A Key to Personalized Retinal Gene Therapy, Int J Mol Sci. Nov. 26, 2021;22(23): 12818 (Year: 2021).*
Ma et al, Microphthalmia-associated transcription factor acts through PEDF to regulate RPE cell migration, Experimental Cell Research, vol. 318, Issue 3, Feb. 1, 2012, pp. 251-261 (Year: 2012).*
Esumi et al. Genes: Structure and Regulation, vol. 279, Issue 18, p. 19064-19073, Apr. 2004), (Year: 2004).*
Ghazi et al, Hum Genet (2016) 135:327â343 (Year: 2016).*
International Search Report and Written Opinion issued in corresponding PCT Application No. PCT/US2021/022382, mailed Jul. 1, 2021.
Cornejo et al., Tissue Distribution of Kir7.1 Inwardly Rectifying K+ Channel Probed in a Knock-in Mouse Expressing a Haemagglutinin-Tagged Protein, Frontiers in Physiology, vol. 9, Article 428, (Apr. 2018).
Partiseti et al., Cloning and characterization of a novel human inwardkly rectifying potassium channel predominantely expressed in small intestine, Federation of European Biochemical Societies, Letters 434 (1998), pp. 171-176.
Bennett, J. et al. Safety and durability of effect of contralateral-eye administration of AAV2 gene therapy in patients with childhood-onset blindness caused by RPE65 mutations: a follow-on phase 1 trial. Lancet 388, 661-72 (2016).
Boye, S. E., et al. "Functional and behavioral restoration of vision by gene therapy in the guanylate cyclase-1 (GC1) knockout mouse." PLoS One 5.6 (2010): e11306.
Boye, S. L., et al. "AAV-mediated gene therapy in the guanylate cyclase (RetGC1/RetGC2) double knockout mouse model of Leber congenital amaurosis." Human gene therapy 24.2 (2013): 189-202.
Brendel, C. et al. Readthrough of nonsense mutations in Rett syndrome: evaluation of novel aminoglycosides and generation of a new mouse model. J Mol Med (Berl) 89, 389-98 (2011).
Cereso, N., et al. "Proof of concept for AAV2/5-mediated gene therapy in iPSC-derived retinal pigment epithelium of a choroideremia patient." Molecular Therapy-Methods & Clinical Development 1 (2014): 14011.
Dalkara, D., et al. Let There Be Light: Gene and Cell Therapy for Blindness. Hum Gene Ther 27, 134-47 (2016).
Dalkara, D., et al. "In vivo-directed evolution of a new adeno-associated virus for therapeutic outer retinal gene delivery from the vitreous." Science translational medicine 5.189 (2013): 189ra76-189ra76.
Derst, C. et al. Partial gene structure and assignment to chromosome 2q37 of the human inwardly rectifying K+ channel (Kir7.1) gene (KCNJ13). Genomics 54, 560-3 (1998).
Ding, Y., et al. "The kidney androgen-regulated protein promoter confers renal proximal tubule cell-specific and highly androgen-responsive expression on the human angiotensinogen gene in transgenic mice." Journal of Biological Chemistry 272.44 (1997): 28142-28148.
Dull, T., et al. "A third-generation lentivirus vector with a conditional packaging system." Journal of virology 72.11 (1998): 8463-8471.
Duong, T. T., et al. "Comparative AAV-eGFP Transgene Expression Using Vector Serotypes 1-9, 7m8, and 8b in Human Pluripotent Stem Cells, RPEs, and Human and Rat Cortical Neurons." Stem cells international 2019 (2019): 7281912.
Ghamari-Langroudi, M. et al. G-protein independent coupling of MC4R to Kir7.1 in hypothalamic neurons. Nature (2015).
Goldmann, T. et al. A comparative evaluation of NB30, NB54 and PTC124 in translational read-through efficacy for treatment of an USH1C nonsense mutation. EMBO Mol Med 4, 1186-99 (2012).
Hargreaves, B. Astellas prioritises ophthalmology with gene therapy acquisition. Article from BioPharma-Reporter.com. Published Aug. 21, 2018. Available online at https://www.biopharma-reporter.com/Article/2018/08/21/Astellas-prioritises-ophthalmology-with-gene-therapy-acquisition.
Hejtmancik, J.F. et al. Mutations in KCNJ13 cause autosomal dominant snowflake vitreoretinal degeneration. Am J Hum Genet 82, 174-180 (2008).
International Searching Authority. International Search Report and Written Opinion for application PCT/US2019/055635. Mailed on Feb. 18, 2020. 16 pages.
Jacobson, S. G., et al. "Safety of recombinant adeno-associated virus type 2-RPE65 vector delivered by ocular subretinal injection." Molecular Therapy 13.6 (2006): 1074-1084.
Khan, A.O., et al. A distinct vitreo-retinal dystrophy with early-onset cataract from recessive KCNJ13 mutations. Ophthalmic Genet 36, 79-84 (2015).
Krapivinsky, G. et al. A novel inward rectifier K+ channel with unique pore properties. Neuron 20, 995-1005 (1998).
Kumar, M. et al. Focus on Kir7.1: physiology and channelopathy. Channels (Austin), 2014. 8(6): p. 488-95.
Lisowski, L. et al. "Adeno-associated virus serotypes for gene therapeutics." Current opinion in pharmacology 24 (2015): 59-67.
McCloskey, C. et al. The inwardly rectifying K+ channel KIR7.1 controls uterine excitability throughout pregnancy. EMBO Mol Med 6, 1161-74 (2014).
Nudelman, I. et al. Repairing faulty genes by aminoglycosides: development of new derivatives of geneticin (G418) with enhanced suppression of diseases-causing nonsense mutations. Bioorg Med Chem 18, 3735-46 (2010).
Pattnaik, B.R. et al. A Novel KCNJ13 Nonsense Mutation and Loss of Kir7.1 Channel Function Causes Leber Congenital Amaurosis (LCA16). Hum Mutat 36, 720-7 (2015).
Pattnaik, B.R. et al. Snowflake vitreoretinal degeneration (SVD) mutation R162W provides new insights into Kir7.1 ion channel structure and function. PLoS One, 2013. 8(8): p. e71744.
Perez-Roustit, S. et al. Leber Congenital Amaurosis with Large Retinal Pigment Clumps Caused by Compound Heterozygous Mutations in Konj13. Retin Cases Brief Rep 11, 221-226 (2017).
Ramsden, C.M. et al. Rescue of the MERTK phagocytic defect in a human iPSC disease model using translational read-through inducing drugs. Sci Rep 7, 51 (2017).
Scholl, HPN, et al. "Emerging therapies for inherited retinal degeneration." Science translational medicine 8.368 (2016): 368rv6-368rv6.
Sergouniotis, P.I. et al. Recessive mutations in KCNJ13, encoding an inwardly rectifying potassium channel subunit, cause leber congenital amaurosis. Am J Hum Genet 89, 183-90 (2011).

(56) References Cited

OTHER PUBLICATIONS

Shahi, P. K., et al. "Gene augmentation and readthrough rescue channelopathy in an iPSC-RPE model of congenital blindness." The American Journal of Human Genetics 104.2 (2019): 310-318.
Shahi, P. K., et al. "Rescue of Kir7.1 function by gene augmentation in LCA16 patient derived iPSC-RPE cells." Investigative Ophthalmology & Visual Science 59.9 (Jul. 2018): 1196-1196.
Shahi, P. K., et al. Abnormal Electroretinogram after Kir7.1 Channel Suppression Suggests Role in Retinal Electrophysiology. Sci Rep 7, 10651 (2017).
Shimura, M. et al. Expression and permeation properties of the K(+) channel Kir7.1 in the retinal pigment epithelium. J Physiol 531, 329-46 (2001).
Singh, R. et al. iPS cell modeling of Best disease: insights into the pathophysiology of an inherited macular degeneration. Hum Mol Genet 22, 593-607 (2013).
Snowball, A. et al. "Changing channels in pain and epilepsy: Exploiting ion channel gene therapy for disorders of neuronal hyperexcitability." FEBS letters 589.14 (2015): 1620-1634.
White, M., et al. A Guide to Approaching Regulatory Considerations for Lentiviral-Mediated Gene Therapies. Hum Gene Ther Methods 28, 163-176 (2017).
Yanez-Munoz, R.J. et al. Effective gene therapy with nonintegrating lentiviral vectors. Nat Med 12, 348-53 (2006).
Yang, D., et al. Expression and localization of the inwardly rectifying potassium channel Kir7.1 in native bovine retinal pigment epithelium. Invest Ophthalmol Vis Sci 44, 3178-85 (2003).
Ambati et al. Transscleral drug delivery to the retina and choroid. Progress in Retinal and Eye Res. 21: 145-151, 2002.
Bennett et al. Humoral Response after Administration of E1-Deleted Adenoviruses: Immune Privilege of the Subretinal Space. Hum. Gene Ther. 7: 1763-1769, 1996.
Kole et al. Otx2-Genetically Modified Retinal Pigment Epithelial Cells Rescue Photoreceptors after Transplantation. Mol Ther. Jan. 3, 2018;26(1):219-237.
Robbins et al. Viral vectors for gene therapy. Pharmacology & therapeutics 80.1 (1998): 35-47.
Shahi et al., "Rescue of Kir7.1 function by gene augmentation in LCA16 patient derived iPSC-RPE cells," Investigative Ophthalmology & Visual Science 59(9):1196, 2018.
Miller, Daniel G., et al. "Large-scale analysis of adeno-associated virus vector integration sites in normal human cells." Journal of virology 79.17 (2005): 11434-11442.
Wang, D., et al. "Efficient CFTR expression from AAV vectors packaged with promoters-the second generation." Gene therapy 6.4 (1999): 667-675.
Non-Final Rejection in U.S. Appl. No. 17/911,367.

* cited by examiner g
h
i
j
Mit. Count / 10μm
AP length (μm)
0.12
0.97
10
5
0
2.2
2.0
1.8
Ctr.
LCA16
Control iPSC-RPE
LCA16 iPSC-RPE
Kir7.1,
ZO-1,
DAPI FIG. 3A
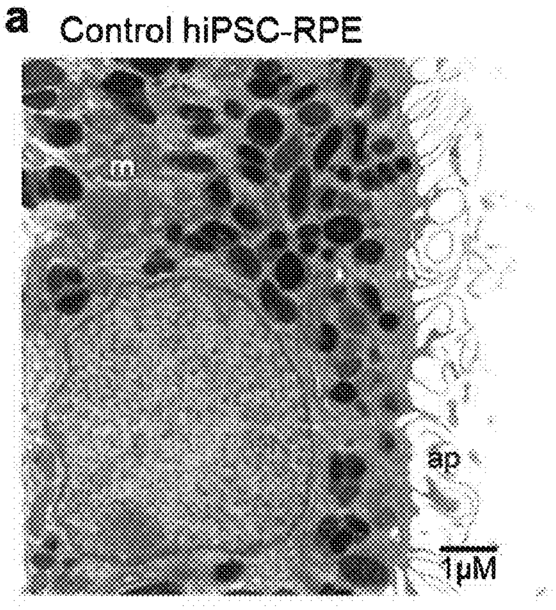
FIG. 3B
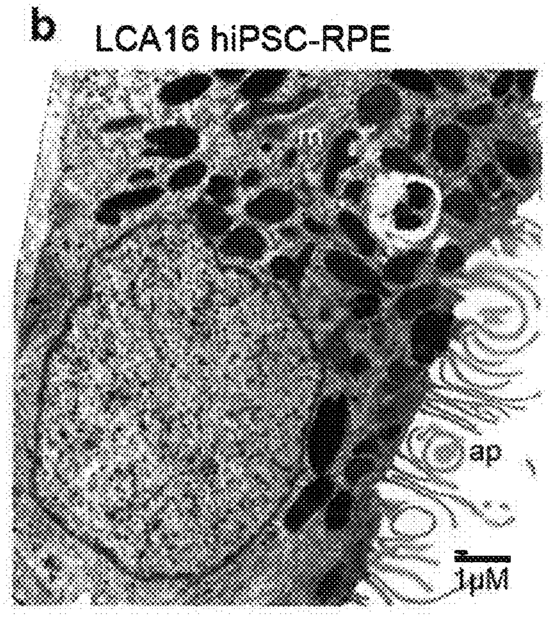
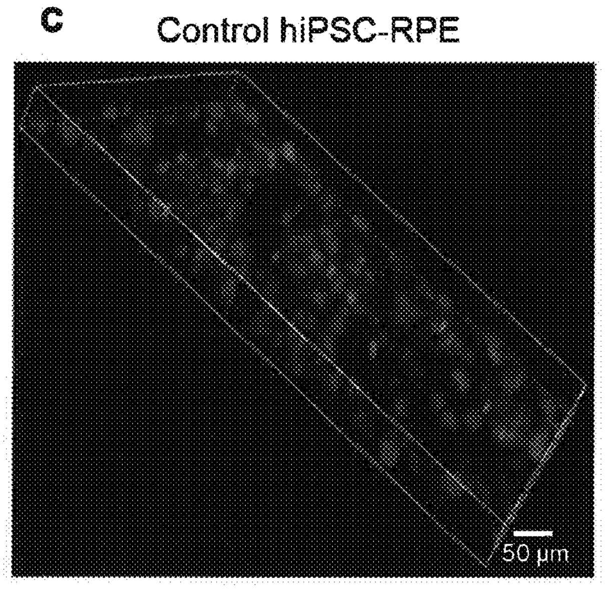
FIG. 3C
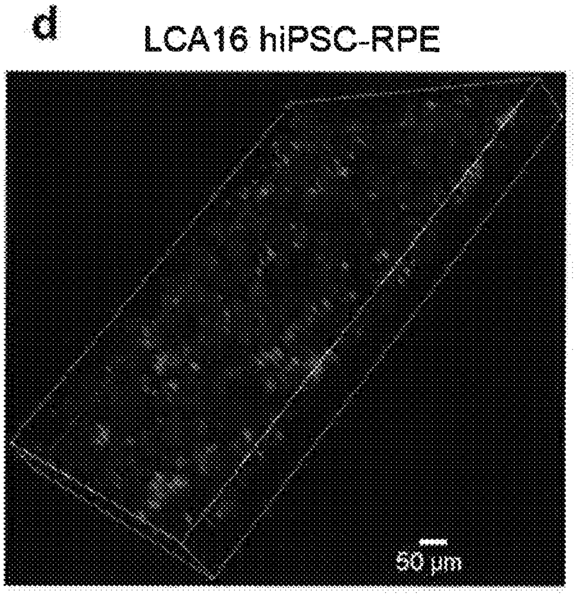
FIG. 3D FIG. 4A
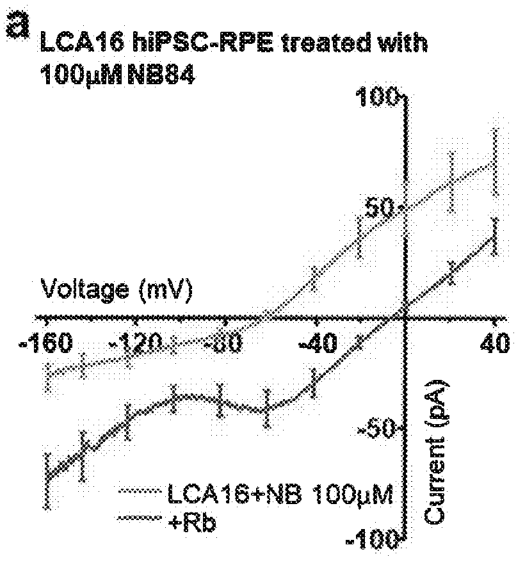
FIG. 4B
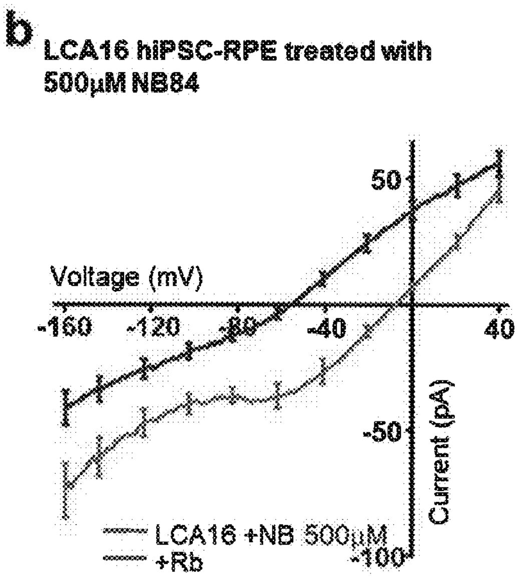
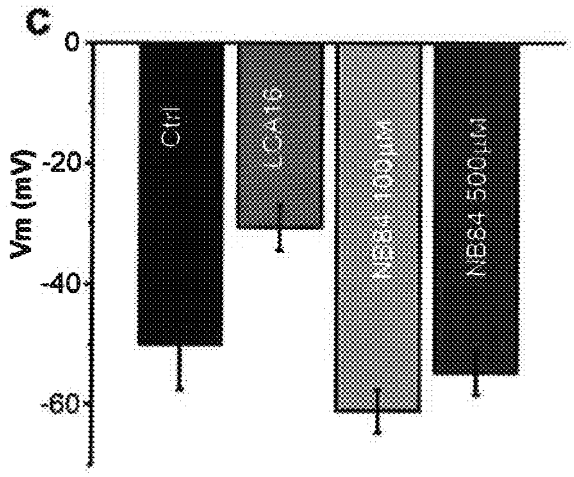
FIG. 4C
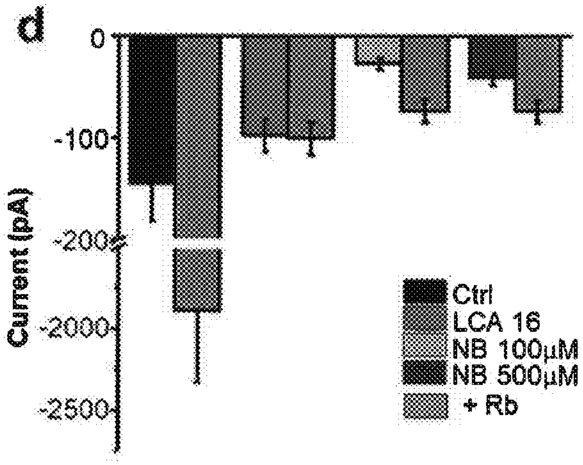
FIG. 4D
a LCA16 hiPSC-RPE treated with 100µM NB84
Voltage (mV)
-160 -120 -80 -40 40
100 50 -50 -100
Current (pA)
LCA16+NB 100µM
+Rb
c
Vm (mV)
0 -20 -40 -60
Ctrl
LCA16
NB84 100µM
NB84 500µM FIG. 5A
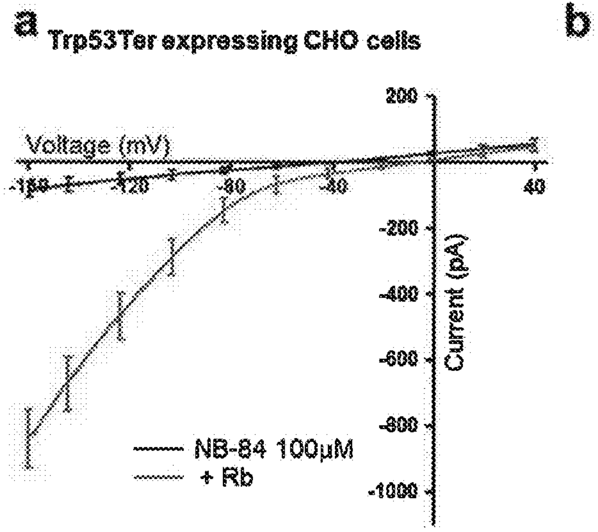
FIG. 5B
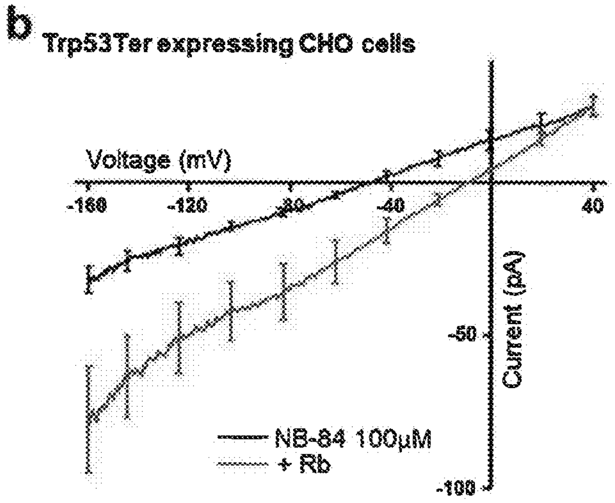
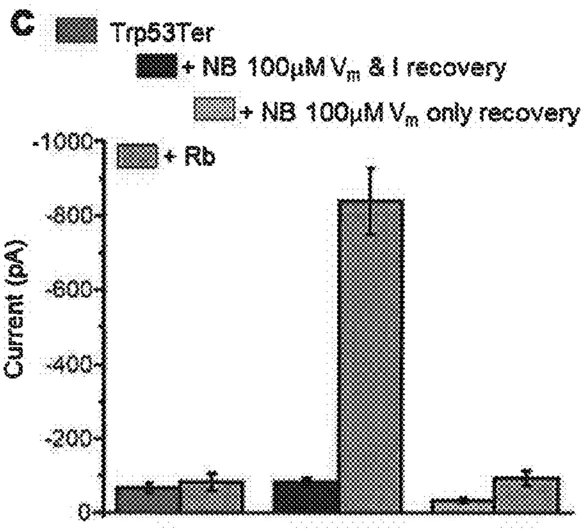
FIG. 5C
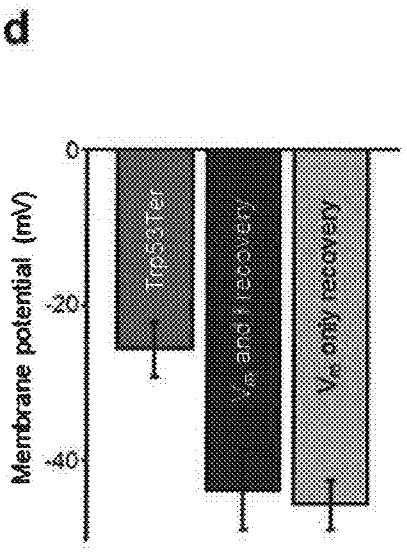
FIG. 5D

| Model | DoseResp |
| --- | --- |
| Equation | $y = min + \frac{(max - min)}{1 + 10^{(LOGhalfmax - x)*p}}$ |
| min | 0.02196 ± 0.00615 |
| max | 1.0099 ± 0.0132 |
| $half_{max}$ | 2.67698 ± 0.02807 |
| Hill Slope | 0.80772 ± 0.04123 |
| Reduced Chi-Sqr | 0.01212 |
| R-Square(COD) | 0.9999 |
| Adj. R-Square | 0.99958 |

FIG. 7A
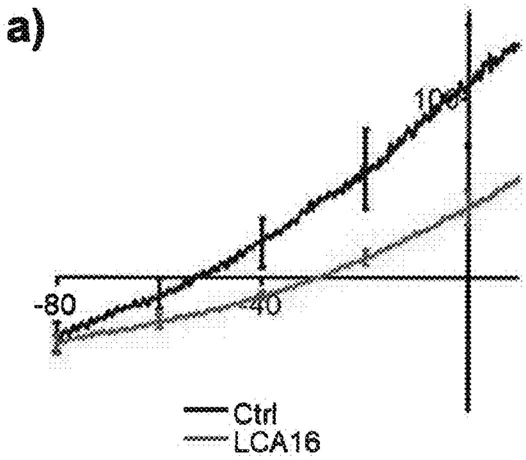
FIG. 7B
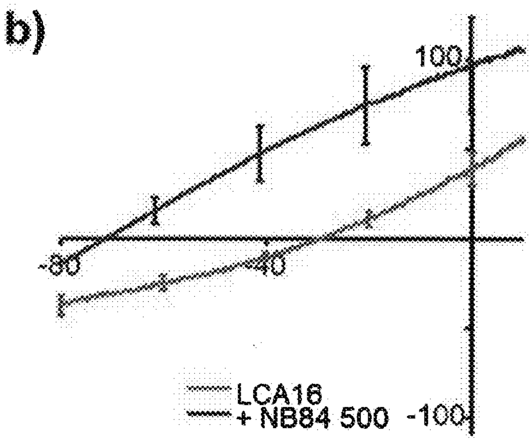
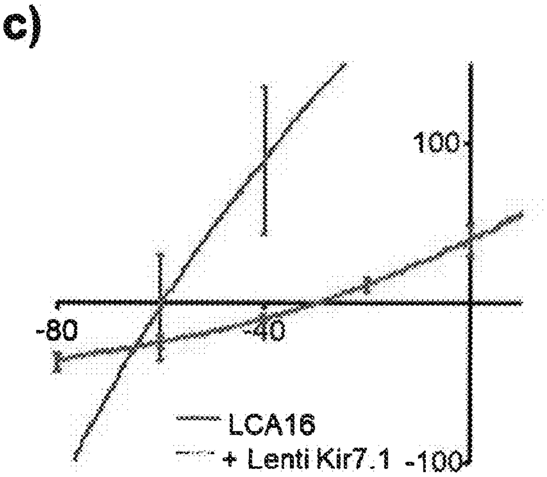
FIG. 7C
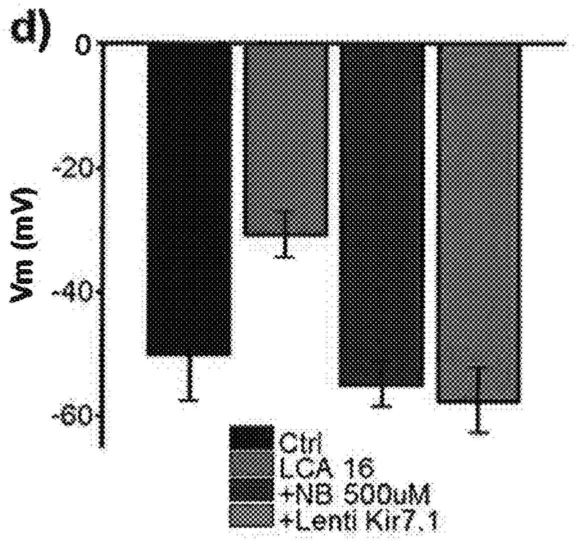
FIG. 7D

Whole-cell Kir7.1 current recorded in WT but not W53X stable cells
Voltage (mV)
Current (pA)
-160
-120
-80
-40
40
-1000
-2000
-3000
-4000
HR
Rb+
Voltage (mV)
Current (pA)
-160
-120
-80
-40
40
100
-100
-200
-300
-400
HR
Rb+

FIG. 10A
FIG. 10B
GFP-Kir7.1 expressed on the membrane of W53X stable CHO-K1 cells
A
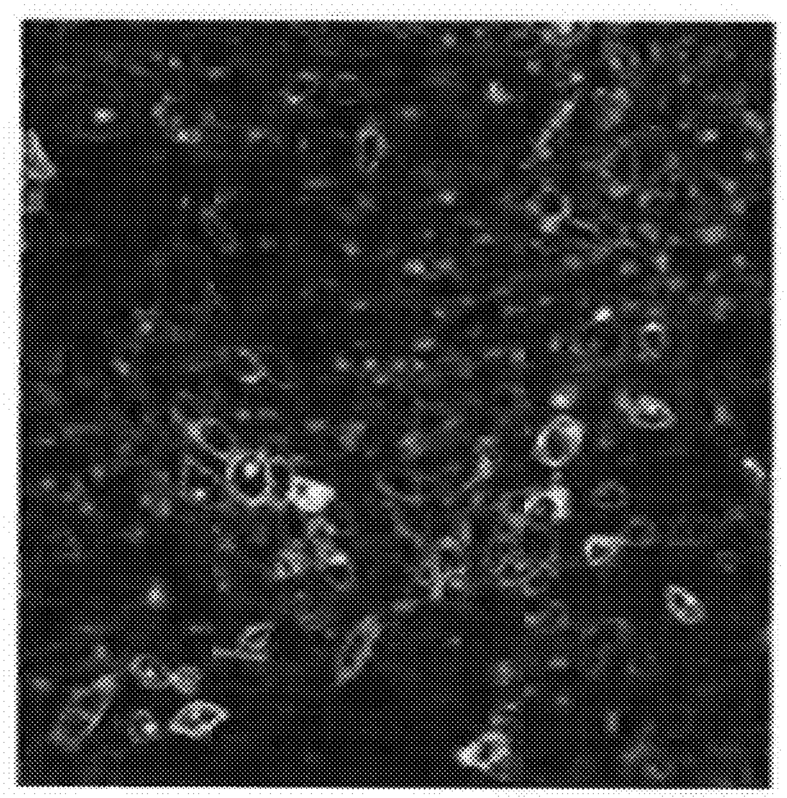
B
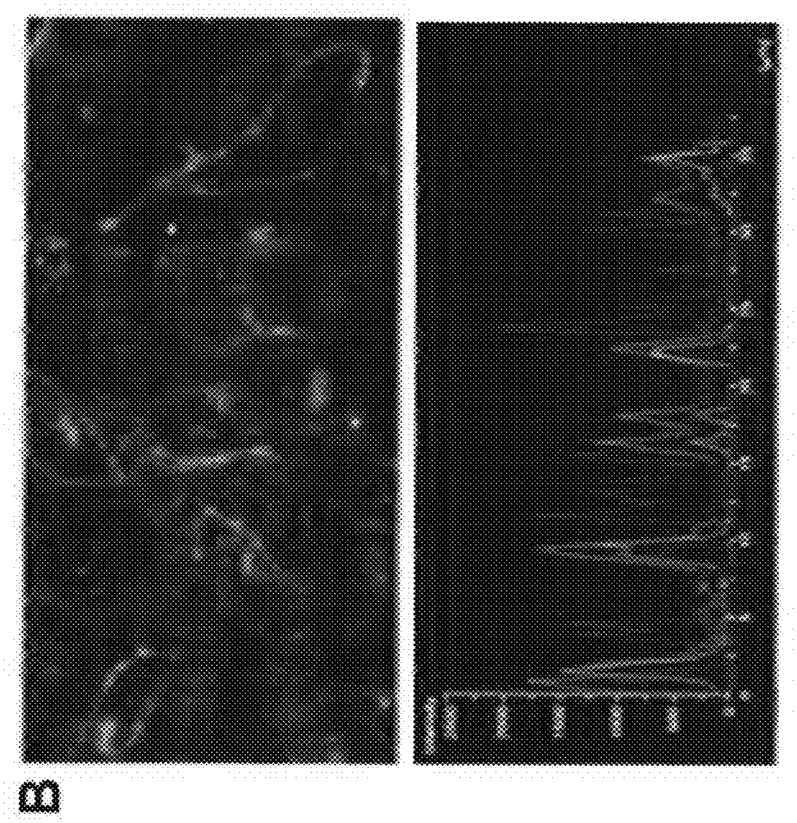

| | a-wave | b-wave | c-wave |
|---|---|---|---|
| Untreated | 192 | 387 | 19 |
| Treated | 138 | 178 | 608 |

Vector Map

User-inserted region
Adenovirus region
Bacterial region

5' ITR
pUC ori
EF1A
1 bp
Kozak
5627 bp
1125 bp
Ampicillin
6752 bp
4501 bp
2251 bp
{EGFP-Kir7.1}
3376 bp
3' ITR
SV40 late pA

FIG. 16

Table 2: Color-coded Vector Components

| Component name | Nucleotide position | Full Name | Description |
|---|---|---|---|
| 5' UTR | 1-141 | 5' inverted terminal repeat | Serve as the origin of viral genome replication |
| EF1A | 169-1347 | EF1A | Component entered by user |
| Kozak | 1372-1377 | Kozak | Component entered by user |
| {EGFP-Kir7.1} | 1378-3216 | {EGFP-Kir7.1} | Component entered by user |
| SV40 late pA | 3261-3482 | SV40 late polyadenylation signal | Allows transcription termination and polyadenylation of mRNA |
| 3' ITR | 3495-3635 | 3' inverted terminal repeat | Serve as the origin of viral genome replication |
| Ampicillin | 4716-5576 | Ampicillin resistance gene | Allows selection of plasmid in E. coli |
| pUC ori | 5747-6335 | pUC origin of replication | Permits high-copy replication and maintenance in E coli. |

FIG. 16 (continued)

| | | | | | | |
|---|---|---|---|---|---|---|
| 1 | CCTGCAGGCA | GCTGCGCGCT | CGCTCGCTCA | CTGAGGCCGC | CCGGGCAAAG | CCCGGGCGTC |
| 61 | GGGCGACCTT | TGGTCGCCCG | GCCTCAGTGA | GCGAGCGAGC | GCGCAGAGAG | GGAGTGGCCA |
| 121 | ACTCCATCAC | TAGGGGTTCC | TATCGATCAA | CTTTGTATAG | AAAAGTTGGG | CTCCGGTGCC |
| 181 | CGTCAGTGGG | CAGAGCGCAC | ATCGCCCACA | GTCCCCGAGA | AGTTGGGGGG | AGGGGTCGGC |
| 241 | AATTGAACCG | GTGCCTAGAG | AAGGTGGCGC | GGGGTAAACT | GGGAAAGTGA | TGTCGTGTAC |
| 301 | TGGCTCCGCC | TTTTTCCCGA | GGGTGGGGGA | GAACCGTATA | TAAGTGCAGT | AGTCGCCGTG |
| 361 | AACGTTCTTT | TTCGCAACGG | GTTTGCCGCC | AGAACACAGG | TAAGTGCCGT | GTGTGGTTCC |
| 421 | CGCGGGCCTG | GCCTCTTTAC | GGGTTATGGC | CCTTGCGTGC | CTTGAATTAC | TTCCACCTGG |
| 481 | CTGCAGTACG | TGATTCTTGA | TCCCGAGCTT | CGGGTTGGAA | GTGGGTGGGA | GAGTTCGAGG |
| 541 | CCTTGCGCTT | AAGGAGCCCC | TTCGCCTCGT | GCTTGAGTTG | AGGCCTGGCC | TGGGCGCTGG |
| 601 | GGCCGCCGCG | TGCGAATCTG | GTGGCACCTT | CGCGCCTGTC | TCGCTGCTTT | CGATAAGTCT |
| 661 | CTAGCCATTT | AAAATTTTTG | ATGACCTGCT | GCGACGCTTT | TTTTCTGGCA | AGATAGTCTT |
| 721 | GTAAATGCGG | GCCAAGATCT | GCACACTGGT | ATTTCGGTTT | TTGGGGCCGC | GGGCGGCGAC |
| 781 | GGGGCCCGTG | CGTCCCAGCG | CACATGTTCG | GCGAGGCGGG | GCCTGCGAGC | GCGGCCACCG |
| 841 | AGAATCGGAC | GGGGGTAGTC | TCAAGCTGGC | CGGCCTGCTC | TGGTGCCTGG | TCTCGCGCCG |
| 901 | CCGTGTATCG | CCCCGCCCTG | GGCGGCAAGG | CTGGCCCGGT | CGGCACCAGT | TGCGTGAGCG |
| 961 | GAAAGATGGC | CGCTTCCCGG | CCCTGCTGCA | GGGAGCTCAA | AATGGAGGAC | GCGGCGCTCG |
| 1021 | GGAGAGCGGG | CGGGTGAGTC | ACCCACACAA | AGGAAAAGGG | CCTTTCCGTC | CTCAGCCGTC |
| 1081 | GCTTCATGTG | ACTCCACGGA | GTACCGGGCG | CCGTCCAGGC | ACCTCGATTA | GTTCTCGAGC |
| 1141 | TTTTGGAGTA | CGTCGTCTTT | AGGTTGGGGG | GAGGGGTTTT | ATGCGATGGA | GTTTCCCCAC |
| 1201 | ACTGAGTGGG | TGGAGACTGA | AGTTAGGCCA | GCTTGGCACT | TGATGTAATT | CTCCTTGGAA |
| 1261 | TTTGCCCTTT | TTGAGTTTGG | ATCTTGGTTC | ATTCTCAAGC | CTCAGACAGT | GGTTCAAAGT |
| 1321 | TTTTTTCTTC | CATTTCAGGT | GTCGTGACAA | GTTTGTACAA | AAAAGCAGGC | TGCCACCATG |
| 1381 | [illegible] | [illegible] | [illegible] | [illegible] | [illegible] | [illegible] |
| 1441 | [illegible] | [illegible] | [illegible] | [illegible] | [illegible] | [illegible] |
| 1501 | [illegible] | [illegible] | [illegible] | [illegible] | [illegible] | [illegible] |
| 1561 | [illegible] | [illegible] | [illegible] | [illegible] | [illegible] | [illegible] |
| 1621 | [illegible] | [illegible] | [illegible] | [illegible] | [illegible] | [illegible] |
| 1681 | [illegible] | [illegible] | [illegible] | [illegible] | [illegible] | [illegible] |
| 1741 | [illegible] | [illegible] | [illegible] | [illegible] | [illegible] | [illegible] |
| 1801 | [illegible] | [illegible] | [illegible] | [illegible] | [illegible] | [illegible] |
| 1861 | [illegible] | [illegible] | [illegible] | [illegible] | [illegible] | [illegible] |
| 1921 | [illegible] | [illegible] | [illegible] | [illegible] | [illegible] | [illegible] |
| 1981 | [illegible] | [illegible] | [illegible] | [illegible] | [illegible] | [illegible] |
| 2041 | [illegible] | [illegible] | [illegible] | [illegible] | [illegible] | [illegible] |
| 2101 | [illegible] | [illegible] | [illegible] | [illegible] | [illegible] | [illegible] |
| 2161 | [illegible] | [illegible] | [illegible] | [illegible] | [illegible] | [illegible] |
| 2221 | [illegible] | [illegible] | [illegible] | [illegible] | [illegible] | [illegible] |
| 2281 | [illegible] | [illegible] | [illegible] | [illegible] | [illegible] | [illegible] |
| 2341 | [illegible] | [illegible] | [illegible] | [illegible] | [illegible] | [illegible] |
| 2401 | [illegible] | [illegible] | [illegible] | [illegible] | [illegible] | [illegible] |

FIG. 16 (continued)

2101 [illegible]
2161 [illegible]
2221 [illegible]
2281 [illegible]
2341 [illegible]
2401 [illegible]
2461 [illegible]
2521 [illegible]
2581 [illegible]
2641 [illegible]
2701 [illegible]
2761 [illegible]
2821 [illegible]
2881 [illegible]
2941 [illegible]

3001 [illegible]
3061 [illegible]
3121 [illegible]
3181 [illegible] ACCC AGCTTTCTTG TACAAAGTGG
3241 TGATGGCCGG CCGCTTCGAG CAGACATGAT AAGATACATT GATGAGTTTG GACAAACCAC
3301 AACTAGAATG CAGTGAAAAA AATGCTTTAT TTGTGAAATT TGTGATGCTA TTGCTTTATT
3361 TGTAACCATT ATAAGCTGCA ATAAACAAGT TAACAACAAC AATTGCATTC ATTTTATGTT
3421 TCAGGTTCAG GGGGAGGTGT GGGAGGTTTT TTAAAGCAAG TAAAACCTCT ACAAATGTGG
3481 TAATCGATAG ATCTAGGAAC CCCTAGTGAT GGAGTTGGCC ACTCCCTCTC TGCGCGCTCG
3541 CTCGCTCACT GAGGCCGGGC GACCAAAGGT CGCCCGACGC CCGGGCTTTG CCCGGGCGGC
3601 CTCAGTGAGC GAGCGAGCGC GCAGCTGCCT GCAGGCAGCT TGGCACTGGC CGTCGTTTTA
3661 CAACGTCGTG ACTGGGAAAA CCCTGGCGTT ACCCAACTTA ATCGCCTTGC AGCACATCCC
3721 CCTTTCGCCA GCTGGCGTAA TAGCGAAGAG GCCCGCACCG ATCGCCCTTC CCAACAGTTG
3781 CGCAGCCTGA ATGGCGAATG GCGCCTGATG CGGTATTTTC TCCTTACGCA TCTGTGCGGT
3841 ATTTCACACC GCATACGTCA AAGCAACCAT AGTACGCGCC CTGTAGCGGC GCATTAAGCG
3901 CGGCGGGTGT GGTGGTTACG CGCAGCGTGA CCGCTACACT TGCCAGCGCC CTAGCGCCCG
3961 CTCCTTTCGC TTTCTTCCCT TCCTTTCTCG CCACGTTCGC CGGCTTTCCC CGTCAAGCTC
4021 TAAATCGGGG GCTCCCTTTA GGGTTCCGAT TTAGTGCTTT ACGGCACCTC GACCCCAAAA
4081 AACTTGATTT GGGTGATGGT TCACGTAGTG GGCCATCGCC CTGATAGACG GTTTTTCGCC
4141 CTTTGACGTT GGAGTCCACG TTCTTTAATA GTGGACTCTT GTTCCAAACT GGAACAACAC
4201 TCAACCCTAT CTCGGGCTAT TCTTTTGATT TATAAGGGAT TTTGCCGATT TCGGCCTATT
4261 GGTTAAAAAA TGAGCTGATT TAACAAAAAT TTAACGCGAA TTTTAACAAA ATATTAACGT
4321 TTACAATTTT ATGGTGCACT CTCAGTACAA TCTGCTCTGA TGCCGCATAG TTAAGCCAGC
4381 CCCGACACCC GCCAACACCC GCTGACGCGC CCTGACGGGC TTGTCTGCTC CCGGCATCCG
4441 CTTACAGACA AGCTGTGACC GTCTCCGGGA GCTGCATGTG TCAGAGGTTT TCACCGTCAT
4501 CACCGAAACG CGCGAGACGA AAGGGCCTCG TGATACGCCT ATTTTTATAG GTTAATGTCA
4561 TGATAATAAT GGTTTCTTAG ACGTCAGGTG GCACTTTTCG GGGAAATGTG CGCGGAACCC
4621 CTATTTGTTT ATTTTTCTAA ATACATTCAA ATATGTATCC GCTCATGAGA CAATAACCCT
4681 GATAAATGCT TCAATAATAT TGAAAAAGGA AGAGTATGAG TATTCAACAT TTCCGTGTCG

FIG. 16 (continued)

4741 CCCTTATTCC CTTTTTTGCG GCATTTTGCC TTCCTGTTTT TGCTCACCCA GAAACGCTGG
4801 TGAAAGTAAA AGATGCTGAA GATCAGTTGG GTGCACGAGT GGGTTACATC GAACTGGATC
4861 TCAACAGCGG TAAGATCCTT GAGAGTTTTC GCCCCGAAGA ACGTTTTCCA ATGATGAGCA
4921 CTTTTAAAGT TCTGCTATGT GGCGCGGTAT TATCCCGTAT TGACGCCGGG CAAGAGCAAC
4981 TCGGTCGCCG CATACACTAT TCTCAGAATG ACTTGGTTGA GTACTCACCA GTCACAGAAA
5041 AGCATCTTAC GGATGGCATG ACAGTAAGAG AATTATGCAG TGCTGCCATA ACCATGAGTG
5101 ATAACACTGC GGCCAACTTA CTTCTGACAA CGATCGGAGG ACCGAAGGAG CTAACCGCTT
5161 TTTTGCACAA CATGGGGGAT CATGTAACTC GCCTTGATCG TTGGGAACCG GAGCTGAATG
5221 AAGCCATACC AAACGACGAG CGTGACACCA CGATGCCTGT AGCAATGGCA ACAACGTTGC
5281 GCAAACTATT AACTGGCGAA CTACTTACTC TAGCTTCCCG GCAACAATTA ATAGACTGGA
5341 TGGAGGCGGA TAAAGTTGCA GGACCACTTC TGCGCTCGGC CCTTCCGGCT GGCTGGTTTA
5401 TTGCTGATAA ATCTGGAGCC GGTGAGCGTG GGTCTCGCGG TATCATTGCA GCACTGGGGC
5461 CAGATGGTAA GCCCTCCCGT ATCGTAGTTA TCTACACGAC GGGGAGTCAG GCAACTATGG
5521 ATGAACGAAA TAGACAGATC GCTGAGATAG GTGCCTCACT GATTAAGCAT TGGTAACTGT
5581 CAGACCAAGT TTACTCATAT ATACTTTAGA TTGATTTAAA ACTTCATTTT TAATTTAAAA
5641 GGATCTAGGT GAAGATCCTT TTTGATAATC TCATGACCAA AATCCCTTAA CGTGAGTTTT
5701 CGTTCCACTG AGCGTCAGAC CCCGTAGAAA AGATCAAAGG ATCTTCTTGA GATCCTTTTT
5761 TTCTGCGCGT AATCTGCTGC TTGCAAACAA AAAAACCACC GCTACCAGCG GTGGTTTGTT
5821 TGCCGGATCA AGAGCTACCA ACTCTTTTTC CGAAGGTAAC TGGCTTCAGC AGAGCGCAGA
5881 TACCAAATAC TGTTCTTCTA GTGTAGCCGT AGTTAGGCCA CCACTTCAAG AACTCTGTAG
5941 CACCGCCTAC ATACCTCGCT CTGCTAATCC TGTTACCAGT GGCTGCTGCC AGTGGCGATA
6001 AGTCGTGTCT TACCGGGTTG GACTCAAGAC GATAGTTACC GGATAAGGCG CAGCGGTCGG
6061 GCTGAACGGG GGGTTCGTGC ACACAGCCCA GCTTGGAGCG AACGACCTAC ACCGAACTGA
6121 GATACCTACA GCGTGAGCTA TGAGAAAGCG CCACGCTTCC CGAAGGGAGA AAGGCGGACA
6181 GGTATCCGGT AAGCGGCAGG GTCGGAACAG GAGAGCGCAC GAGGGAGCTT CCAGGGGGAA
6241 ACGCCTGGTA TCTTTATAGT CCTGTCGGGT TTCGCCACCT CTGACTTGAG CGTCGATTTT
6301 TGTGATGCTC GTCAGGGGGG CGGAGCCTAT GGAAAAACGC CAGCAACGCG GCCTTTTTAC
6361 GGTTCCTGGC CTTTTGCTGG CCTTTTGCTC ACATGTTCTT TCCTGCGTTA TCCCCTGATT
6421 CTGTGGATAA CCGTATTACC GCCTTTGAGT GAGCTGATAC CGCTCGCCGC AGCCGAACGA
6481 CCGAGCGCAG CGAGTCAGTG AGCGAGGAAG CGGAAGAGCG CCCAATACGC AAACCGCCTC
6541 TCCCCGCGCG TTGGCCGATT CATTAATGCA GCTGGCACGA CAGGTTTCCC GACTGGAAAG
6601 CGGGCAGTGA GCGCAACGCA ATTAATGTGA GTTAGCTCAC TCATTAGGCA CCCCAGGCTT
6661 TACACTTTAT GCTTCCGGCT CGTATGTTGT GTGGAATTGT GAGCGGATAA CAATTTCACA
6721 CAGGAAACAG CTATGACCAT GATTACGAAT TC

FIG. 17

Table 5: Color-coded Vector Components

| Comp. | Nt position | Full Name | Description |
|---|---|---|---|
| RSV promoter | 1-229 | Rous sarcoma virus enhancer/promoter | Allows Tat-independent production of viral mRNA |
| Δ5' LTR | 230-410 | HIV-1 truncated 5' LTR | Permits viral packaging and reverse transcription of the viral mRNA |
| Ψ | 521-568 | HIV-1 psi packaging signal | Allows viral packaging |
| RRE | 1075-1308 | HIV-1 Rev response element | Permits Rev-dependent nuclear export of unspliced viral mRNA |
| cPPT | 1803-1920 | Central polypurine tract | Facilitates the nuclear import of HIV-1 cDNA through a central DNA flap |
| EF1A | 1959-3137 | EF1A | Component entered by user |
| Kozak | 3162-3167 | Kozak | Component entered by user |
| {EGFP-Kir7.1} | 3168-5006 | {EGFP-Kir7.1} | Component entered by user |
| WPRE | 5045-5642 | Woodchuck hepatitis virus posttranscriptional regulatory element | Facilitates effective transcription termination at the 3' LTR |
| PGK promoter | 5661-6171 | Mouse phosphoglycerate kinase promoter | Allows high-level expression of the selection marker in mammalian cell lines |
| Blasticidin | 6243-6641 | Blasticidin resistance gene | Permits selection of stably transduced mammalian cell lines |
| ΔU3/3' LTR | 6727-6961 | HIV-1 truncated 3' LTR | Allows viral packaging but self-inactivates the 5' LTR for biosafety purposes. The element also contains a polyadenylation signal for transcription termination and polyadenylation of mRNA in transduced cells. |
| SV40 early pA | 7034-7168 | SV40 early polyadenylation signal | Allows transcription termination and polyadenylation of mRNA |
| Ampicillin | 8122-8982 | Ampicillin resistance gene | Allows selection of plasmid in E. coli |
| pUC ori | 9153-9741 | pUC origin of replication | Permits high-copy replication and maintenance in E coli. |

FIG. 17 (continued)

Table 6: Color-Coded Vector Sequence (SEQ ID NO: 10)

| | | | | | | |
|---|---|---|---|---|---|---|
| 1 | AATGTAGTCT | TATGCAATAC | TCTTGTAGTC | TTGCAACATG | GTAACGATGA | GTTAGCAACA |
| 61 | TGCCTTACAA | GGAGAGAAAA | AGCACCGTGC | ATGCCGATTG | GTGGAAGTAA | GGTGGTACGA |
| 121 | TCGTGCCTTA | TTAGGAAGGC | AACAGACGGG | TCTGACATGG | ATTGGACGAA | CCACTGAATT |
| 181 | GCCGCATTGC | AGAGATATTG | TATTTAAGTG | CCTAGCTCGA | TACATAAACG | GGTCTCTCTG |
| 241 | GTTAGACCAG | ATCTGAGCCT | GGGAGCTCTC | TGGCTAACTA | GGGAACCCAC | TGCTTAAGCC |
| 301 | TCAATAAAGC | TTGCCTTGAG | TGCTTCAAGT | AGTGTGTGCC | CGTCTGTTGT | GTGACTCTGG |
| 361 | TAACTAGAGA | TCCCTCAGAC | CCTTTTAGTC | AGTGTGGAAA | ATCTCTAGCA | GTGGCGCCCG |
| 421 | AACAGGGACT | TGAAAGCGAA | AGGGAAACCA | GAGGAGCTCT | CTCGACGCAG | GACTCGGCTT |
| 481 | GCTGAAGCGC | GCACGGCAAG | AGGCGAGGGG | CGGCGACTGG | TGAGTACGCC | AAAAATTTTG |
| 541 | ACTAGCGGAG | GCTAGAAGGA | GAGAGATGGG | TGCGAGAGCG | TCAGTATTAA | GCGGGGGAGA |
| 601 | ATTAGATCGC | GATGGGAAAA | AATTCGGTTA | AGGCCAGGGG | GAAAGAAAAA | ATATAAATTA |
| 661 | AAACATATAG | TATGGGCAAG | CAGGGAGCTA | GAACGATTCG | CAGTTAATCC | TGGCCTGTTA |
| 721 | GAAACATCAG | AAGGCTGTAG | ACAAATACTG | GGACAGCTAC | AACCATCCCT | TCAGACAGGA |
| 781 | TCAGAAGAAC | TTAGATCATT | ATATAATACA | GTAGCAACCC | TCTATTGTGT | GCATCAAAGG |
| 841 | ATAGAGATAA | AAGACACCAA | GGAAGCTTTA | GACAAGATAG | AGGAAGAGCA | AAACAAAAGT |
| 901 | AAGACCACCG | CACAGCAAGC | GGCCGCTGAT | CTTCAGACCT | GGAGGAGGAG | ATATGAGGGA |
| 961 | CAATTGGAGA | AGTGAATTAT | ATAAATATAA | AGTAGTAAAA | ATTGAACCAT | TAGGAGTAGC |
| 1021 | ACCCACCAAG | GCAAAGAGAA | GAGTGGTGCA | GACAGAAAAA | AGAGCAGTGG | GAATAGGAGC |
| 1081 | TTTGTTCCTT | GGGTTCTTGG | GAGCAGCAGG | AAGCACTATG | GGCGCAGCGT | CAATGACGCT |
| 1141 | GACGGTACAG | GCCAGACAAT | TATTGTCTGG | TATAGTGCAG | CAGCAGAACA | ATTTGCTGAG |
| 1201 | GGCTATTGAG | GCGCAACAGC | ATCTGTTGCA | ACTCACAGTC | TGGGGCATCA | AGCAGCTCCA |
| 1261 | GGCAAGAATC | CTGGCTGTGG | AAAGATACCT | AAAGGATCAA | CAGCTCCTGG | GGATTTGGGG |
| 1321 | TTGCTCTGGA | AAACTCATTT | GCACCACTGC | TGTGCCTTGG | AATGCTAGTT | GGAGTAATAA |
| 1381 | ATCTCTGGAA | CAGATTTGGA | ATCACACGAC | CTGGATGGAG | TGGGACAGAG | AAATTAACAA |
| 1441 | TTACACAAGC | TTAATACACT | CCTTAATTGA | AGAATCGCAA | AACCAGCAAG | AAAAGAATGA |
| 1501 | ACAAGAATTA | TTGGAATTAG | ATAAATGGGC | AAGTTTGTGG | AATTGGTTTA | ACATAACAAA |
| 1561 | TTGGCTGTGG | TATATAAAAT | TATTCATAAT | GATAGTAGGA | GGCTTGGTAG | GTTTAAGAAT |
| 1621 | AGTTTTTGCT | GTACTTTCTA | TAGTGAATAG | AGTTAGGCAG | GGATATTCAC | CATTATCGTT |
| 1681 | TCAGACCCAC | CTCCCAACCC | CGAGGGGACC | CGACAGGCCC | GAAGGAATAG | AAGAAGAAGG |
| 1741 | TGGAGAGAGA | GACAGAGACA | GATCCATTCG | ATTAGTGAAC | GGATCTCGAC | GGTATCGCTA |
| 1801 | GCTTTTAAAA | GAAAAGGGGG | GATTGGGGGG | TACAGTGCAG | GGGAAAGAAT | AGTAGACATA |
| 1861 | ATAGCAACAG | ACATACAAAC | TAAAGAATTA | CAAAAACAAA | TTACAAAAAT | TCAAAATTTT |

FIG. 17 (continued)

| | | | | | | |
|---|---|---|---|---|---|---|
| 1921 | ACTAGTGATT | ATCGGATCAA | CTTTGTATAG | AAAAGTTGGG | CTCCGGTGCC | CGTCAGTGGG |
| 1981 | CAGAGCGCAC | ATCGCCCACA | GTCCCCGAGA | AGTTGGGGGG | AGGGGTCGGC | AATTGAACCG |
| 2041 | GTGCCTAGAG | AAGGTGGCGC | GGGGTAAACT | GGGAAAGTGA | TGTCGTGTAC | TGGCTCCGCC |
| 2101 | TTTTTCCCGA | GGGTGGGGGA | GAACCGTATA | TAAGTGCAGT | AGTCGCCGTG | AACGTTCTTT |
| 2161 | TTCGCAACGG | GTTTGCCGCC | AGAACACAGG | TAAGTGCCGT | GTGTGGTTCC | CGCGGGCCTG |
| 2221 | GCCTCTTTAC | GGGTTATGGC | CCTTGCGTGC | CTTGAATTAC | TTCCACCTGG | CTGCAGTACG |
| 2281 | TGATTCTTGA | TCCCGAGCTT | CGGGTTGGAA | GTGGGTGGGA | GAGTTCGAGG | CCTTGCGCTT |
| 2341 | AAGGAGCCCC | TTCGCCTCGT | GCTTGAGTTG | AGGCCTGGCC | TGGGCGCTGG | GGCCGCCGCG |
| 2401 | TGCGAATCTG | GTGGCACCTT | CGCGCCTGTC | TCGCTGCTTT | CGATAAGTCT | CTAGCCATTT |
| 2461 | AAAATTTTTG | ATGACCTGCT | GCGACGCTTT | TTTTCTGGCA | AGATAGTCTT | GTAAATGCGG |
| 2521 | GCCAAGATCT | GCACACTGGT | ATTTCGGTTT | TTGGGGCCGC | GGGCGGCGAC | GGGGCCCGTG |
| 2581 | CGTCCCAGCG | CACATGTTCG | GCGAGGCGGG | GCCTGCGAGC | GCGGCCACCG | AGAATCGGAC |
| 2641 | GGGGGTAGTC | TCAAGCTGGC | CGGCCTGCTC | TGGTGCCTGG | CCTCGCGCCG | CCGTGTATCG |
| 2701 | CCCCGCCCTG | GGCGGCAAGG | CTGGCCCGGT | CGGCACCAGT | TGCGTGAGCG | GAAAGATGGC |
| 2761 | CGCTTCCCGG | CCCTGCTGCA | GGGAGCTCAA | AATGGAGGAC | GCGGCGCTCG | GGAGAGCGGG |
| 2821 | CGGGTGAGTC | ACCCACACAA | AGGAAAAGGG | CCTTTCCGTC | CTCAGCCGTC | GCTTCATGTG |
| 2881 | ACTCCACGGA | GTACCGGGCG | CCGTCCAGGC | ACCTCGATTA | GTTCTCGAGC | TTTTGGAGTA |
| 2941 | CGTCGTCTTT | AGGTTGGGGG | GAGGGGTTTT | ATGCGATGGA | GTTTCCCCAC | ACTGAGTGGG |
| 3001 | TGGAGACTGA | AGTTAGGCCA | GCTTGGCACT | TGATGTAATT | CTCCTTGGAA | TTTGCCCTTT |
| 3061 | TTGAGTTTGG | ATCTTGGTTC | ATTCTCAAGC | CTCAGACAGT | GGTTCAAAGT | TTTTTTCTTC |
| 3121 | CATTTCAGGT | GTCGTGACAA | GTTTGTACAA | AAAAGCAGGC | T**GCCACC**ATG | GTGAGCAAGG |
| 3181 | GCGAGGAGCT | GTTCACCGGG | GTGGTGCCCA | TCCTGGTCGA | GCTGGACGGC | GACGTAAACG |
| 3241 | GCCACAAGTT | CAGCGTGTCC | GGCGAGGGCG | AGGGCGATGC | CACCTACGGC | AAGCTGACCC |
| 3301 | TGAAGTTCAT | CTGCACCACC | GGCAAGCTGC | CCGTGCCCTG | GCCCACCCTC | GTGACCACCC |
| 3361 | TGACCTACGG | CGTGCAGTGC | TTCAGCCGCT | ACCCCGACCA | CATGAAGCAG | CACGACTTCT |
| 3421 | TCAAGTCCGC | CATGCCCGAA | GGCTACGTCC | AGGAGCGCAC | CATCTTCTTC | AAGGACGACG |
| 3481 | GCAACTACAA | GACCCGCGCC | GAGGTGAAGT | TCGAGGGCGA | CACCCTGGTG | AACCGCATCG |
| 3541 | AGCTGAAGGG | CATCGACTTC | AAGGAGGACG | GCAACATCCT | GGGGCACAAG | CTGGAGTACA |
| 3601 | ACTACAACAG | CCACAACGTC | TATATCATGG | CCGACAAGCA | GAAGAACGGC | ATCAAGGTGA |
| 3661 | ACTTCAAGAT | CCGCCACAAC | ATCGAGGACG | GCAGCGTGCA | GCTCGCCGAC | CACTACCAGC |
| 3721 | AGAACACCCC | CATCGGCGAC | GGCCCCGTGC | TGCTGCCCGA | CAACCACTAC | CTGAGCACCC |
| 3781 | AGTCCGCCCT | GAGCAAAGAC | CCCAACGAGA | AGCGCGATCA | CATGGTCCTG | CTGGAGTTCG |
| 3841 | TGACCGCCGC | CGGGATCACT | CTCGGCATGG | ACGAGCTGTA | CAAGTCCGGA | CTCAGATCTC |
| 3901 | GAGCTCAAGC | TTCGAATTCT | GACACCAGTA | ATTGCAAAGT | TATTGCCCCT | CTCCCTAAGC |
| 3961 | AAAGATACCC | GAGGATGGTC | ACCAAGCATG | CCCACAGCAC | ACTTCAAATG | GATGCCGCTC |
| 4021 | AAACAGGTCT | TGTATATCTT | CCAGATGCTT | GGGGAATCCT | AATGGACATG | CGCTGCGCTT |
| 4081 | GCATGATGTT | GGTCTTTTCT | GCTTCTTTTG | TTGTCCACTG | GCTTTGTCTT | GCAGTGCTCT |
| 4141 | GGTATGTTCT | GGCTGAGATT | AATGGCGATC | TGGAACTAGA | TCATGATGCC | GCACCTGAAA |
| 4201 | ACCACACTAT | CTGTGTCAAG | TATATCACCA | GTTTCACAGC | TCCATTCTGC | TTCTCCCTGG |
| 4261 | AGACACAACT | CACAATTGGT | TATGGTACCA | TGTTCCCCAG | TGGTGACTGT | CCAAGTGCAA |
| 4321 | TCAGCTTACT | TGCCATACAA | ATCCTGCTAG | GCCTCATGCT | AGAGGCTTTT | ATCACAGGTG |
| 4381 | CTTTTGTGGC | CAAGATTGCC | CGGCCAAAAA | ATCGAGCTTT | TTCAATTCGC | TTTACTGACA |
| 4441 | CAGCAGTAGT | AGCTCACATG | GATGGCAAAC | CTAATCTTAT | CTTCCAAGTG | GCCAACACCC |
| 4501 | GACCTAGCCC | TCTAACCAGT | GTCCGGGTCT | CAGCTGTACT | CTATCAGGAA | AGAGAAAATG |
| 4561 | GCAAACTCTA | CCAGACCAGT | GTGGATTTCC | ACCTTGATGG | CATCAGTTCT | GACGAATGTC |
| 4621 | CATTCTTCAT | CTTTCCACTA | ACGTATTATC | ACTCCATTAC | ACCATCAAGT | CCTCTGGCTA |
| 4681 | CTCTGCTCCA | GCATGAAAAT | CCTTCTCACT | TTGAATTAGT | TGTATTCCTT | TCAGCAATGG |

FIG. 17 (continued)

| | | | | | | |
|---|---|---|---|---|---|---|
| 4741 | AGGAGGGCAC | TGGACAAATA | TCCCAAAGGA | GCACATCCTA | CCTACCCTCT | GAAATCATGT |
| 4801 | TACATCACTG | TTTTCCATCT | CTGTTCACCC | GAGCTTTCAA | ACCTCAATAT | CAAATCAAGA |
| 4861 | TTGAGAATTT | TAACAAGACT | CTCCCTTAAT | TTCAAATTCC | TCTGCTTTCT | AAAAGCCCAA |
| 4921 | ACACCACTTA | CCTGGATATC | CACATCAATG | CACAAACCAT | TGACAATTTT | CACATCTCTC |
| 4981 | AAACAGGACT | GACAGAATAA | CGATCCACCC | AGCTTTCTTG | TACAAAGTGG | TGATAATCGA |
| 5041 | ATT**CCGATAA** | TCAACCTCTG | **GATTACAAAA** | TTTGTGAAAG | **ATTGACTGGT** | **ATTCTTAACT** |
| 5101 | **ATGTTGCTCC** | TTTTACGCTA | **TGTGGATACG** | CTGCTTTAAT | **GCCTTTGTAT** | **CATGCTATTG** |
| 5161 | **CTTCCCGTAT** | GGCTTTCATT | **TTCTCCTCCT** | TGTATAAATC | **CTGGTTGCTG** | **TCTCTTTATG** |
| 5221 | **AGGAGTTGTG** | GCCCGTTGTC | **AGGCAACGTG** | GCGTGGTGTG | **CACTGTGTTT** | **GCTGACGCAA** |
| 5281 | **CCCCCACTGG** | TTGGGGCATT | **GCCACCACCT** | GTCAGCTCCT | **TTCCGGGACT** | **TTCGCTTTCC** |
| 5341 | **CCCTCCCTAT** | TGCCACGGCG | **GAACTCATCG** | CCGCCTGCCT | **TGCCCGCTGC** | **TGGACAGGGG** |
| 5401 | **CTCGGCTGTT** | GGGCACTGAC | **AATTCCGTGG** | TGTTGTCGGG | **GAAGCTGACG** | **TCCTTTCCAT** |
| 5461 | **GGCTGCTCGC** | CTGTGTTGCC | **ACCTGGATTC** | TGCGCGGGAC | **GTCCTTCTGC** | **TACGTCCCTT** |
| 5521 | **CGGCCCTCAA** | TCCAGCGGAC | **CTTCCTTCCC** | GCGGCCTGCT | **GCCGGCTCTG** | **CGGCCTCTTC** |
| 5581 | **CGCGTCTTCG** | CCTTCGCCCT | **CAGACGAGTC** | GGATCTCCCT | **TTGGGCCGCC** | **TCCCCGCATC** |
| 5641 | **GG**GAATTCCC | GCGGTTCGAA | TTCTACCGGG | TAGGGGAGGC | GCTTTTCCCA | AGGCAGTCTG |
| 5701 | GACCATGCGC | TTTAGCAGCC | CCGCTGGGCA | CTTGGCGCTA | CACAAGTGGC | CTCTGGCCTC |
| 5761 | GCACACATTC | CACATCCACC | GGTAGGCGCC | AACCGGCTCC | GTTCTTTGGT | GGCCCCTTCG |
| 5821 | CGCCACCTTC | TACTCCTCCC | CTAGTCAGGA | AGTTCCCCCC | CGCCCCGCAG | CTCGCGTCGT |
| 5881 | GCAGGACGTG | ACAAATGGAA | GTAGCACGTC | TCACTAGTCT | CGTGCAGATG | GACAGCACCG |
| 5941 | CTGAGCAATG | GAAGCGGGTA | GGCCTTTGGG | GCAGCGGCCA | ATAGCAGCTT | TGCTCCTTCG |
| 6001 | CTTTCTGGGC | TCAGAGGCTG | GGAAGGGGTG | GGTCCGGGGG | CGGGCTCAGG | GGCGGGCTCA |
| 6061 | GGGGCGGGGC | GGGCGCCCGA | AGGTCCTCCG | GAGGCCCGGC | ATTCTGCACG | CTTCAAAAGC |

FIG. 17 (continued)

| | | | | | | |
|---|---|---|---|---|---|---|
| 6121 | GCACGTCTGC | CGCGCTGTTC | TCCTCTTCCT | CATCTCCGGG | CCTTTCGACC | TCACGTGTTG |
| 6181 | ACAATTAATC | ATCGGCATAG | TATATCGGCA | TAGTATAATA | CGACAAGGTG | AGGAACTAAA |
| 6241 | CC**ATGGCCAA** | **GCCTTTGTCT** | **CAAGAAGAAT** | **CCACCCTCAT** | **TGAAAGAGCA** | **ACGGCTACAA** |
| 6301 | **TCAACAGCAT** | **CCCCATCTCT** | **GAAGACTACA** | **GCGTCGCCAG** | **CGCAGCTCTC** | **TCTAGCGACG** |
| 6361 | **GCCGCATCTT** | **CACTGGTGTC** | **AATGTATATC** | **ATTTTACTGG** | **GGGACCTTGT** | **GCAGAACTCG** |
| 6421 | **TGGTGCTGGG** | **CACTGCTGCT** | **GCTGCGGCAG** | **CTGGCAACCT** | **GACTTGTATC** | **GTCGCGATCG** |
| 6481 | **GAAATGAGAA** | **CAGGGGCATC** | **TTGAGCCCCT** | **GCGGACGGTG** | **CCGACAGGTG** | **CTTCTCGATC** |
| 6541 | **TGCATCCTGG** | **GATCAAAGCC** | **ATAGTGAAGG** | **ACAGTGATGG** | **ACAGCCGACG** | **GCAGTTGGGA** |
| 6601 | **TTCGTGAATT** | **GCTGCCCTCT** | **GGTTATGTGT** | **GGGAGGGCTA** | **A**GCACAATTC | GAGCTCGGTA |
| 6661 | CCTTTAAGAC | CAATGACTTA | CAAGGCAGCT | GTAGATCTTA | GCCACTTTTT | AAAAGAAAAG |
| 6721 | GGGGGACTGG | AAGGGCTAAT | TCACTCCCAA | CGAAGACAAG | ATCTGCTTTT | TGCTTGTACT |
| 6781 | GGGTCTCTCT | GGTTAGACCA | GATCTGAGCC | TGGGAGCTCT | CTGGCTAACT | AGGGAACCCA |
| 6841 | CTGCTTAAGC | CTCAATAAAG | CTTGCCTTGA | GTGCTTCAAG | TAGTGTGTGC | CCGTCTGTTG |
| 6901 | TGTGACTCTG | GTAACTAGAG | ATCCCTCAGA | CCCTTTTAGT | CAGTGTGGAA | AATCTCTAGC |
| 6961 | AGTAGTAGTT | CATGTCATCT | TATTATTCAG | TATTTATAAC | TTGCAAAGAA | ATGAATATCA |
| 7021 | GAGAGTGAGA | GGA**ACTTGTT** | **TATTGCAGCT** | **TATAATGGTT** | **ACAAATAAAG** | **CAATAGCATC** |
| 7081 | **ACAAATTTCA** | **CAAATAAAGC** | **ATTTTTTTCA** | **CTGCATTCTA** | **GTTGTGGTTT** | **GTCCAAACTC** |
| 7141 | **ATCAATGTAT** | **CTTATCATGT** | **CTGGCTCT**AG | CTATCCCGCC | CCTAACTCCG | CCCATCCCGC |
| 7201 | CCCTAACTCC | GCCCAGTTCC | GCCCATTCTC | CGCCCCATGG | CTGACTAATT | TTTTTTATTT |
| 7261 | ATGCAGAGGC | CGAGGCCGCC | TCGGCCTCTG | AGCTATTCCA | GAAGTAGTGA | GGAGGCTTTT |
| 7321 | TTGGAGGCCT | AGGGACGTAC | CCAATTCGCC | CTATAGTGAG | TCGTATTACG | CGCGCTCACT |
| 7381 | GGCCGTCGTT | TTACAACGTC | GTGACTGGGA | AAACCCTGGC | GTTACCCAAC | TTAATCGCCT |
| 7441 | TGCAGCACAT | CCCCCTTTCG | CCAGCTGGCG | TAATAGCGAA | GAGGCCCGCA | CCGATCGCCC |
| 7501 | TTCCCAACAG | TTGCGCAGCC | TGAATGGCGA | ATGGGACGCG | CCCTGTAGCG | GCGCATTAAG |
| 7561 | CGCGGCGGGT | GTGGTGGTTA | CGCGCAGCGT | GACCGCTACA | CTTGCCAGCG | CCCTAGCGCC |
| 7621 | CGCTCCTTTC | GCTTTCTTCC | CTTCCTTTCT | CGCCACGTTC | GCCGGCTTTC | CCCGTCAAGC |
| 7681 | TCTAAATCGG | GGGCTCCCTT | TAGGGTTCCG | ATTTAGTGCT | TTACGGCACC | TCGACCCCAA |
| 7741 | AAAACTTGAT | TAGGGTGATG | GTTCACGTAG | TGGGCCATCG | CCCTGATAGA | CGGTTTTTCG |
| 7801 | CCCTTTGACG | TTGGAGTCCA | CGTTCTTTAA | TAGTGGACTC | TTGTTCCAAA | CTGGAACAAC |
| 7861 | ACTCAACCCT | ATCTCGGTCT | ATTCTTTTGA | TTTATAAGGG | ATTTTGCCGA | TTTCGGCCTA |
| 7921 | TTGGTTAAAA | AATGAGCTGA | TTTAACAAAA | ATTTAACGCG | AATTTTAACA | AAATATTAAC |
| 7981 | GCTTACAATT | TAGGTGGCAC | TTTTCGGGGA | AATGTGCGCG | GAACCCCTAT | TTGTTTATTT |
| 8041 | TTCTAAATAC | ATTCAAATAT | GTATCCGCTC | ATGAGACAAT | AACCCTGATA | AATGCTTCAA |

FIG. 17 (continued)

```
8101   TAATATTGAA AAAGGAAGAG TATGAGTATT CAACATTTCC GTGTCGCCCT TATTCCCTTT
8161   TTTGCGGCAT TTTGCCTTCC TGTTTTTGCT CACCCAGAAA CGCTGGTGAA AGTAAAAGAT
8221   GCTGAAGATC AGTTGGGTGC ACGAGTGGGT TACATCGAAC TGGATCTCAA CAGCGGTAAG
8281   ATCCTTGAGA GTTTTCGCCC CGAAGAACGT TTTCCAATGA TGAGCACTTT TAAAGTTCTG
8341   CTATGTGGCG CGGTATTATC CCGTATTGAC GCCGGGCAAG AGCAACTCGG TCGCCGCATA
8401   CACTATTCTC AGAATGACTT GGTTGAGTAC TCACCAGTCA CAGAAAAGCA TCTTACGGAT
8461   GGCATGACAG TAAGAGAATT ATGCAGTGCT GCCATAACCA TGAGTGATAA CACTGCGGCC
8521   AACTTACTTC TGACAACGAT CGGAGGACCG AAGGAGCTAA CCGCTTTTTT GCACAACATG
8581   GGGGATCATG TAACTCGCCT TGATCGTTGG GAACCGGAGC TGAATGAAGC CATACCAAAC
8641   GACGAGCGTG ACACCACGAT GCCTGTAGCA ATGGCAACAA CGTTGCGCAA ACTATTAACT
8701   GGCGAACTAC TTACTCTAGC TTCCCGGCAA CAATTAATAG ACTGGATGGA GGCGGATAAA
8761   GTTGCAGGAC CACTTCTGCG CTCGGCCCTT CCGGCTGGCT GGTTTATTGC TGATAAATCT
8821   GGAGCCGGTG AGCGTGGGTC TCGCGGTATC ATTGCAGCAC TGGGGCCAGA TGGTAAGCCC
8881   TCCCGTATCG TAGTTATCTA CACGACGGGG AGTCAGGCAA CTATGGATGA ACGAAATAGA
8941   CAGATCGCTG AGATAGGTGC CTCACTGATT AAGCATTGGT AACTGTCAGA CCAAGTTTAC
9001   TCATATATAC TTTAGATTGA TTTAAAACTT CATTTTTAAT TTAAAAGGAT CTAGGTGAAG
9061   ATCCTTTTTG ATAATCTCAT GACCAAAATC CCTTAACGTG AGTTTTCGTT CCACTGAGCG
9121   TCAGACCCCG TAGAAAAGAT CAAAGGATCT TCTTGAGATC CTTTTTTTCT GCGCGTAATC
9181   TGCTGCTTGC AAACAAAAAA ACCACCGCTA CCAGCGGTGG TTTGTTTGCC GGATCAAGAG
9241   CTACCAACTC TTTTTCCGAA GGTAACTGGC TTCAGCAGAG CGCAGATACC AAATACTGTT
9301   CTTCTAGTGT AGCCGTAGTT AGGCCACCAC TTCAAGAACT CTGTAGCACC GCCTACATAC
9361   CTCGCTCTGC TAATCCTGTT ACCAGTGGCT GCTGCCAGTG GCGATAAGTC GTGTCTTACC
9421   GGGTTGGACT CAAGACGATA GTTACCGGAT AAGGCGCAGC GGTCGGGCTG AACGGGGGGT
9481   TCGTGCACAC AGCCCAGCTT GGAGCGAACG ACCTACACCG AACTGAGATA CCTACAGCGT
9541   GAGCTATGAG AAAGCGCCAC GCTTCCCGAA GAGAGAAAGG CGGACAGGTA TCCGGTAAGC
9601   GGCAGGGTCG GAACAGGAGA GCGCACGAGG GAGCTTCCAG GGGGAAACGC CTGGTATCTT
9661   TATAGTCCTG TCGGGTTTCG CCACCTCTGA CTTGAGCGTC GATTTTTGTG ATGCTCGTCA
9721   GGGGGGCGGA GCCTATGGAA AAACGCCAGC AACGCGGCCT TTTTACGGTT CCTGGCCTTT
9781   TGCTGGCCTT TTGCTCACAT GTTCTTTCCT GCGTTATCCC CTGATTCTGT GGATAACCGT
9841   ATTACCGCCT TTGAGTGAGC TGATACCGCT CGCCGCAGCC GAACGACCGA GCGCAGCGAG
9901   TCAGTGAGCG AGGAAGCGGA AGAGCGCCCA ATACGCAAAC CGCCTCTCCC CGCGCGTTGG
9961   CCGATTCATT AATGCAGCTG GCACGACAGG TTTCCCGACT GGAAAGCGGG CAGTGAGCGC
10021  AACGCAATTA ATGTGAGTTA GCTCACTCAT TAGGCACCCC AGGCTTTACA CTTTATGCTT
10081  CCGGCTCGTA TGTTGTGTGG AATTGTGAGC GGATAACAAT TTCACACAGG AAACAGCTAT
10141  GACCATGATT ACGCCAAGCG CGCAATTAAC CCTCACTAAA GGGAACAAAA GCTGGAGCTG
10201  CAAGCTT
```

KIR 7.1 GENE THERAPY VECTORS AND METHODS OF USING THE SAME

CROSS-REFERENCE TO RELATED APPLICATIONS

This application is a national stage filing under 35 U.S.C. § 371 of International Application No. PCT/US2019/055635, filed Oct. 10, 2019, which claims benefit to U.S. Provisional Application No. 62/743,623 filed on Oct. 10, 2018, the contents of which are incorporated by reference in its entirety.

STATEMENT REGARDING FEDERALLY SPONSORED RESEARCH

This invention was made with government support under EY024995 awarded by the National Institutes of Health. The government has certain rights in the invention.

SEQUENCE LISTING

The content of the ASCII text file of the sequence listing named "960296_03962_ST25.txt" which is 34.2 kb in size was created on Oct. 9, 2019 and electronically submitted via EFS-Web herewith the application is incorporated herein by reference in its entirety.

INTRODUCTION

Leber congenital amaurosis (LCA) is an inherited pediatric form of blindness characterized by severe loss of vision at birth. Children with LCA may also exhibit a variety of other abnormalities including roving eye movements (nystagmus), deep-set eyes, sensitivity to bright light, and central nervous system abnormalities. Typically, within an infant's first few months of life, parents notice a lack of visual responsiveness and nystagmus. Although the retinas of infants with LCA appear normal, little (if any) activity is detected in the retina by electroretinography (ERG). By early adolescence, however, various changes in the appearance of retina may be detected including pigmentary changes in the retinal pigment epithelium (RPE) and the presence of constricted blood vessels.

LCA is typically passed through families in an autosomal recessive pattern of inheritance. Mutations in at least 21 genes that are expressed in the outer retinal photoreceptors and retinal pigment epithelium (RPE) have been associated with LCA. Within the last decade, autosomal recessive mutations in the human KCNJ13 gene (603203 on chromosome locus 2q37.1) have been identified in patients with a specific form of LCA known as LCA16. To date, LCA16 pathogenic allelic variants include c.158G>A (p.Trp53Ter), c.359T>C (p.Iso120Thr), c.458C>T (p.Thr153Iso), c.496C>T (p.Arg166Ter), and c.722T>C (p.Leu241Pro). In addition, the compound heterozygous KCNJ13 mutations c.314 G>T (p.Ser105Iso) and c.655C>T (p.G219Ter) are known to cause early-onset retinal dystrophy in an LCA patient[5]. An autosomal dominant KCNJ13 mutation, c.484C>T (p.Arg162Trp), causes early-onset blindness called snowflake vitreoretinal degeneration (SVD OMIM-193230).

The human KCNJ13 gene encodes an inward rectifying potassium channel—Kir7.1. The Kir7.1 protein is expressed in several human tissues including the cell apical processes of RPE, in which it modulates retinal function and health. The role of the Kir7.1 channel in other organs remains to be elucidated.

Although the role of Kir7.1 is beginning to be understood in conditions such as LCA16, there are no approved therapies to treat channelopathies or conditions associated with insufficient expression or function of the Kir7.1 protein. Accordingly, there is a need in the art for new therapies for treating such conditions.

SUMMARY

In one aspect of the present invention, gene therapy vectors are provided. The gene therapy vectors may include a promoter operably connected to a polynucleotide encoding a Kir7.1 polypeptide.

In another aspect, the present invention relates to therapeutic compositions. The therapeutic compositions may include any of the gene therapy vectors described herein and a pharmaceutically-acceptable carrier.

In a further aspect of the present invention, methods of treating a subject having a condition associated with insufficient expression or function of a Kir7.1 polypeptide are provided. The methods may include administering a therapeutically effective amount of any one of the gene therapy vectors described herein or any one of the therapeutic compositions described herein to the subject.

BRIEF DESCRIPTION OF THE DRAWINGS

The patent or patent application file contains at least one drawing in color. Copies of this patent or patent application publication with color drawings will be provided by the Office upon request and payment of the necessary fee.

(FIG. 1A) Illustration of a mature RPE cell (bright-field image) with the normal TGG sequence (SEQ ID NO:19). Family pedigree indicating sample origin. (FIG. 1N) Plot of the average phagosome count within a fixed 200 $\mu m^2$ area in the control and diseased iPSC-RPE cells after 4 hr of feeding and a subsequent 48-hr digestion period or after 1 day of feeding followed by 6 days of digestion.

(FIG. 2A) Plot of the average current-voltage (I/V) curve for Kir7.1 currents using normal external K+ (black) or high external Rb+ (light blue) in control iPSC-RPE cells. (FIG. 2N) Western blot analysis of Kir7.1 protein expression in LCA16 iPSC-RPE cells detected after gene augmentation by using anti-GFP antibody.

FIGS. 3A-3D show the phenotype of patient-derived iPSC-RPE cells. Comparison of electron micrograph of a control hiPSC-RPE cell (FIG. 3A) and an LCA16 hiPSC-RPE cell (FIG. 3B) showing normal columnar morphology with basal infoldings, large nuclei, mitochondria (m), melanosomes and intact apical membrane with extending processes (ap). Images of live control hiPSC-RPE (FIG. 3C) and patient-derived hiPSC-RPE (FIG. 3D) cells in x-y-z dimension showing POS (red) and nuclei (blue) imaged 6 days after feeding cells for 1 day with fluorescent-labeled bovine POS. More undigested red fluorescent POS particles are visible in LCA16 hiPSC-RPE cells.

FIGS. 4A-4D show that a subpopulation of hiPSC-RPE show rescue in membrane potential but not current amplitude. (FIG. 4A) I/V plot of average current response in a subgroup of LCA16 hiPSC-RPE cells in normal K+ Ringer's and high Rb+ Ringer's solution after treatment of cells with 100 μM NB84. (FIG. 4B) I/V plot showing K+ and Rb+ current response in LCA16 hiPSC-RPE after treatment with 500 μM NB84. (FIG. 4C) Average plot of membrane potential showing rescue of membrane potential to control levels after treatment of LCA16 hiPSC-RPE with 100 or 500 μM NB84. (FIG. 4D) Current amplitude plot clearly demonstrating no rescue in current amplitude after treatment with either 100 or 500 μM NB84.

FIGS. 5A-5D show read-through of Trp53Ter ectopically expressed in CHO cells. As in LCA16 hiPSC-RPE cells, transduced CHO cells showed inwardly rectifying Kir7.1 current activated by Rb+ only after treatment with NB84. (FIG. 5A) I/V plot of cells showing K+(black) and Rb+ (red) current after treatment with NB84 showing recovery of both current amplitude and membrane potential. (FIG. 5B) A group of NB84 treated cells showing somewhat linear I/V plot for K+ (black) and Rb+ (red) illustrating recovery of only membrane potential but not current amplitude. Comparison of average recovery of both current amplitude (FIG. 5C) and membrane potential (FIG. 5D) after treatment of Trp53Ter expressing CHO cells.

(FIG. 6A) Current recordings are shown as I/V plots. (FIG. 6B) On an expanded scale for x-axis, resting membrane potential shows negative shift with wild type protein making up only 20% of the protein expression. (FIG. 6C) Average plot of either normalized current amplitude (filled circles) or membrane potential (grey bar) as a function of increasing wild-type protein expression. Solid line is a best fit for distribution using equation shown in FIG. 6D. Half-maximum current was obtained with about 26% of the wild type protein expression. (FIG. 6D) Values of best fit curve indicating half maximal response and Hill Slope.

FIGS. 7A-7D show a comparison of the rescue of membrane potential across treatment modalities. (FIG. 7A) On an expanded scale of the x-axis, resting membrane potential of control (black) and LCA16 iPSC-RPE (red) showed a positive shift in I/V plot. (FIG. 7B) For the LCA16 iPSC-RPE cells (red trace), treatment with NB84 shifted the I/V-plot to negative (blue). (FIG. 7C) Plot of average I/V also showed a negative shift of resting potential after gene augmentation (green). (FIG. 7D) Bar graph comparison of resting membrane potential showed recovery of LCA16 iPSC-RPE to control level after treatment with NB84 or upon gene augmentation.

(FIG. 9B) Average higher Rb+ current (red trace) in W53X mutant expressing cells after gene augmentation. (FIG. 9C) Net increase in Rb+ permeability increased (Blue) through Kir7.1 channel after gene augmentation. (FIG. 9D) Complete recovery of resting membrane potential (RMP) after AAV-Kir7.1 transduction of W53X expressing cells represented as blue box. (FIG. 9E) Western blot results showing expression of full length protein product after gene augmentation in lane W53X+AAV (red band).

FIG. 10A-10B shows Kir7.1 expression (green) in W53X mutant line after gene augmentation through AAV-Kir7.1 (FIG. 10A). (FIG. 10B) A higher magnification image shows membrane localization of the Kir7.1 protein alongside membrane marker WGA-Alexa 594. In the lower panel is the line scan for red and green showing membrane marker and Kir7.1 co-localize.

(FIG. 14A) Injection control on WT mice and the cKO control mice depicting the RPE response functional after 8 weeks with PBS injection. (FIG. 14B) ERG response from the Kir7.1 cKO mice which showed no a-, b- and c-wave during the screening. Delivery of the Kir7.1 with lentivirus carrying either constitutive EF1a promoter or RPE specific VMD2 promoter failed to rescue the RPE function due to the severe phenotype as both RPE and photoreceptors were degenerated. (FIG. 14C) c-wave from RPE is recovered in the cKO mice, by subretinal delivery of lentivirus carrying kcnj13 gene driven by EF1a and VMD2 promoter, where the photoreceptors were not degenerated but had no response from the RPE cells during screening. (FIG. 14D), (FIG. 14E), (FIG. 14F) Representative optical coherence tomography (OCT) images showing the retinal structure from the control mice, cKO mice (no-a-,b-c-wave) with no recovery and c-wave recovered mice (a-, b- but no-c-wave) during screening and post 8 weeks after lentiviral gene delivery respectively.

(FIG. 15A) Graph representing the subset of mice that did not show c-wave recovery after injection of lentivirus carrying kcnj13 gene driven by EF1a and VMD2 promoter. (FIG. 15B), (FIG. 15C) Optical coherence tomography (OCT) image of cKO mice with no c-wave during screening shows intact retina but wanes after 8 weeks revealing the progressive nature of retina degeneration over time due to the lack of Kir7.1 protein in RPE cell. (FIG. 15D), (FIG. 15E) OCT images showing the retinal structure from cKO mice those having the response from photoreceptors (a- and b-wave) but lacking c-wave response from RPE. Injection of the lentivirus carrying the kcnj13 gene failed to restore c-wave, could be due to inefficiency of the RPE transduction or mutilation due to injection.

FIG. 16 depicts Table 2 and Table 3 demonstrating an exemplary AAV vector for the present invention containing specific components and a suitable exemplary sequence for the AAV vector comprising a RPE specific promoter and the Kir7.1 gene.

FIG. 17 depicts Table 5 and Table 6 demonstrating an exemplary lentiviral vector of the present invention, including the specific components and a suitable exemplary sequence for the lentiviral vector.

DETAILED DESCRIPTION

Figures 1A, 1B:
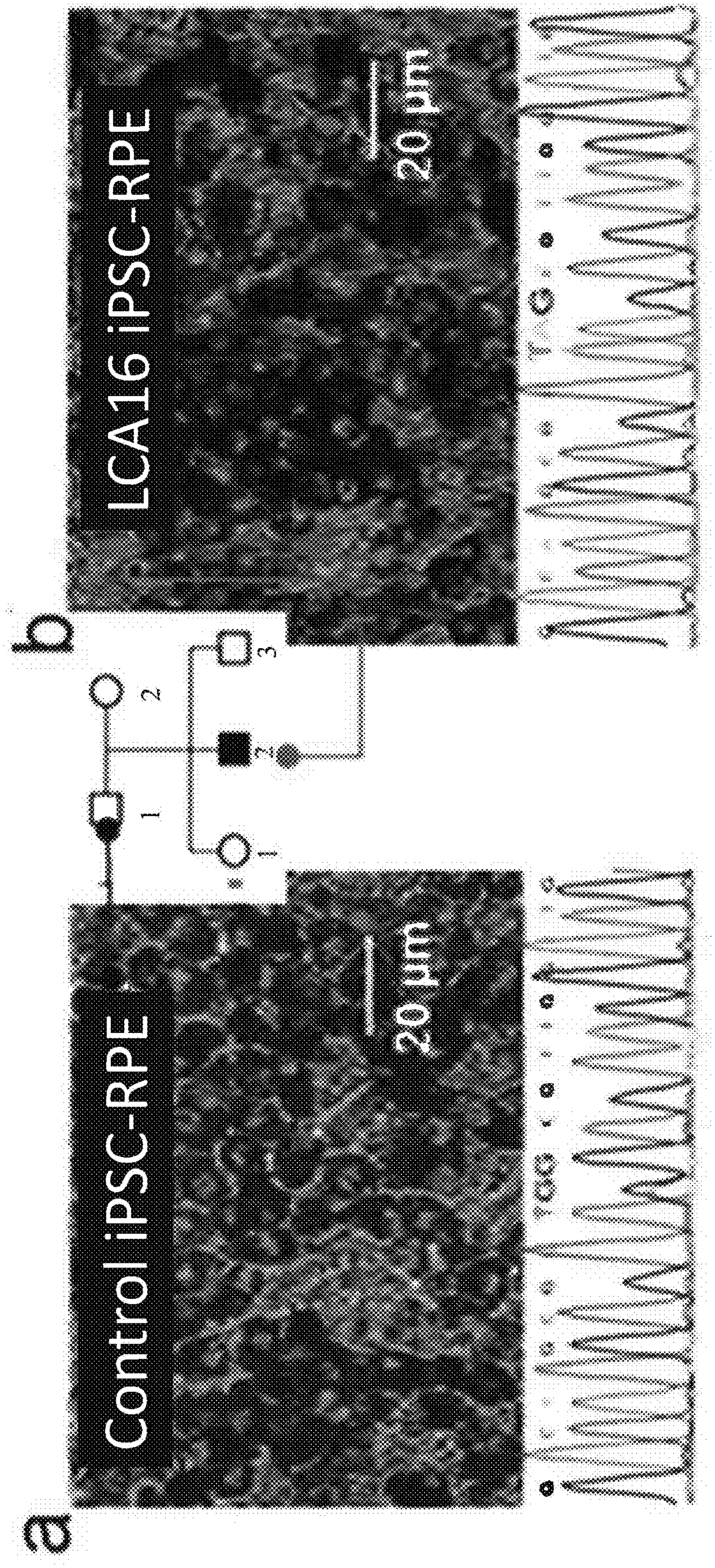
FIGS. 1A-1N show patient-derived iPSC-RPE with the LCA16 phenotype.
(FIG. 1B) Bright-field image of mature RPE cells derived from an LCA16 proband with the TAG sequence. (SEQ ID NO:20) (FIG. 1C) Normal karyotype in the patient sample with no clonal abnormalities.

Here, the present inventors disclose new gene therapy vectors and therapeutic compositions that may be used to treat Leber Congenital Amaurosis 16 (LCA16) or other conditions associated with insufficient expression or function of a Kir7.1 protein. In the non-limiting Examples, the inventors surprisingly show that a gene therapy approach may be used to effectively restore Kir7.1 polypeptide function in retinal pigment epithelium (RPE) cells either in vitro or in vivo resulting in RPE cells with rescued electrophysiological phenotypes. The inventors thus have discovered that gene therapy approaches may be used to effectively deliver the membrane protein Kir7.1. The present inventors demonstrate in part that expression of a Kir7.1 protein open reading frame alone is sufficient to get the Kir7.1 protein trafficked to the proper subcellular compartment. These results provide hope for potential curative therapeutics to treat Leber Congenital Amaurosis 16 (LCA16) or other conditions associated with insufficient expression or function of a Kir7.1 protein.

Gene Therapy Vectors

In one aspect of the present invention, gene therapy vectors are provided. The gene therapy vectors may include a promoter operably connected to a polynucleotide encoding a Kir7.1 polypeptide. The general approach in certain aspects of the present invention is to provide a cell with an expression construct encoding a Kir7.1 polypeptide, thereby permitting the expression of the Kir7.1 polypeptide in the cell. Following delivery of the expression construct, the Kir7.1 polypeptide encoded by the expression construct is synthesized by the transcriptional and translational machinery of the cell.

As used herein, an "expression construct encoding a Kir7.1 polypeptide" refers to a promoter operably connected to a polynucleotide encoding a Kir7.1 polypeptide.

As used herein, the terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of natural or synthetic origin (which may be single-stranded or double-stranded and may represent the sense or the antisense strand). In some embodiments, the promoters and Kir7.1 polynucleotides or expression constructs encoding a Kir7.1 polypeptide described herein are encoded in double-stranded DNA, single-stranded DNA, or RNA.

As used herein, a "gene therapy vector" refers to viral or non-viral vector systems that may be used to deliver an expression construct encoding a Kir7.1 polypeptide into a cell (i.e., eukaryotic cell). Both broad types of vector systems are described in the following sections. There also are two primary approaches utilized in the delivery of an expression construct for the purposes of gene therapy; either indirect, ex vivo methods or direct, in vivo methods. Ex vivo gene transfer comprises vector modification of (host) cells in culture and the administration or transplantation of the vector modified cells to a gene therapy recipient. In vivo gene transfer comprises direct introduction of the vector (e.g., injection, inhalation) into the target source or therapeutic gene recipient.

In certain embodiments of the invention, the expression construct encoding the Kir7.1 polypeptide may be stably integrated into the genome of the cell. In yet further embodiments, the expression construct encoding the Kir7.1 polypeptide may be stably or transiently maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and/or where in the cell the nucleic acid remains is dependent on the type of vector employed. The following gene delivery methods provide the framework for choosing and developing the most appropriate gene delivery system for a preferred application.

Non-Viral Gene Therapy Vectors

In some embodiments, the gene therapy vector may be a delivery particle. Delivery particles suitable for delivering polynucleotides are known in the art and may include, without limitation, polymeric particles, liposomal particles, and particles including lipids and at least one type of polymer. In some embodiments, the delivery particles may be formed using common Lipofectamine reagents.

The delivery particles may include nanoscale particles and/or microscale particles, for example, as delivery vehicles of components to a cell for genome editing. The particles may have an effective average diameter less than about 500 μm, 100 μm, 50 μm, 20 μm, 10 μm, 5 μm, 2 μm, 1 μm, 0.5 μm, 0.2 μm, 0.1 μm, 0.05 μm, 0.02 μm, 0.01 μm, or have an effective average diameter within a range bounded by any of 500 μm, 100 μm, 50 μm, 20 μm, 10 μm, 5 μm, 2 μm, 1 μm, 0.5 μm, 0.2 μm, 0.1 μm, 0.05 μm, 0.02 μm, 0.01 μm (e.g., 0.01-5 μm). The nanoscale particles and microscale particles may be referred to as "nanoparticles" and "microparticles," respectively.

Polymeric particles have been described in the art. (U.S. Patent Publication 20140066388). Polymeric particles may include or may be formed from biodegradable polymeric molecules, which in some embodiments may include dendrimers. Suitable dendrimers may include, but are not limited to, polyamidoamine (PAMAM) dendrimers. Polyamidoamine dendrimers have been used in the art as vehicles for intracellular delivery of therapeutics. Polyamidoamine dendrimers suitable for preparing the presently disclosed nanoparticles may include 3rd-, 4th-, 5th-, or preferably at least 6th-generation dendrimers.

Polymeric particles may also include or may be formed from other biodegradable polymeric molecules which may include, without limitation, polylactic acid (PLA), polygycolic acid (PGA), co-polymers of PLA and PGA (e.g., polyactic-co-glycolic acid (PLGA)), poly-ε-caprolactone (PCL), polyethylene glycol (PEG), poly(3-hydroxybutyrate), poly(p-dioxanone), polypropylene fumarate, poly (orthoesters), polyol/diketene acetals addition polymers, poly-alkyl-cyano-acrylates (PAC), poly(sebacic anhydride) (PSA), poly(carboxybiscarboxyphenoxyphenoxy hexone (PCPP) poly[bis(p-carboxypheonoxy)methane](PCPM), copolymers of PSA, PCPP and PCPM, poly(amino acids), poly(pseudo amino acids), polyphosphazenes, derivatives of poly[(dichloro)phosphazenes] and poly[(organo)phosphazenes], poly-hydroxybutyric acid, or S-caproic acid, elastin, gelatin, and chitosan. (See, e.g., Kumari et al., Colloids and Surfaces B: Biointerfaces 75 (2010) 1-18; and U.S. Pat. Nos. 6,913,767; 6,884,435; 6,565,777; 6,534,092; 6,528,087; 6,379,704; 6,309,569; 6,264,987; 6,210,707; 6,090,925; 6,022,564; 5,981,719; 5,871,747; 5,723,269; 5,603,960; and 5,578,709; and U.S. Published Application No. 2007/0081972; and International Application Publication Nos. WO 2012/115806; and WO 2012/054425). In some embodiments, the particles may include a mixture of PLGA and PAMAM.

Polymeric particles may be prepared by methods known in the art. (International Application Publication Nos. WO 2012/115806; and WO 2012/054425). Suitable methods for preparing the nanoparticles may include methods that utilize a dispersion of a preformed polymer, which may include but are not limited to solvent evaporation, nanoprecipitation, emulsification/solvent diffusion, salting out, dialysis, and supercritical fluid technology. In some embodiments, the nanoparticles may be prepared by forming a double emulsion (e.g., water-in-oil-in-water) and subsequently performing solvent-evaporation. The nanoparticles obtained by the disclosed methods may be subjected to further processing steps such as washing and lyophilization, as desired. Optionally, the nanoparticles may be combined with a preservative (e.g., trehalose).

Micelle and liposomal-based particles may also serve as suitable delivery particles. See, e.g., U.S. Pat. No. 8,252,324. Micelles are self-assembling spherical colloidal nanoparticles formed by amphiphilic molecules. Micelles are also described as aggregate surfactant molecules disbursed in a liquid colloid. The core of the micelle, which is segregated in an aqueous milieu, is capable of encapsulating polynucleotides and/or proteins protecting them from destruction and biological surroundings while improving their pharmacokinetics and biodistribution. Micelles are generally in the order of 5-50 nm in diameter, and are therefore capable of accumulating in pathological areas with leaky vasculature, such as infarct zones and tumors due to the enhanced permeability and retention effect. Micelles are also capable of evading a major obstacle in drug targeting by particulate systems: non-specific uptake by the reticuloendothelial systems and renal secretion. In contrast to micelles, liposomes are bilayered phospholipid vesicles approximately 50 to 1,000 nm in diameter. Liposomes are biologically inert and completely biocompatible; they cause practically no toxic or antigenic reactions. Polynucleotides included in liposomes are protected from the destructive action of the external media by the liposomes. Thus, liposomes are able to deliver their content inside cells and even inside different cell compartments. Generally, liposomes are considered a promising carrier with significant therapeutic potential, as demonstrated in numerous laboratory tests and clinical trials.

Delivery particles may also include particles including lipids and polymer components. For example, particles including a phospholipid bilayer and poly(beta-amino ester) (PBAE) have been developed for the in vivo delivery of polynucleotides.

The delivery particles preferably have physical properties that facilitate uptake by a targeted cell. For example, preferably the particles have a size and a charge that facilitate uptake by a targeted cell. Typically, the particles have a mean effective diameter of less than 1 micron, and preferably the particles have a mean effective diameter of between about 25 nm and about 500 nm, and more preferably between about 50 nm and about 250 nm, and most preferably about 100 nm to about 150 nm. The size of the particles (e.g., mean effective diameter) may be assessed by known methods in the art, which may include but are not limited to transmission electron microscopy (TEM), scanning electron microscopy (SEM), Atomic Force Microscopy (AFM), Photon Correlation Spectroscopy (PCS), Nanoparticle Surface Area Monitor (NSAM), Condensation Particle Counter (CPC), Differential Mobility Analyzer (DMA), Scanning Mobility Particle Sizer (SMPS), Nanoparticle Tracking Analysis (NTA), X-Ray Diffraction (XRD), Aerosol Time of Flight Mass Spectroscopy (ATFMS), and Aerosol Particle Mass Analyzer (APM).

Delivery particles will be taken up by cells non-specifically even if the particles do not include a specific ligand on their surface. However, the disclosed delivery particles may be configured to also include a ligand that specifically targets a particular cell type. In order to achieve more specific targeting of delivery particles, such particles may be modified with various ligands using advanced conjugation procedures. For example, antibodies and small peptides have been attached to the water exposed tips of polyethyleneglycol chains. Antibodies and small peptides have also been conjugated via reactive p-nitrophenylcarbonyl, N-benzotrazole carbonyl or maleimide terminated PEG-phosphatidylethanolamine.

Viral Gene Therapy Vectors

The gene therapy vector may also be a viral vector. The viral vector may be a virus particle or may be encoded on a DNA plasmid. In some embodiments where the viral vector is a virus particle, for example a lentivirus viral particle, the virus particle may include a VSV-G envelop protein. The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of human diseases. The various viral vectors described below present specific advantages and disadvantages depending on the particular gene-therapeutic application.

Suitable viral vectors that may be used in accordance with the present invention may include, without limitation, retroviral vectors, adeno-associated viral (AAV) vectors, adenoviral vectors, or herpes-simplex vectors. Retroviral vectors may include, for example, lentiviral vectors.

Here, in the non-limiting Examples, the present inventors demonstrate that a polynucleotide encoding a Kir7.1 polypeptide could successfully be introduced and expressed in retinal pigment epithelium (RPE) cells either in vitro or in vivo using either lentiviral or adeno-associated viral (AAV) vectors so as to rescue functional defects in a KCNJ13 gene. Accordingly, in some embodiments, the viral vector may be a lentiviral vector or an AAV, suitably an AAV2, vector. The AAV vectors described herein may further include at least one, two, three, four, five, six, seven, or eight of the components listed in Table 2 or Table 3. The lentiviral vectors described herein may further include at least one, two, three, four, five, six, seven, eight, nine, ten, eleven, twelve, thirteen, fourteen, or fifteen of the components listed in Table 5 or Table 6.

Retroviral Vectors

In certain embodiments of the invention, the use of retroviruses for gene delivery of the Kir7.1 expression construct is contemplated. Retroviruses or retroviral vectors are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

Lentiviral vectors are a type of retrovirus that can infect both dividing and nondividing cells. Lentiviruses can be used to provide highly effective gene therapy as lentiviruses can change the expression of their target cell's gene for up to six months. They can be used for nondividing or terminally differentiated cells such as neurons, macrophages, hematopoietic stem cells, retinal photoreceptors, and muscle and liver cells, cell types for which previous gene therapy methods could not be used.

Adeno-Associated Viral (AAV) Vectors

Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. AAV ITRs may be derived from any of several AAV serotypes, including AAV1, AAV2, AAV3, AAV4, AAV5, AAV6, AAV7, AAV8, AAV9, AAV10, AAV11, avian AAVs, bovine AAVs etc. The 5' and 3' ITRs of the AAV viral vectors disclosed herein may be derived from any of these AAV serotypes. The 5' and 3' ITRs which flank the AAV viral vectors disclosed herein need not necessarily be identical or derived from the same AAV serotype. Thus, rAAV vector design and production allow for exchanging the capsid proteins between different AAV serotypes. Homologous vectors comprising an expression cassette flanked by e.g., AAV2-ITRs and packaged in an AAV2 capsid, can be produced as well as heterologous, hybrid vectors where the transgene expression cassette is flanked by e.g., AAV2 ITRs, but the capsid originates from another AAV serotype such as AAV5 for example. Suitably, in some embodiments, the present inventors have found that AAV2 viral vectors may be used to effectively deliver Kir7.1 expression constructs into cells.

The internal non-repeated portion of the AAVgenome includes two large open reading frames, known as the AAV replication (rep) and capsid (cap) genes. The rep and cap genes code for viral proteins that allow the virus to replicate and package the viral genome into a virion. A family of at least four viral proteins is expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus. Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

Suitable AAV vectors are known in the art. For example, suitable AAV vectors include AAV2/5, demonstrated in "AAV2/5-mediated gene therapy in iPSC-derived retinal pigment epithelium of a choroideremia patient", incorporated by reference in its entirety. See, e.g., Cereso et. al. Mol Ther Methods Clin Dev. 2014. Further examples of AAV vectors that can suitably be adapted for the present gene delivery can be found in "Comparative AAV-eGFP Transgene Expression Using Vector Serotypes 1-9, 7m8, and 8b in Human Pluripotent Stem Cells, RPEs, and Human and Rat Cortical Neurons." See Duong et.al. Stem Cells Int. 2019.

Adenoviral Vectors

In particular embodiments, an adenoviral vector is contemplated for the delivery of Kir7.1 expression constructs. "Adenoviral vector" is meant to include those constructs containing adenovirus sequences sufficient to (a) support packaging of the construct and (b) to ultimately express construct that has been cloned therein.

Adenoviruses comprise linear double stranded DNA, with a genome ranging from 30 to 35 kb in size. An adenoviral vector according to the present invention comprises a genetically engineered form of the adenovirus. Advantages of adenoviral gene transfer include the ability to infect a wide variety of cell types, including non-dividing cells, a mid-sized genome, ease of manipulation, high infectivity and they can be grown to high titers. Further, adenoviral infection of host cells does not result in chromosomal integration because adenoviral DNA can replicate in an episomal manner, without potential genotoxicity associated with other viral vectors. Adenoviruses also are structurally stable and no genome rearrangement has been detected after extensive amplification. An exemplary adenoviral vector according to the present invention is replication defective vector that will not have an adenovirus E1 region. Adenovirus growth and manipulation is known to those of skill in the art, and exhibits broad host range in vitro and in vivo. See, e.g., U.S. Pat. Nos. 5,670,488; 5,932,210; 5,824,544.

Herpes-Simplex Viral Vectors

Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cell types. For use in therapeutic gene delivery, HSV must be rendered replication-defective. Protocols for generating replication-defective HSV helper virus-free cell lines have been described (U.S. Pat. Nos. 5,879,934; 5,851,826, each specifically incorporated herein by reference in its entirety).

Other Viral Vectors

The development and utility of viral vectors for gene delivery is constantly improving and evolving. Other viral vectors such as poxvirus; e.g., vaccinia virus, alpha virus; e.g., sindbis virus, Semliki forest virus, reovirus and influenza A virus are contemplated for use in the present invention and may be selected according to the requisite properties of the target system.

Promoters

As used herein, the terms "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the promoter is specific to the cell type in which Kir7.1 is to be expressed. For example, suitable cell types including retinal pigment epithelium, small intestinal cells, uterine cells, kidney cells, among others. The promoters may be specific to polarized cells, e.g., cells that have directionality and the Kir7.1 potassium pump plays a role in maintaining the polarization of the cells. Suitable promoters that may be used in a tissue specific manner include the RPE promoters (e.g., EF1a or VMD2) described and the promoters found below in Table 7. In some embodiments, the promoter is active in the retinal pigment epithelium (RPE) in the eye of a subject.

The "promoter" may be the endogenous promoter for the KCNJ13 gene found, for example, in a subject. Alternatively, the promoter may be a heterologous promoter (i.e., a promoter for a non-KCNJ13 gene). Heterologous promoters useful in the practice of the present invention include, without limitation, constitutive, inducible, temporally-regulated, developmentally regulated, chemically regulated, tissue-preferred and tissue-specific promoters.

Suitable heterologous promoters may include, without limitation, an EF1a promoter or a VMD2 promoter. An exemplary EF1a promoter is provided as SEQ ID NO: 3. An exemplary VMD2 promoter is provided as SEQ ID NO: 4. Suitable EF1a promoters may also include variants of the EF1a promoter provided as SEQ ID NO: 3 having at least 60%, 65%, 70%, 75%, 80%, 85%, 90%, 91%, 92%, 93%, 94%, 95%, 96%, 97%, 98%, 99%, or 100% sequence identity to SEQ ID NO: 3. Suitable VMD2 promoters may also include variants of the VMD2 promoter provided as SEQ ID NO: 4 having at least 60%, 65%, 70%, 75%, 80%, 85%, 90%, 91%, 92%, 93%, 94%, 95%, 96%, 97%, 98%, 99%, or 100% sequence identity to SEQ ID NO: 4.

Regarding polynucleotides such the promoters and Kir7.1 polynucleotides described herein, the phrases "% sequence identity," "percent identity," or "% identity" refer to the percentage of base matches between at least two polynucleotide sequences aligned using a standardized algorithm. Methods of polynucleotide sequence alignment are well-known.

In some embodiments, the disclosed polynucleotides encoding a Kir7.1 polypeptide are operably connected to the promoter. As used herein, a polynucleotide is "operably connected" or "operably linked" when it is placed into a functional relationship with a second polynucleotide sequence. For instance, a promoter is operably linked to a polynucleotide if the promoter is connected to the polynucleotide such that it may effect transcription of the polynucleotides. In various embodiments, the polynucleotides may be operably linked to at least 1, at least 2, at least 3, at least 4, at least 5, or at least 10 promoters.

As used herein, a "Kir7.1 polypeptide" refers to an inward rectifier potassium channel characterized by a greater tendency to allow potassium to flow into the cell rather than out of it. A human Kir7.1 polypeptide is provided as SEQ ID NO: 1. A Kir7.1 polypeptide may also be a variant or homolog of the human Kir7.1 polypeptide provided as SEQ ID NO: 1 having at least 60%, 65%, 70%, 75%, 80%, 85%, 90%, 91%, 92%, 93%, 94%, 95%, 96%, 97%, 98%, 99%, or 100% sequence identity to SEQ ID NO: 1.

As used herein, the terms "protein" or "polypeptide" or "peptide" may be used interchangeably to refer to a polymer of amino acids. A "polypeptide" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

Regarding Kir7.1 polypeptides, the phrases "% sequence identity," "percent identity," or "% identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The Kir7.1 polypeptides disclosed herein may include "variant" polypeptides, "mutants," and "derivatives thereof." As used herein the term "wild-type" is a term of the art understood by skilled persons and means the typical form of a polypeptide as it occurs in nature as distinguished from variant or mutant forms. As used herein, a "variant, "mutant," or "derivative" refers to a polypeptide molecule having an amino acid sequence that differs from a reference protein or polypeptide molecule. A variant or mutant may have one or more insertions, deletions, or substitutions of an amino acid residue relative to a reference molecule. For example, a Kir7.1 polypeptide mutant or variant may have one or more insertions, deletions, or substitution of at least one amino acid residue relative to the Kir7.1 "wild-type" polypeptides disclosed herein. The polypeptide sequence of a "wild-type" Kir7.1 polypeptides is provided as SEQ ID NO: 1. This sequence may be used as a reference sequence.

The Kir7.1 polypeptides provided herein may be full-length polypeptides or may be fragments of the full-length polypeptide. As used herein, a "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 350 contiguous amino acid residues of a reference polypeptide, respectively. In some embodiments, a fragment may comprise at least 5, 10, 15, 20, 25, 30, 40, 50, 60, 70, 80, 90, 100, 150, or 250 contiguous amino acid residues of a reference polypeptide. Fragments may be preferentially selected from certain regions of a molecule. The term "at least a fragment" encompasses the full length polypeptide. A fragment of a Kir7.1 polypeptide may comprise or consist essentially of a contiguous portion of an amino acid sequence of a full-length Kir7.1 polypeptide (See SEQ ID NO: 1). A fragment may include an N-terminal truncation, a C-terminal truncation, or both truncations relative to the full-length Kir7.1 polypeptide.

A "deletion" in a Kir7.1 polypeptide refers to a change in the amino acid sequence resulting in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a Kir7.1 polypeptide refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of a Kir7.1 polypeptide may have N-terminal insertions, C-terminal insertions, internal insertions, or any combination of N-terminal insertions, C-terminal insertions, and internal insertions.

The amino acid sequences of the Kir7.1 polypeptide variants, mutants, derivatives, or fragments as contemplated herein may include conservative amino acid substitutions relative to a reference amino acid sequence. For example, a variant, mutant, derivative, or fragment polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed variant and fragment Kir7.1 polypeptides described herein may have one or more functional or biological activities exhibited by a reference polypeptide (e.g., one or more functional or biological activities exhibited by a wild-type Kir7.1 polypeptide (i.e, SEQ ID NO: 1). Suitably, the disclosed variant or fragment Kir7.1 polypeptide retains at least 20%, 40%, 60%, 80%, or 100% of the potassium conductance properties of the reference polypeptide. As used herein, a "functional fragment" of a Kir7.1 polypeptide is a fragment of, for example, the polypeptide of SEQ ID NO: 1 that retains at least 20%, 40%, 60%, 80%, or 100% of the potassium conductance properties of the full-length ADH polypeptide.

Furthermore, it will be readily apparent to a person of ordinary skill in the art that additional Kir7.1 polypeptide variants may be created by aligning Kir7.1 polypeptide sequences from two or more species. Based on these alignments, a person of ordinary skill in the art may identify various amino acid residues that may be altered (i.e. substituted, deleted, etc.) without substantially affecting the potassium conductance properties of the polypeptide. For example, a person of ordinary skill in the art would appreciate that substitutions in a reference Kir7.1 polypeptide could be based on alternative amino acid residues that occur at the corresponding position in other Kir7.1 polypeptides from other species.

In some embodiments, the gene therapy vector may be a lentiviral vector or adeno-associated viral (AAV) vector including a polynucleotide having at least 60%, 65%, 70%, 75%, 80%, 85%, 90%, 91%, 92%, 93%, 94%, 95%, 96%, 97%, 98%, 99%, or 100% sequence identity sequence identity to SEQ ID NO: 5 (EF1a-Kir7.1) or SEQ ID NO: 6 (VMD2-Kir7.1).

Therapeutic Compositions

In another aspect, the present invention relates to therapeutic compositions. The therapeutic compositions may include any of the gene therapy vectors described herein and a pharmaceutically-acceptable carrier. The therapeutic compositions may include a pharmaceutically-acceptable carrier, excipient, or diluent, which are nontoxic to the cell or subject being exposed thereto at the dosages and concentrations employed. Often a pharmaceutical diluent is in an aqueous pH buffered solution. Examples of pharmaceutically-acceptable carriers or excipients may include, without limitation, water, buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

Methods of Treatment

In a further aspect of the present invention, methods of treating a subject having a condition associated with insufficient expression or function of a Kir7.1 polypeptide are provided. The methods may include administering a therapeutically effective amount of any one of the gene therapy vectors described herein or any one of the therapeutic compositions described herein to the subject. As used herein, the terms "subject" and "patient" are used interchangeably to refer to both human and nonhuman animals. The term "nonhuman animals" of the disclosure may include mammals and non-mammals, such as nonhuman primates, sheep, dog, cat, horse, cow, pig, mice, rats, and the like. In some embodiments, the subject is a human patient. The subject may be a human patient having cells (i.e., RPE cells) that exhibit insufficient expression or function of a Kir7.1 polypeptide.

Conditions associated with insufficient expression or function of a Kir7.1 polypeptide may include conditions in which a subject has reduced or eliminated Kir7.1 expression or function in or outside a cell as compared to a control. As used herein, a "control" may include subjects having wild-type Kir7.1 function. For example, in some embodiments, a control may be a subject having a wildtype KCNJ13 gene that does not include any loss-of-function mutations in either the non-coding regulatory sequences (i.e., promoter, enhancers, etc.) controlling the expression of the KCNJ13 gene or in the coding region of the KCNJ13 gene (i.e., SEQ ID NOS: 1 and 2).

Subjects may have several "cell" types that may display insufficient expression or function of a Kir7.1 polypeptide. As used herein, a "cell" may refer to cells that normally express a Kir7.1 polypeptide in a wild-type subject. Suitable cells may include, without limitation, eye cells such as retinal cells or retinal pigment epithelium (RPE) cells. Kir7.1 is also expressed in epithelial cells of various organs including kidney, thyroid, CNS neurons, ependymal cells, choroid plexus epithelium, spinal cord, myometrial smooth muscle, small intestine, neural regions of the gastric mucosa as well as gastric parietal cells, and also in the lung, prostate, liver, pancreas, cochlear nucleus, testis and ovaries.

In some embodiments, the condition associated with insufficient expression or function of a Kir7.1 polypeptide may be associated with at least one loss-of-function mutation in a KCNJ13 gene. The human KCNJ13 gene is provided as UniProt 060928. The KCNJ13 gene in other non-human subjects may be identified by using homology searching methods well known in the art. Suitable loss-of-function mutations in the KCNJ13 gene may include at least one substitution to the Kir7.1 protein provided as SEQ ID NO: 1 selected from the group consisting of W53Ter, Q116R, I120T, T153I, R162Q, R166Ter, L241P, E276A, S105I, and G219Ter. In some embodiments, the condition associated with insufficient expression or function of a Kir7.1 polypeptide may be, without limitation, Leber Congenital Amaurosis 16 (LCA16), retinitis pigmentosa, or Snowflake Vitreoretinal Degeneration (SVD).

In some embodiments, the cell that displays insufficient expression or function of a Kir7.1 polypeptide is within the small intestine of the subject. Suitable vectors may be constructed using a small intestine specific promoter, including, but not limited to, for example, HIFABP, HMUC2, or HLY (found in Table 7) to target the Kir7.1 to the small intestine. Methods of treating a subject with insufficient expression or function of Kir7.1 in the small intestine are provided. The method may include administering a therapeutically effective amount of a gene therapy vector comprising a small intestine specific promoter, e.g., HIFABP, HMUC2, or HLY operably linked to the Kir7.1 polynucleotide or a therapeutic composition comprising the vector to the subject in order to provide expression of Kir7.1 in the small intestine of the subject.

In some embodiments, the cell the displays insufficient expression or function of a Kir7.1 polypeptide within the uterus of a subject. Suitable vectors may be constructed using a smooth muscle specific promoter, for example, SM22a (found in Table 7) to target the Kir7.1 to the uterus. Methods of treating a subject with insufficient expression or function of Kir7.1 in the uterus are provided. The method may include administering a therapeutically effective amount of a gene therapy vector comprising a smooth muscle or uterus specific promoter, e.g., SM22a operably linked to the Kir7.1 polynucleotide or a therapeutic composition comprising the vector to the subject in order to provide expression of Kir7.1 in the uterus. This method may allow for controlling uterine contractions by regulating Kir7.1 expression and/or regulating the potassium balance within smooth muscles of the uterus.

In some embodiment, the cell that displays insufficient expression or function of a Kir7.1 polypeptide is within the kidney of a subject. Suitable promoters that result in kidney specific expression include, but are not limited to, for example, KAP (kidney androgen-regulated protein or NPHS2 (podocin) promoter (See Table 7). Methods of treating a subject having a condition associated with insufficient expression or function of a Kir7.1 polypeptide within the kidney are provided. The methods may include administering a therapeutically effective amount of a gene therapy vector comprising a kidney specific promoter (e.g., KAP or NPHS2) operably linked to the Kir7.1 polynucleotide sequence or a therapeutic composition comprising such vector to the subject in order to express Kir7.1 in the kidney of the subject.

TABLE 7

Promoters specific to cell types.

| Organ | Promoter | GenBank Accession No: Primers for | Reference |
| --- | --- | --- | --- |
| Small Intestine | HIFABP (human intestinal fatty acid binding protein promoter)<br>HMUC2 (human mucin-2 promoter)<br>HLY (human lysozyme promoter) | NG_011444<br>(Primers to amplify promoter by PCR for cloning)<br>A: 5'-CCGCTCGAGTACCTTCCAAGTGCTGTCAAAC-3' (SEQ ID NO: 11)<br>S: 5'-CGACGCGTCATGCTGAATTCCTTAATTTGC-3' (SEQ ID NO: 12)<br>U67167<br>S: 5'-CTAGCTAGCTCCTCCCAGCGTAACGTGAGC-3'- (SEQ ID NO: 13)<br>A: 5'-GAAGATCTCTAGTGGCAGCCCCATGGTG-3'- (SEQ ID NO: 14)<br>NM_000239<br>S: 5'-CTAGCTAGCCTGTCCTCTTAGGCAGATACAGA-3' (SEQ ID NO: 15)<br>A: 5'-GAAGATCTAGAGCCTTCATGTTGACTGCTA-3' (SEQ ID NO: 16) | Identification of an intestine-specific promoter and inducible expression of bacterial α-galactosidase in mammalian cells by a lac operon system. Ya-Feng et. al. J Anim Sci Biotechnol. 2012 |
| Uterus | SM22a | Z68618 | Temporally controlled somatic mutagenesis in smooth muscle. Kühbandner et. al. Genesis. 2000 |
| Kidney | KAP (kidney androgen-regulated protein)<br>NPHS2 (podocin) | 5'-flanking region of the KAP gene (−1542 to −466) 16483<br>NPHS2 gene (GenBank accession number AF487463<br>Sequencing of NPHS2 promoter from −628 to ATG was done by PCR two primers:<br>forward 5'-GAAAGTTGGGGATGAGGCGA-3'; (SEQ ID NO: 17)<br>reverse 5'-CAATCAAAGCTTCCTCAGAGCTGCCGGGCGGCT-3'. (SEQ ID NO: 18) | The kidney androgen-regulated protein promoter confers renal proximal tubule cell-specific and highly androgen-responsive expression on the human angiotensinogen gene in transgenic mice.<br>Ding Y et. al. J Biol Chem. 1997<br>Rare functional variants of podocin (NPHS2) promoter in patients with nephrotic syndrome.<br>Oleggini et. al. Gene Expr. 2006 |

"Treating" the condition associated with insufficient expression or function of a Kir7.1 polypeptide includes, without limitation, increasing the levels of functional Kir7.1 polypeptide in or outside a cell in a subject. It would be understood by one skilled in the art that an increase in the amount of functional Kir7.1 may only need to be an increase of at least about 10%, preferably at least about 20%, alternatively about 30%, which may result in the proper functioning of the potassium channel within the cell in which it is expressed, leading to alleviation of one or more symptoms of the disease. For example, the ratio of functional to nonfunctional Kir7.1 within the cell needs to be sufficient to allow for proper functioning of the potassium channel, and may vary depending of cell type and location.

A "therapeutically effective amount" or an "effective amount" as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions (i.e. gene therapy vectors and/or therapeutic compositions) described herein may be administered by any means known to those skilled in the art, including, without limitation, locally or systemically, including, for example, intraocularly, topically, intranasally, intramuscularly, or subcutaneously. When administered intraocularly, in some embodiments, the compositions (i.e. gene therapy vectors and/or therapeutic compositions) may be administered subretinally by, for example, injection to at least one retina of the subject. In the retina, the targeted region for delivery of the compositions (i.e. gene therapy vectors and/or therapeutic compositions) may include the central superior retina or macula.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological or prophylactic protocol. The maximal dosage for a subject is the highest dosage that does not cause undesirable or intolerable side effects. The number of variables in regard to an individual treatment regimen is large, and a considerable range of doses is expected. The route of administration will also impact the dosage requirements.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The compositions (i.e. gene therapy vectors and/or therapeutic compositions) described herein may be administered one or more times to the subject to effectively increase the levels of functional Kir7.1 polypeptide in or outside a cell in a subject. The compositions (gene therapy vectors or therapeutic compositions) may be administered based on the number of copies of the expression construct encoding a Kir7.1 polypeptide delivered to the subject. The subject may be administered between $10^6$ and $10^{14}$, or between $10^8$ and $10^{12}$, or between $10^9$ and $10^{11}$, or any range therein copies. In embodiments where the gene therapy vector is a viral vector, the subject may be administered between $10^6$ and $10^{14}$, or between $10^8$ and $10^{12}$, or between $10^9$ and $10^{11}$, or any range therein viral genomes.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—A Precision Medicine Cure for Mutation-Specific Blindness

Leber Congenital Amaurosis (LCA) is an inherited pediatric blindness that is associated with at least 21 different genes. We used patient-derived iPSC-RPE cells to reveal the molecular mechanisms underlying LCA16, which is due to a nonsense mutation in the KCNJ13 gene resulting in a nonfunctional Kir7.1 ion channel. Using either read-through or gene augmentation, we rescued Kir7.1 channel function in patient-derived iPSC-RPE cells via a precision medicine approach.

Mutations in at least 21 genes that are expressed in the outer retinal photoreceptors and retinal pigment epithelium (RPE) cause a form of inherited blindness known as Leber Congenital Amaurosis (LCA), from birth and early childhood. Within the last decade, autosomal recessive mutations in the KCNJ13 gene (603203 on chromosome locus 2q37.1) have been identified in patients with an LCA phenotype (LCA16 OMIM-614186, the 16$^{th}$ gene shown to cause LCA)[1-3]. LCA16 pathogenic allelic variants include c.158G>A (p.Trp53Ter), c.359T>C (p.Iso120Thr), c.458C>T (p.Thr153Iso), c.496C>T (p.Arg166Ter), and c.722T>C (p.Leu241Pro)[1,2,4]. In addition, the compound heterozygous KCNJ13 mutations c.314 G>T (p.Ser105Iso) and c.655C>T (p.G219Ter) are known to cause early-onset retinal dystrophy in an LCA patient[5]. An autosomal dominant KCNJ13 mutation, c.484C>T (p.Arg162Trp), causes early-onset blindness called snowflake vitreoretinal degeneration (SVD OMIM-193230)[6].

Advances in genetic screening will undoubtedly improve our understanding of the array of disorders caused by channelopathies and expand our understanding of the role that KCNJ13 plays in health and disease. An inwardly rectifying potassium channel, Kir7.1, is encoded by KCNJ13 and is expressed in several tissues[7,8]. In the retina, Kir7.1 is expressed exclusively in cell apical processes of RPE, in which it modulates retinal function and health. The role of the Kir7.1 channel in other organs remains to be elucidated[9,10].

A loss-of-function in KCNJ13, as with other channelopathies, is a convenient therapeutic target. We adopted a precision medicine approach in which we used patient-derived iPSC-RPE cells to model LCA16 and explore novel therapies based on mutation-specific and gene-augmentation approaches.

Results

Figure 1D:
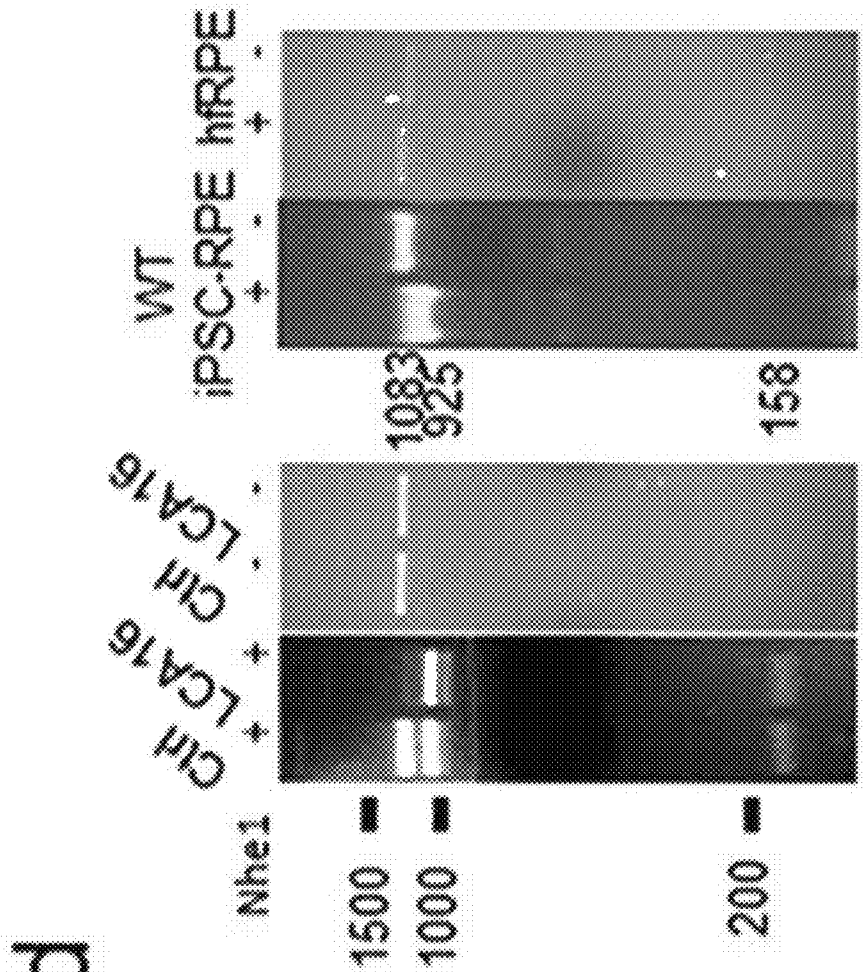
(FIG. 1D) Analysis of the Nhe1 digestion product from the control, LCA16, and wild-type iPSC-RPE lines and human fetal RPE cells. The full-length Kir7.1 sequence is 1083 bp in length, and the digested products are 925 and 158 bp in length.
Figure 1C:
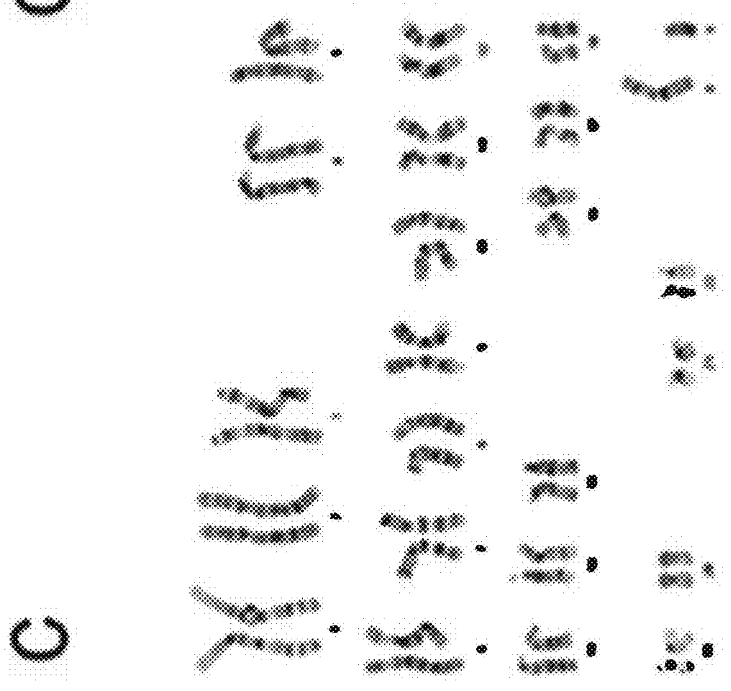
(FIG. 1E) RPE cell-specific gene expression in iPSC-RPE cells.
(FIG. 1F) Electron micrograph of a representative LCA16 iPSC-RPE cell.
(FIG. 1G) Comparison of the average mitochondria (Mit) count within 10 μm of the cell.
(FIG. 1H) Evaluation of the average length of RPE apical (AP) processes.
(FIG. 1I) Immunofluorescence localization of Kir7.1 (red), ZO-1 (green) and DAPI (blue) in control iPSC-RPE cells. Both the lower and side panels reveal a polarized distribution of Kir7.1 in reference to ZO-1 and DAPI (z-stack images).
(FIG. 1J) Localization of Kir7.1 (red), ZO-1 (green) and DAPI (blue) in LCA16 iPSC-RPE.
(FIG. 1K) Western blot results showing the expression of RPE cell-specific proteins in both tissue samples. Using a C terminal-specific antibody against Kir7.1, we detected Kir7.1 protein in whole-cell lysates from the control iPSC-RPE but not in those from the LCA16 iPSC-RPE. Phagosomes (red) localization within control iPSC-RPE (FIG. 1L) and LCA16 iPSC-RPE (FIG. 1M) samples.
Figure 1F:
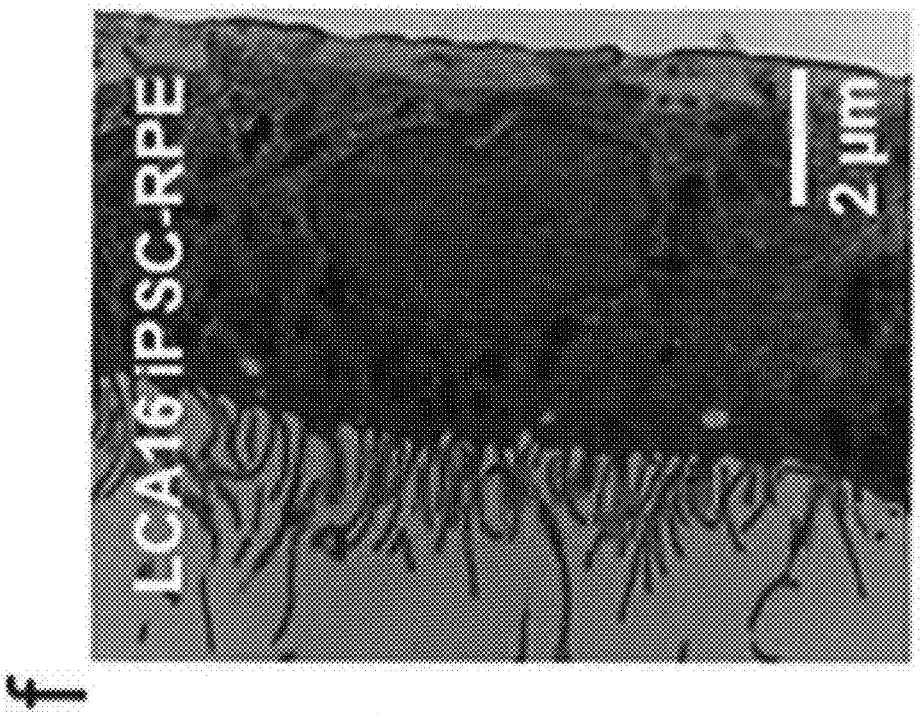
Figure 1E:
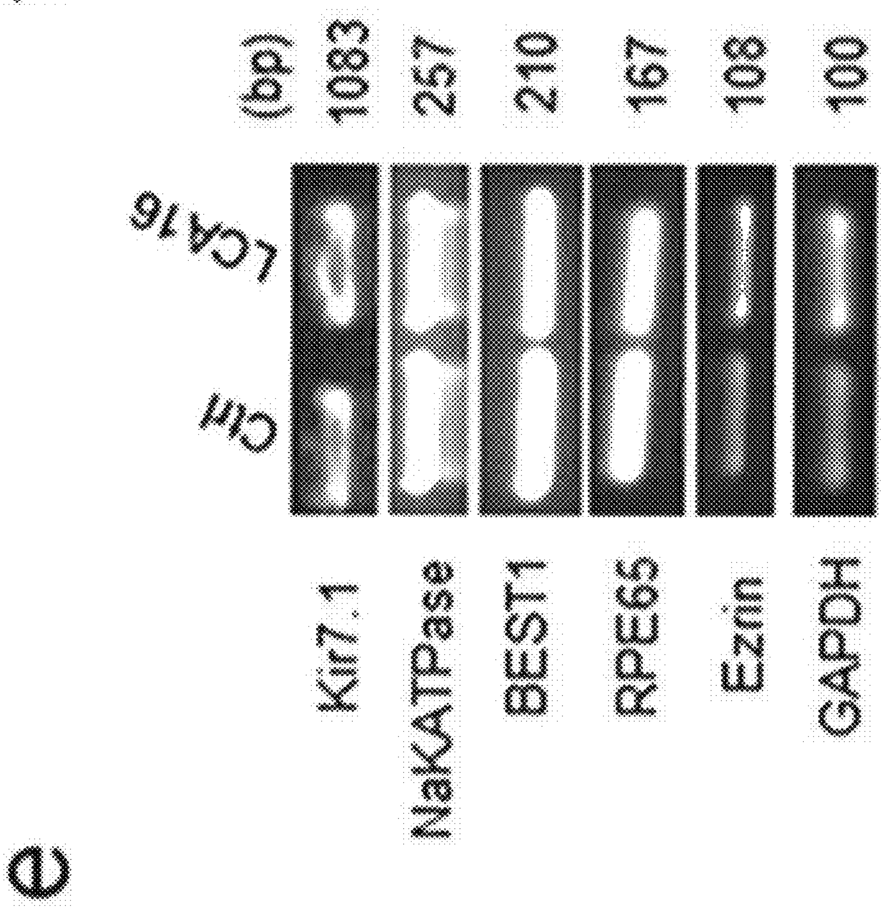

We have previously reported that targeted inhibition of Kir7.1 in the mouse retina (induced using either siRNA or a pharmacological blocker) causes an altered electroretinogram phenotype, consistent with that observed in LCA16 patients[11]. Here, we outline our development of patient-derived iPSC-RPE cells from skin biopsies from one LCA16 patient carrying a nonsense mutation (Trp53Ter) in exon 2 of the KCNJ13 gene, and an unaffected healthy family member. We were able to model characteristic LCA16 pathological features in RPE cells obtained via in vitro differentiation using a cocktail of transcription factors[12]. These cells had normal RPE morphology, including a cobblestone appearance and pigmentation (FIGS. 1A and 1B). DNA sequencing confirmed that the control cells were heterozygous while the LCA16 cells were homozygous for the mutation 158G>A. In addition, the LCA16 cells had a normal karyotype (FIG. 1C). The LCA16 mutation introduced a restriction site for Nhe1, enabling the Kir7.1 mutant sequence to be identified in patient-derived iPSC-RPE, further verifying the presence of a homozygous mutation (FIG. 1D). The control iPSC-RPE were tested and found to be heterozygous carriers, consistent with the genotype of the donor (FIG. 1D). There was no difference in the expression of RPE-specific genes between the two cell types (FIG. 1E). Thus, the patient-derived iPSC-RPE conformed with the genotype of inherited retinal dystrophy and therefore provided a disease-specific cellular model[1].

Figure 1G:
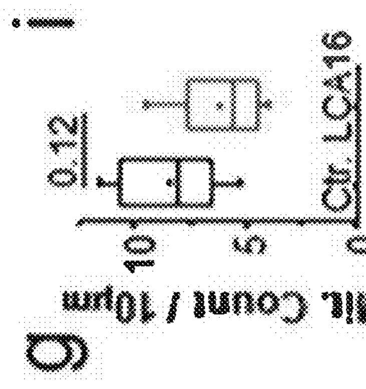
Figure 1H:
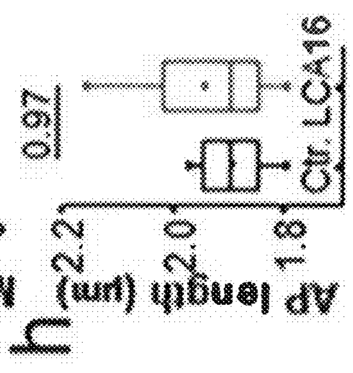
Figure 1I:
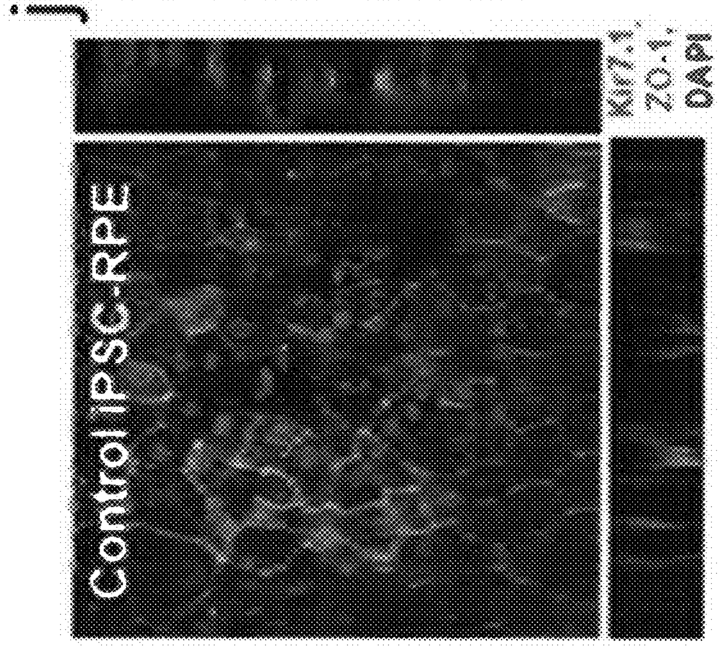
Figure 1J:
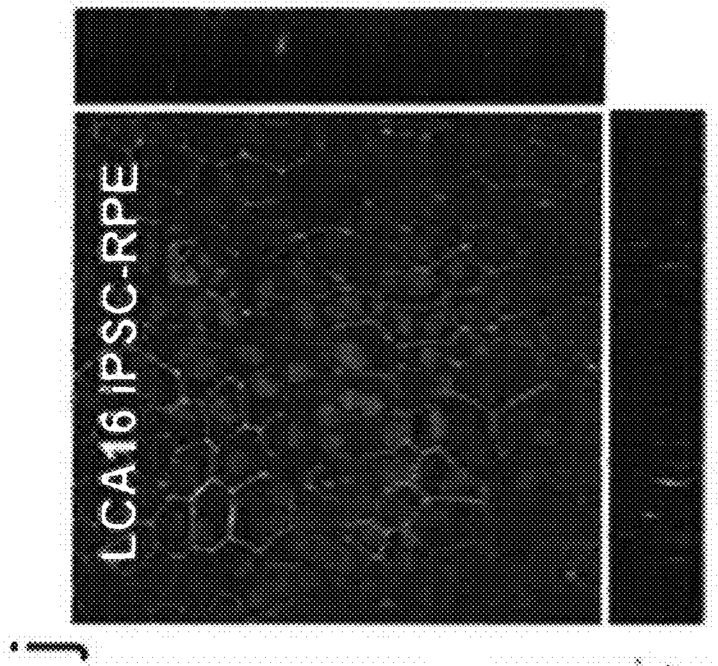
Figure 1K:
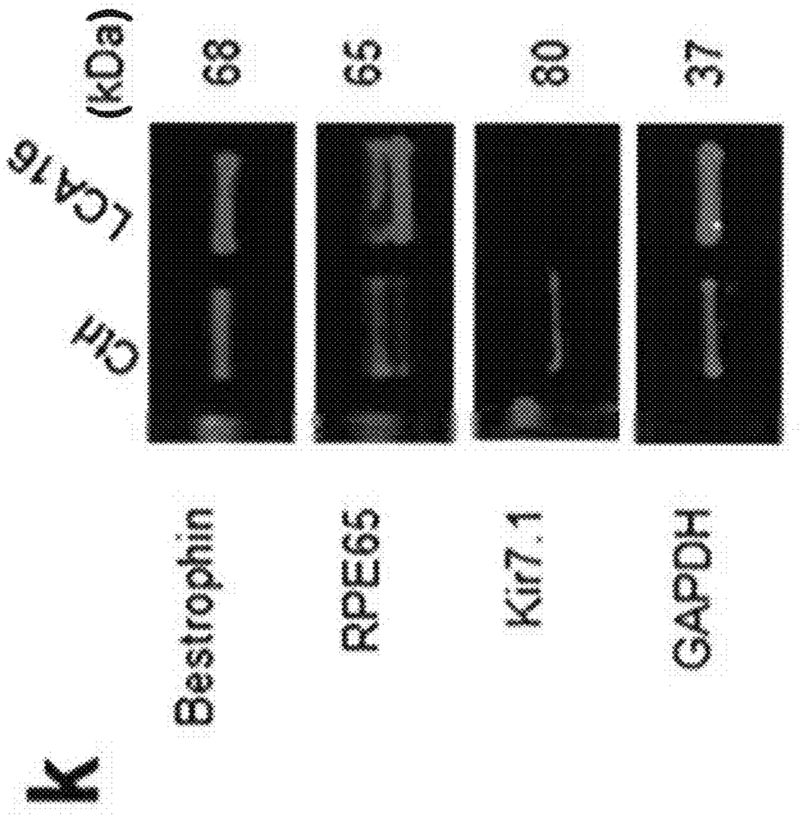

Kir7.1 channels are localized within the highly specialized apical membrane processes of the RPE[11,13]. Electron microscope image analysis of intact apical membrane structures showed that the cells had a polarized structure, including intact basal membrane in-foldings and elongated apical processes that measured 1.49±0.05 μm in length in the controls, and 1.5±0.14 μm in length in the mutants (P=0.96, n=7) (FIGS. 1F, H and FIGS. 3A-3D). The distribution and number of mitochondria in the two cell lines appeared normal, averaging 8.4±1 and 6.22±0.8 in the control and mutant cells, respectively (P=0.12, n=6) (FIGS. 1F and 1G). Kir7.1 protein expression was detected on the apical membrane of mature control iPSC-RPE cells but not in LCA16 iPSC-RPE cells (FIGS. 1I and 1J). We did not find any difference in protein expression between the two cell lines, except for Kir7.1 (FIG. 1K). The Trp53Ter locus is located within the second exon of the 3-exon KCNJ13 sequence. We have previously shown that a nonsense substitution at amino acid 53 results in a truncated protein product, which explains why the LCA16 patient-derived iPSC-RPE failed to express the full-length Kir7.1 protein.

Figure 1L:
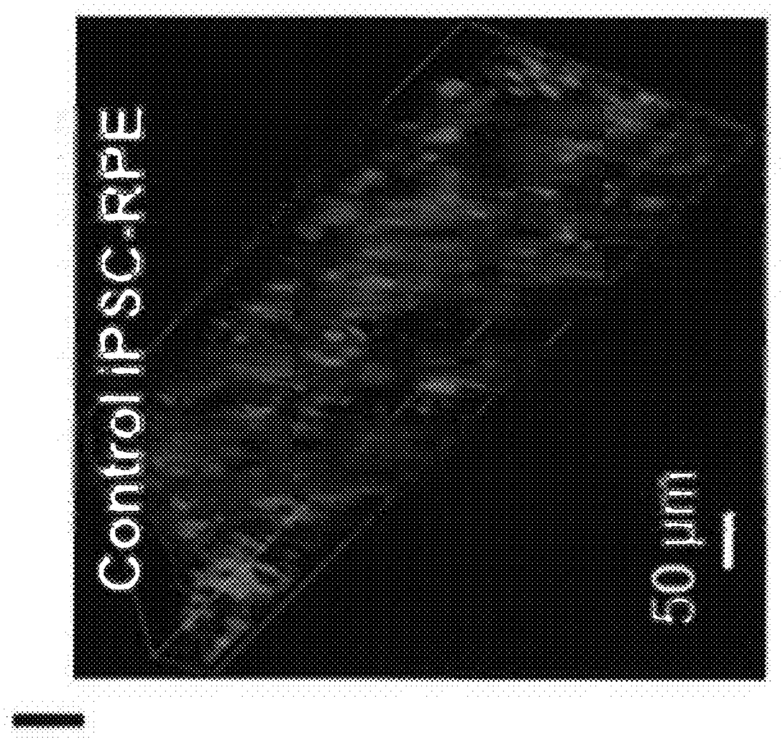
Figure 1N:
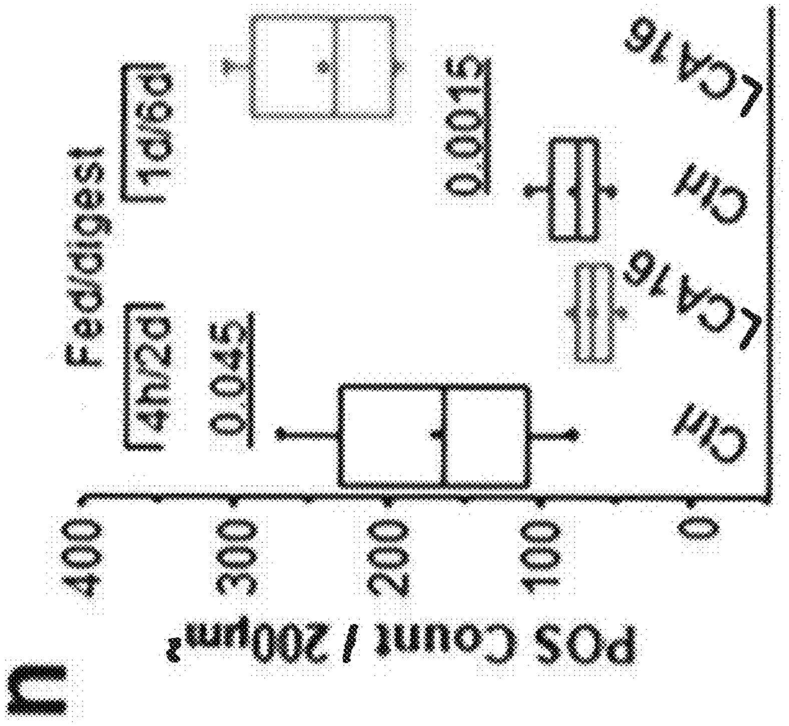
Figure 1M:
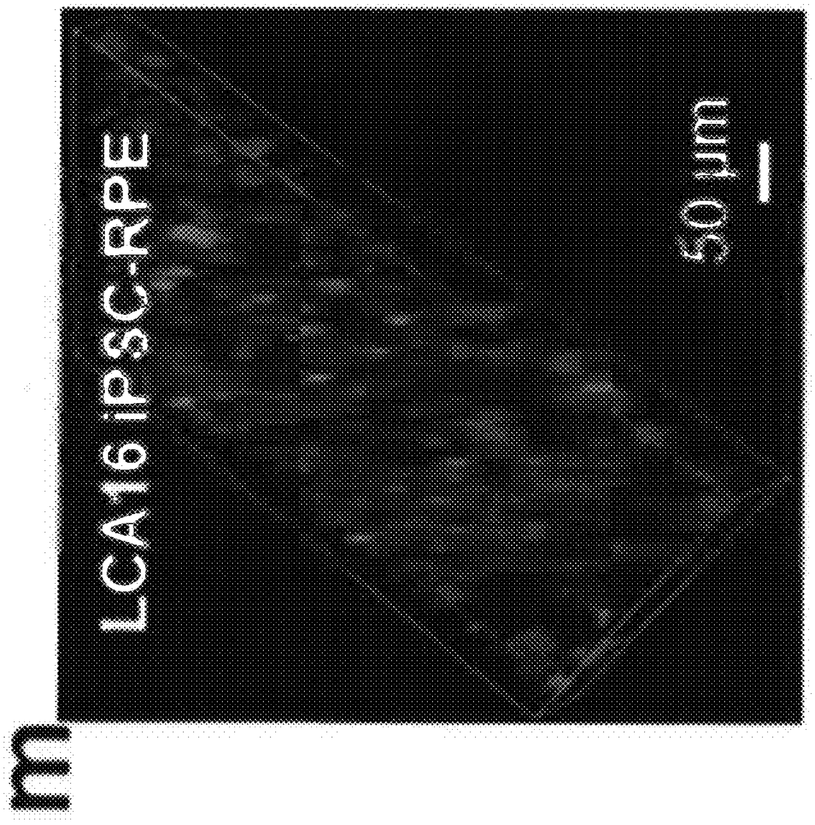

One of the key physiological functions of RPE cells is the daily phagocytosis of the photoreceptor outer segment, which contributes to the renewal process. To test whether the absence of normal Kir7.1 protein alters phagocytosis, we fed both control and LCA16 iPSC-RPE cell cultures with fluorescently labeled photoreceptor outer segments (POS). The cells were fed the POS for 4 hrs, and then, phagosome digestion by RPE cells was allowed for an additional 48 hrs. We then determined that control iPSC-RPE showed a higher rate of phagosomal uptake than LCA16 patient-derived iPSC-RPE (169±40 vs 66.5±7.4, P=0.04, n=4) (FIGS. 1L, 1M and 1N). In contrast, when cells were fed with POS for 1 day and then allowed to digest phagosomes for 6 days, the LCA16 iPSC-RPE cells failed to digest the POS (80.2±11.1 vs 244.2±27.6 counts within a 200 $\mu m^2$ field, P=0.001, n=4) (FIGS. 3A-3D). This finding suggests that the pigmentation observed in LCA16 is likely due to an inability to normally phagocytose POS, which therefore accumulate over time in the retinas of affected individuals.

Figure 2B:
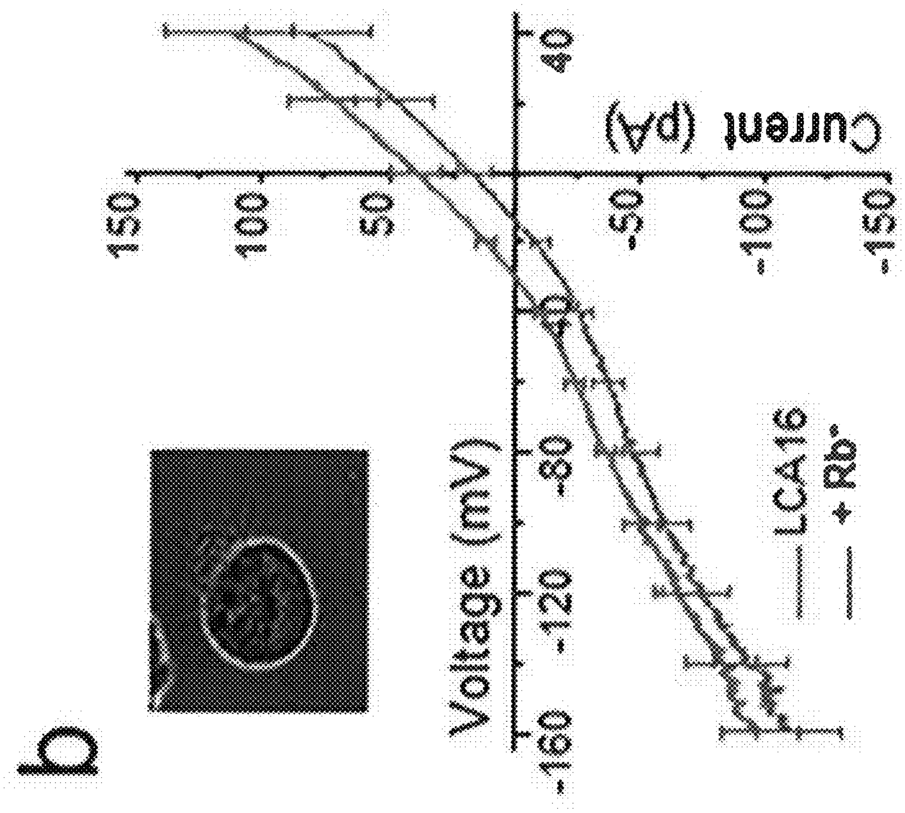
(FIG. 2B) An average I/V curve using normal K+ (red) and high Rb+ (light blue) in LCA16 iPSC-RPE cells.
Figure 2A:
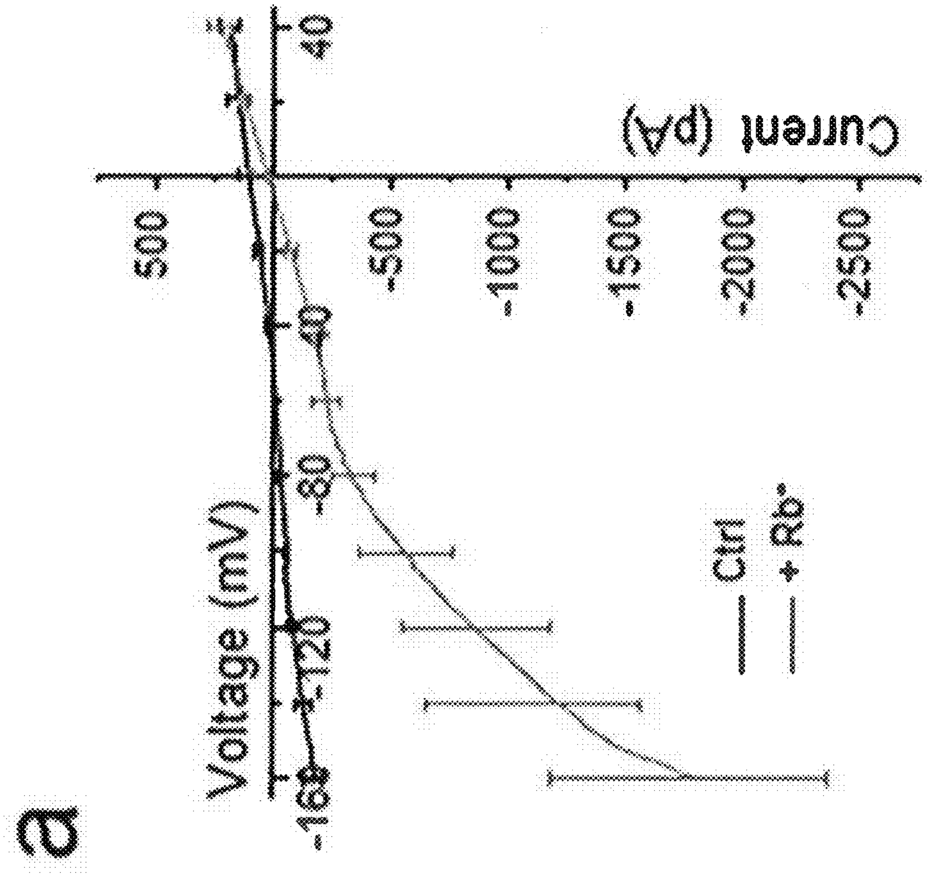
FIGS. 2A-2N show a putative Kir7.1 loss-of-function cure through nonsense mutation suppression or gene augmentation.
Figure 2C:
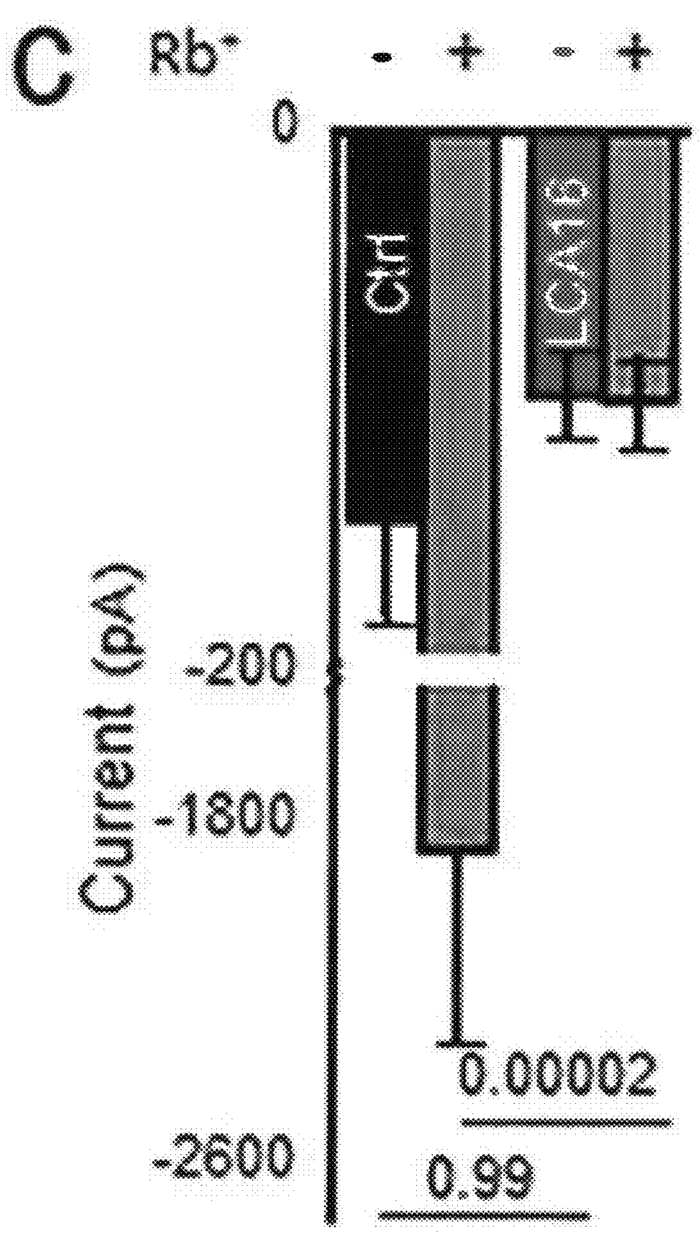
(FIG. 2C) Average plot of an inward current amplitude measured at −150 mV. Color representation as shown in a and b.
Figure 2D:
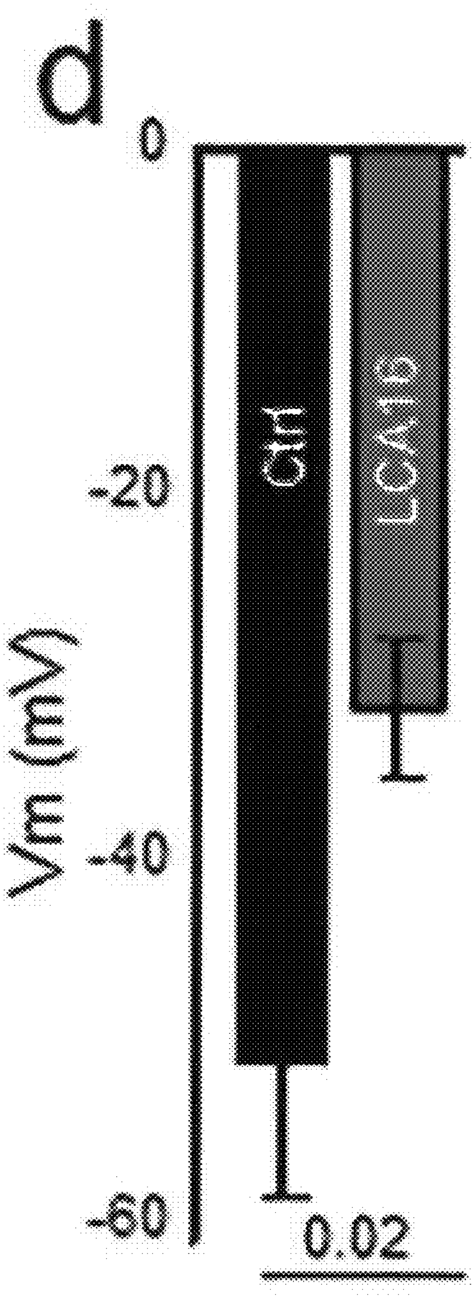
(FIG. 2D) Comparison of the average membrane potential of the control (black) cells to depolarized LCA16 (red) RPE cells.

We hypothesized that a nonfunctional channel contributes to the LCA16 phenotype, and we tested this hypothesis by performing whole-cell electrophysiology with iPSC-RPE cells. One of the challenges in studying ion-channels in iPSC cells is their low level or lack of expression. As we have shown the development of specialized apical processes and demonstrated that Kir7.1 localizes to the apical membrane, we were able to detect a small but measurable Kir7.1 current (−120.2±37 pA) in control iPSC-RPE cells. Normal function was confirmed by a fold increase in Rb+ permeability (−439.5±155.7 pA, n=5) (FIGS. 2A and 2C), which is a specific property of the Kir7.1 channel[14]. However, in LCA16 iPSC-RPE cells, we did not detect any fold change in the current amplitude mediated by Rb+ conductance (−98.1±15.7 pA & −100.7±15.9 pA, n=9) (FIGS. 2B and 2C). A direct comparison of both current amplitude (P=0.0006 with Rb) and cell membrane potential (−50±5.1 vs −30.6±3.7 mV, P=0.0005; as shown in FIG. 2D) supported our hypothesis that the cause of blindness is a truncated nonfunctional Kir7.1 channel. We have shown earlier using mice and exogenous expression of Kir7.1 channel that a nonfunctional channel depolarizes RPE cells[1,11].

Figure 2E:
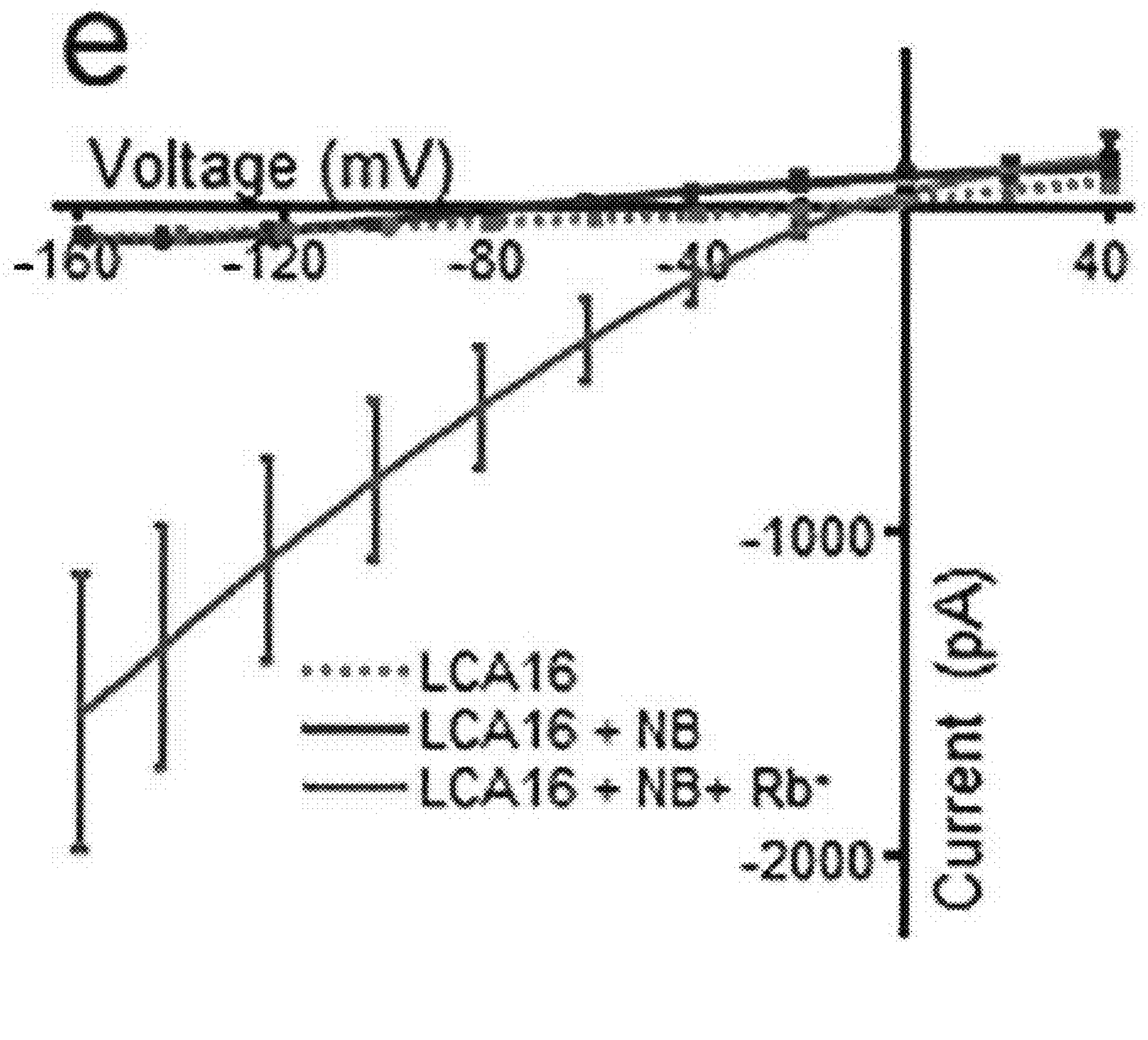
(FIG. 2E) Average I/V relationship before (red) and after (dark blue) treatment with NB84. The current measured in Rb+ is shown as a light-blue trace. Evaluation of the average inward current measured at −150 mV (FIG. 2F) and membrane potential (FIG. 2G) to demonstrate the effect of NB84.
Figure 2H:
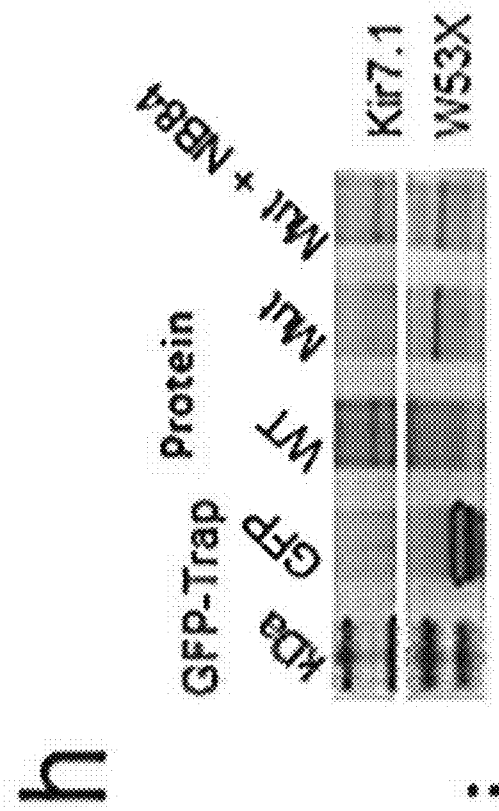
(FIG. 2H) A GFP-fused protein was precipitated using anti-GFP antibody as a trap, and silver staining shows the purified component bands for the full-length Kir7.1 and W53X proteins. The GFP control sample shows a smaller protein product.
Figure 2I:
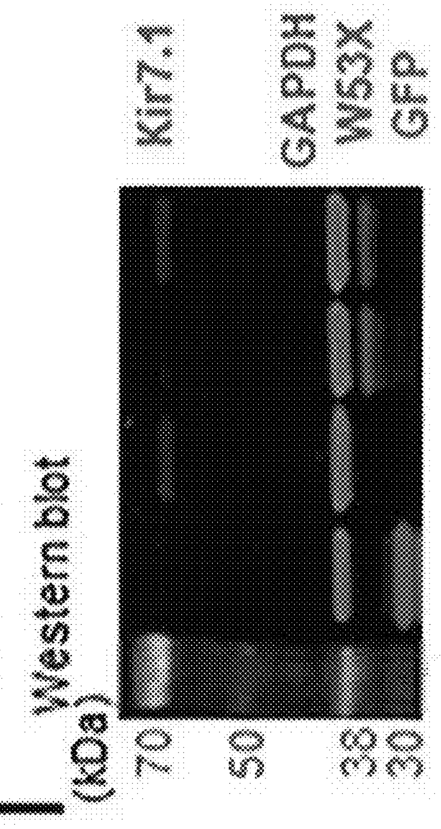
(FIG. 2I) Western blot analysis of cell lysates shows the respective bands when probed with a GFP-specific antibody. A partial restoration of the full-length protein product is observed after NB84 treatment.
Figure 2F:
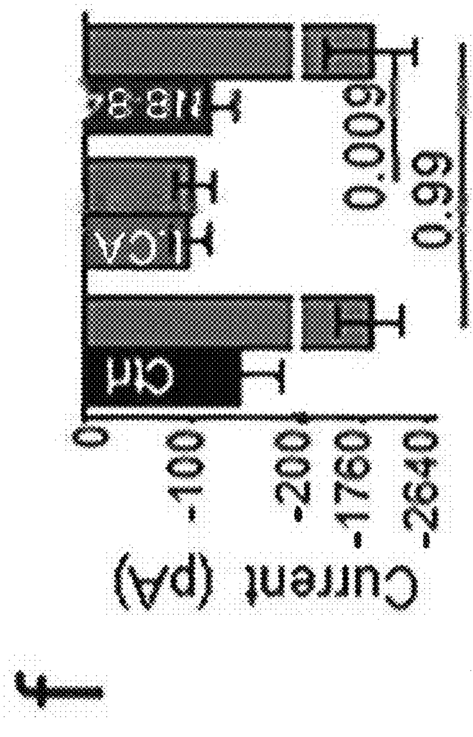
(FIG. 2J) Plot of the average I/V curve for Kir7.1 currents measured in GFP-positive cells expressing a normal copy of the human Kir7.1 clone. Both K+ (green) and Rb+ (light blue) traces are shown. Average plot of the current amplitudes (FIG. 2K) measured at −150 mV and membrane potential (FIG. 2L) to show rescue after gene augmentation.
(FIG. 2M) Cultured LCA16 iPSC-RPE showing wild-type Kir7.1 (green), ZO-1 (red) and DAPI (blue) proteins. Z-stack planes are shown in the lower and side panels.
Figure 2G:
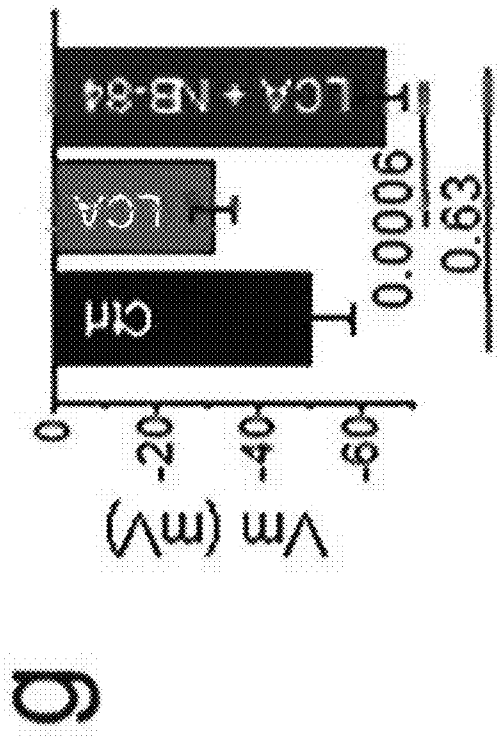

The LCA16 mutation we are studying is a tryptophan (UGG) to amber stop codon (UAG) variant. This nonsense mutation in eukaryotes can be suppressed by the incorporation of near cognate amino acid tRNA in the presence of the small-molecule read-through designer aminoglycoside NB84 (US Patent Publication #20140357590A1)[15-17]. We further assessed the functional consequences of NB84-mediated read-through of Kir7.1 current in LCA16 iPSC-RPE cells. Following treatment with 500 μM NB84, we obtained a measurable current in LCA16 iPSC-RPE of −94.3±24 pA that was enhanced by 10-fold upon the introduction of Rb+ (−1562.7±546.7 pA, P=0.005, n=8), a permeant ion (FIGS. 2E and 2F). A significant recovery of membrane potential from −30.6±3.7 in the nontreated cells to −56.3±3.6 mV (P=0.0001, n=10) (FIG. 2G) in the treated cells further justified the use of read-through drug therapy. We were able to determine that a subgroup of cells had rescue in membrane potential without any significant change in current amplitude (FIGS. 4A-4D). This result is perhaps based on which near cognate amino acid (UAG to UAC-tyrosine, UCG-serine, GAG-glutamic acid, or CAG-glutamine) gets incorporated during Kir7.1 protein translation. To optimize the detection of Kir7.1 proteins, we used a stable cell line with a low expression level of a Kir7.1-GFP fusion clone. In NB84-treated cells, a protein band equivalent to the full-length product was detected in addition to the truncated protein band, in conjunction with a rectified membrane potential and current (FIGS. 2H, 2I and FIGS. 5A-5D). NB84 potentiates the specific read-through of a recessive Trp53Ter codon mutation, and we found that as low as a 25% rescue of functional channels was sufficient to circumvent both membrane potential and potassium current and thereby rescue the disease phenotype (FIGS. 6A-6D).

Figure 2J:
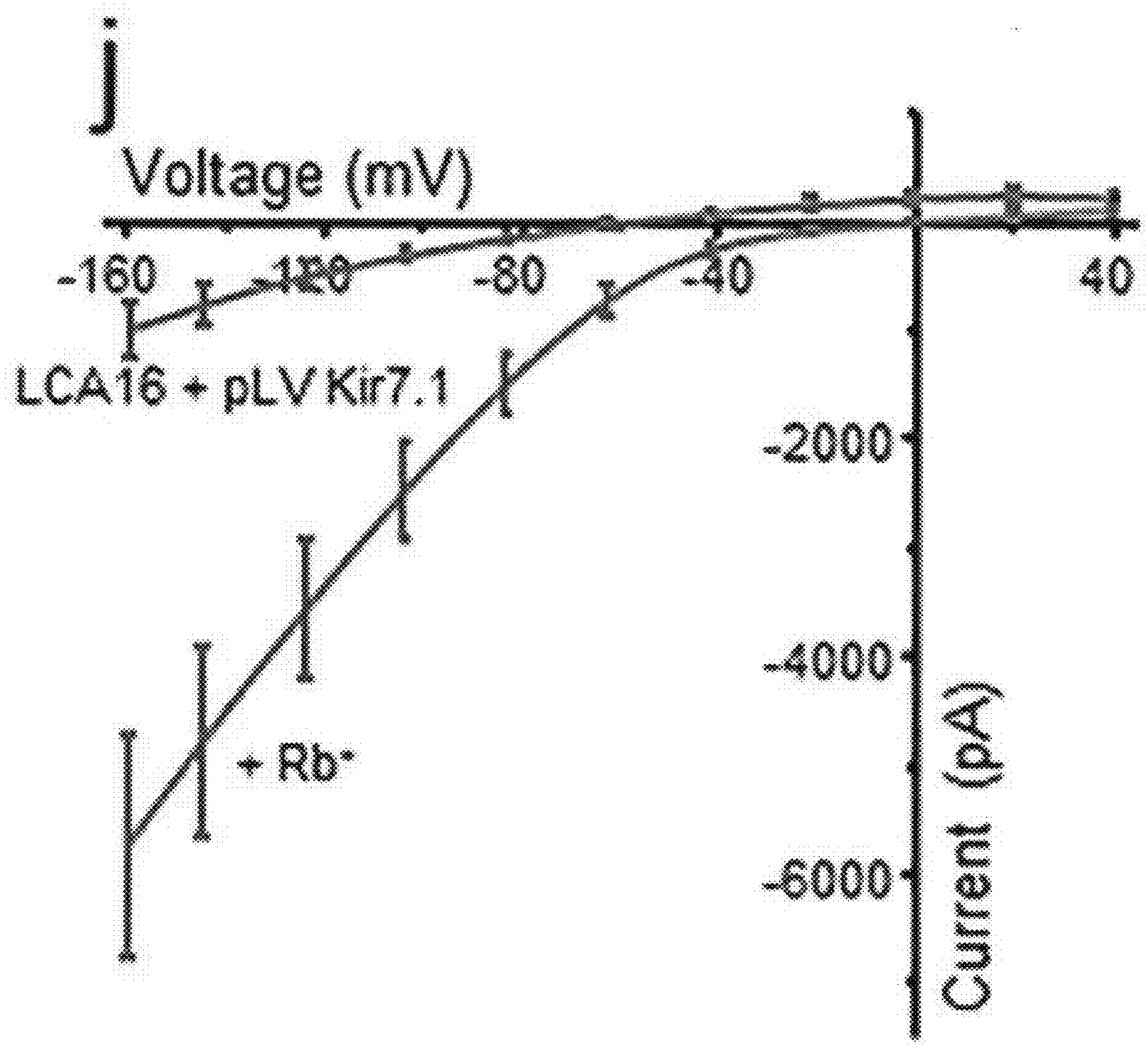
Figure 2K:
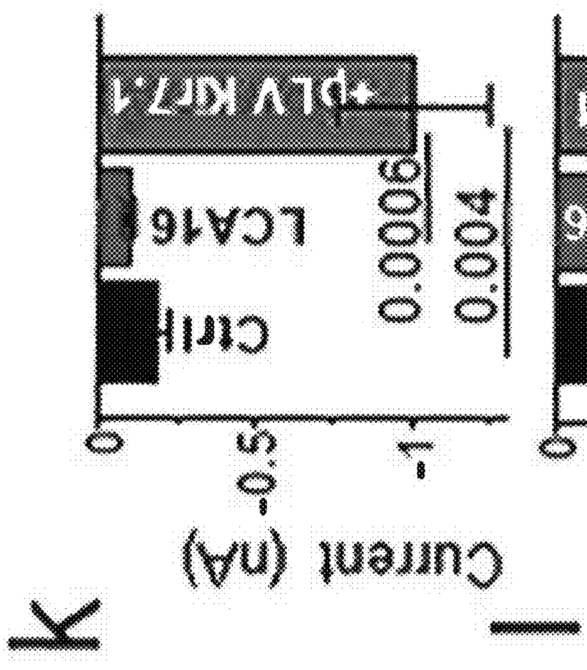
Figure 2L:
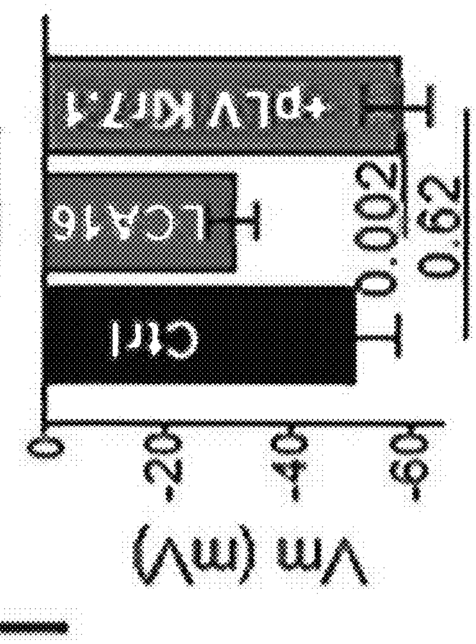
Figure 2M:
Figure 2N:
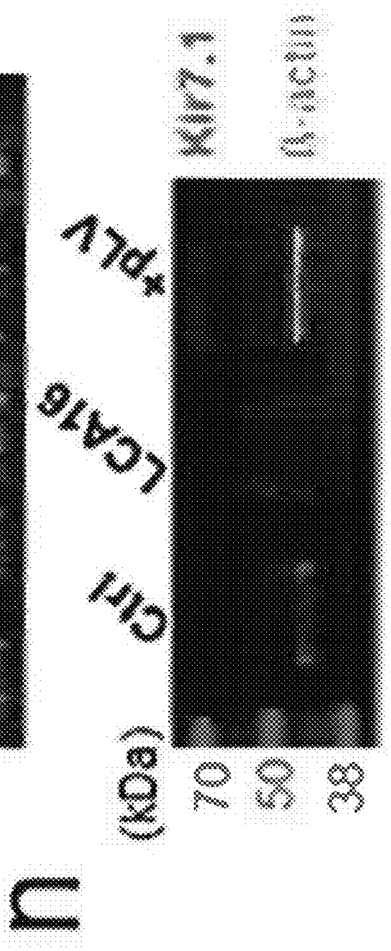
Figure 6B:
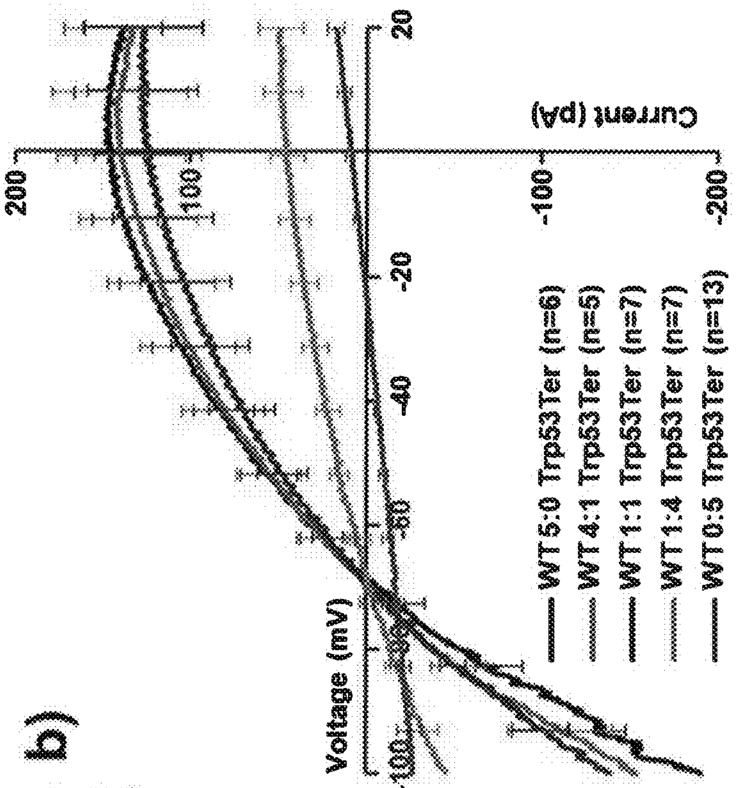
FIGS. 6A-6D show determination of the extent of wild-type protein expression required for functional rescue. We were particularly interested in quantitating how much gene augmentation/correction is required to restore channel function. We expressed either Trp53Ter or wild type Kir7.1 protein alone or in various combinations in CHO cells.
Figure 6A:
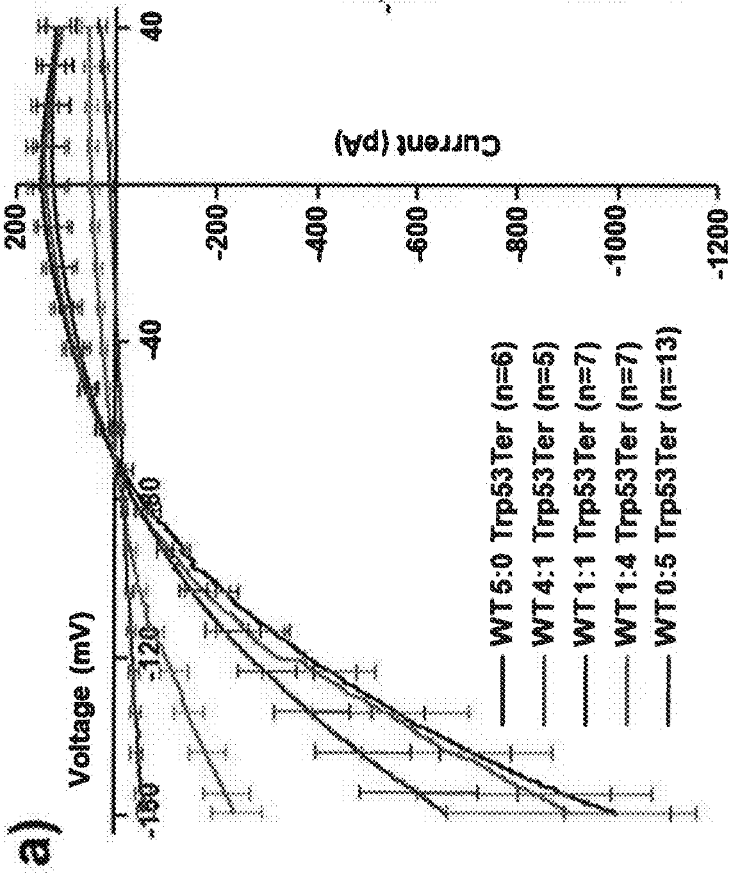
Figures 6C, 6D:
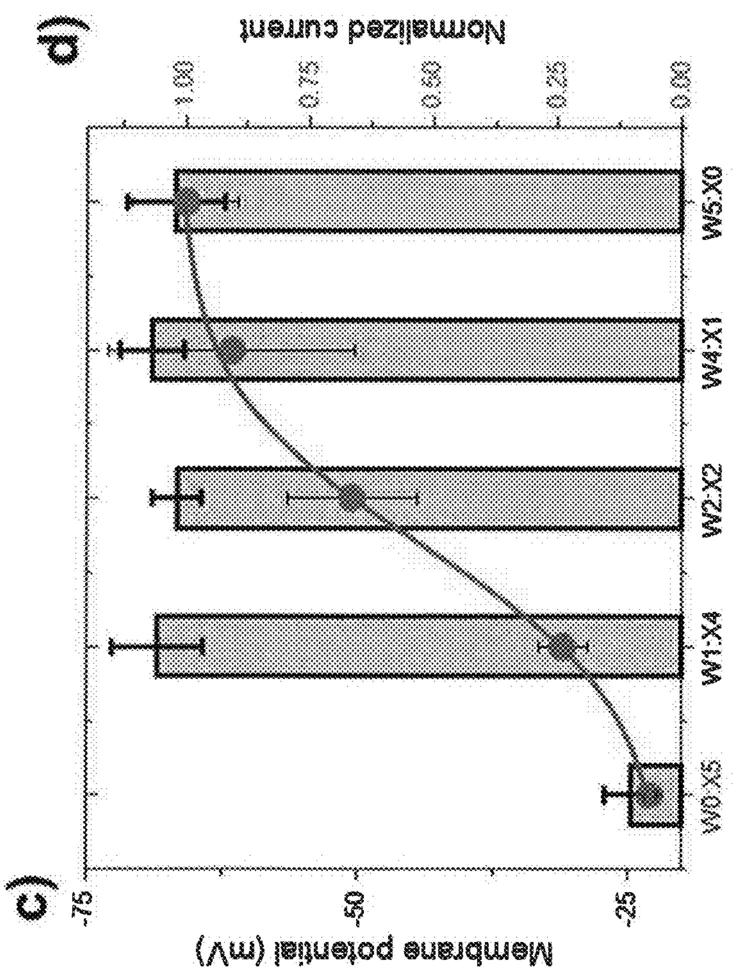

The particular mutation studied herein and other mutations that cause blindness are potential targets for gene therapies given the recent FDA approval of a treatment for blindness[18,19]. We designed a lentiviral vector with an N-terminal GFP fused to the human Kir7.1 open reading frame under the control of the EF1a promoter[20]. Intriguingly, after transduction with lentiviral particles Kir7.1-expressing cells presented normal Kir7.1 currents or even slightly higher amplitudes than those observed in the control cells (−920.5±223 pA, P=0.001, n=8). This current was further potentiated by the introduction of Rb+ (−5452.8±929 pA), as expected for a normal functioning Kir7.1 channel (FIGS. 2J and 2K). In addition to K+ currents, the membrane potential of LCA16 iPSC-RPE cells was normalized (−57.5±5.4 mV, P=0.0008) (FIG. 2I). Moreover, newly expressed Kir7.1 was shown to be localized to the apical membranes of diseased iPSC-RPE cells (FIGS. 2M and 2N). Thus, reversal of Kir7.1 function in RPE cells is a potential intervention that will improve vision in patients with congenital blindness due to KCNJ13 mutations.

In summary, in autosomal recessive LCA16, we used reprogrammed iPSC-RPE cells to identify unique features associated with a nonsense mutation. The finding that membrane potential was depolarized in diseased cells, which were unable to phagocytose POS, is consistent with the slow progression toward blindness observed in LCA16 patients in addition to their other clinical manifestations, such as electroretinogram abnormalities and retinal pigmentation. Using endogenously expressed Kir7.1 in an iPSC-RPE model, we show that both mutation-specific therapy using nonsense mutation suppression via a designer aminoglycoside and/or the rescue of channelopathy via lentiviral gene augmentation produced a potassium current and normal membrane potential (FIGS. 7A-7D). Thus, we show herein a preclinical therapy for pediatric blindness and a precision medicine approach to a cure for genetic diseases.

Methods

Differentiation of hiPSC-RPE. Fibroblasts from two subjects were reprogrammed to induced pluripotent stem cells and cultured using established methods[1-3]. One of the subjects was an LCA16 patient with two copies of the Trp53Ter autosomal recessive mutation in the KCNJ13 gene, and the second subject was heterozygous for this mutation. The hiPSC lines were differentiated to RPE using protocols described earlier[2-5]. Briefly, hiPSCs were cultured either on mouse embryonic fibroblasts (MEFs) in iPS cell media (Dulbecco's modified Eagle's medium (DMEM): F12 (1:1), 20% Knockout Serum, 1% minimal essential medium (MEM) non-essential amino acids, 1% GlutaMAX, β-mercaptoethanol, 20 ng/ml FGF-2), or on Matrigel® with mTeSR1 media. Cells were lifted enzymatically and grown as embryoid bodies (EBs) in iPS medium without FGF-2, and at day 4, changed to neural induction medium (NIM; DMEM: F12; 1% N2 supplement, 1% MEM non-essential amino acids, 1% L-Glutamine, 2 μg/ml Heparin), or in mTeSR1 and gradually transitioned to NIM by day 4. There were no differences observed in RPE differentiation between these two approaches. At day 7, free-floating Ebs were plated on laminin-coated culture plates to continue differentiation as adherent culture. At day 16, the 3D neural structures were removed, and medium was switched to retinal differentiation medium (DMEM/F12 (3:1), 2% B27 supplement (without retinoic acid), 1% Antibiotic-Antimycotic). Remaining adhered cells were allowed to continue differentiation for an additional 45 days, followed by microdissection and passaging of pigmented RPE patches to obtain purified monolayers of RPE as described earlier[5]. MEFs, Matrigel® and FGF-2 were purchased from WiCell (Madison, WI), and all other tissue culture reagents were purchased from ThermoFisher.

RT-PCR and Restriction Fragment Length Polymorphism (RFLP). Total RNA was isolated from the mature hiPSC-RPE cells from both patient and the carrier using the Rneasy® kit according to manufacturer's instructions (Qiagen). The quality and the concentration of the isolated RNA was measured using a Nanodrop (ThermoFisher) and 200 ng of RNA was used for cDNA synthesis using the Superscript III first strand cDNA synthesis kit according to manufacturer's instructions (ThermoFisher). PCR was performed with MyTaqHS master mix (Bioline) in a final volume of 25 μl with the following conditions: 95° C. for 5 min followed by 35 cycles of denaturation at 95° C. for 15 sec, annealing at 55° C. for 30 sec, and extension at 72° C. for 30 sec. A final extension step was done for 10 min at 72° C. and amplification products were visualized by electrophoresis on a 2% agarose gel containing Midori green advanced stain (Nippon Genetics Europe). For RFLP assay PCR was performed as described with primers specific to the full length KCNJ13 mRNA (Fwd 5'-GCTTCGAATTCCGACAGCAGTAATTG-3' (SEQ ID NO: 7) and Rev 5'-ATCCGGTGGATCCTTATTCTGTCAGT-3' (SEQ ID NO: 8). The PCR products were then digested by NheI restriction enzyme (ThermoFisher) and visualized by electrophoresis on a 2% agarose gel containing Midori green advanced stain (Nippon Genetics Europe).

Transmission Electron Microscopy. Monolayers of hiPSC-RPE on transwell inserts (Corning, Cat #3470) were fixed in a solution of 2.5% glutaraldehyde, 2.0% paraformaldehyde in 0.1M sodium phosphate buffer (PB), pH 7.4 for ~1 hr at room temperature (RT). Samples were rinsed 5×5 minutes in 0.1M PB. The rinsed cultures were then post-fixed in 1% Osmium Tetroxide (Os04), 1% potassium ferrocyanide in PB for 1 hr at RT. Following post-fixation, samples were rinsed in PB, as before, followed by 3×5 minute rinses in distilled water to clear the phosphates. The samples were then stained en bloc in uranyl acetate for 2 hrs at RT and dehydrated using ethanol series. The membrane was cut from the transwell support, placed in an aluminum weighing dish, transitioned in propylene oxide (PO) and allowed to polymerize in fresh PilyBed 812 (Polysciences Inc. Warrington, PA). Ultrathin sections were prepared from these polymerized samples and processed before capturing and documenting the images with FEI CM120 transmission electron microscope mounted with AMT BioSprint12 (Advanced Microscopy Techniques, Corp. Woburn, MA) digital camera.

Immunocytochemistry (ICC). Transwell inserts with monolayer of hiPSC-RPE cells from either the patient or control were fixed as follows: the transwell membrane was cut out and fixed by immersing it in 4% paraformaldehyde in phosphate-buffered saline for 10 mins in the dark. The membrane with cells was then washed with chilled PBS twice and blocked for 2 hrs in blocking solution that contained 5% goat serum and 0.25% Tween-20 in 1×PBS. For confocal microscopy, the cells were then incubated for 24-48 hrs with primary antibodies raised against Kir7.1 (mouse monoclonal IgG, 1:250—Santa Cruz), and ZO-1 (rabbit polyclonal, 2.5 μg/ml—ThermoFisher) prepared in incubation solution (Blocking solution diluted in 1:3 with 1×PBS). After incubation with primary antibody, the membranes were washed with chilled 1×PBS thrice and incubated with conjugated secondary antibodies (Donkey anti goat Alexa Fluor® 488, donkey anti Rabbit Alexa Fluor® 594 and DAPI, 1:500) in incubation solution for an hour in dark. A no primary antibody control was included for all experiments. Immunostained samples were imaged on a Nikon C2 confocal microscope (Nikon Instruments Inc., Mellville, NY).

Western blotting. Protein was isolated from >60 day old hiPSC-RPE cells on transwells using Radioimmunoprecipitation assay (RIPA) lysis buffer (ThermoFisher) along with sonication[6]. The protein content of the lysates was measured using commercially available bicinchoninic acid (BCA) assay kit (ThermoFisher). The samples were diluted to contain equal amounts of protein and mixed with 2×Laemmli sample buffer (Bio-Rad) then electrophoresed on NuPAGE® Novex® 4-12% pre-cast polyacrylamide gel (ThermoFisher) followed by transfer to polyvinlidene difluoride (PVDF) membranes using the iBlot® dry blotting system (ThermoFisher). The membranes were blocked with odyssey blocking buffer (LI-COR Biosciences) containing 0.1% Tween-20 for at least 2 hours at 4° C. After blocking, the membranes were incubated in the appropriate primary antibodies prepared in the Odyssey blocking buffer containing 0.1% Tween-20. The primary antibodies used for this purpose were anti-Kir7.1 (mouse monoclonal, 1:1000-Santa Cruz Biotech), anti-Bestrophin1 (mouse monoclonal, 1:1000—Novus biologicals), anti-RPE65 (mouse monoclonal, 1:1000—ThermoFisher), anti-GFP (mouse monoclonal, 1:1000-NeuroMab), anti-GAPDH (rabbit monoclonal, 1:1000-Cell Signaling), and anti-β-actin (rabbit monoclonal, 1:1000-Cell Signaling Technology) as a loading control. The membranes were incubated with these primary antibodies in combination with control overnight at 4° C. and then washed with Tris buffered saline containing 0.1% Tween-20 4 times before incubating them for another 1 hour with the appropriate IRDye™ secondary antibodies (LI-COR Biosciences) at 1:20000 dilutions in blocking buffer. The membranes were washed 4 times and imaged on an Odyssey® Imaging system.

Photoreceptor Outer Segment (POS) isolation. Fresh bovine eyes were dissected under dim red light and retinas were removed carefully from the eyecup. Isolated retinas were placed in chilled homogenization solution (20% w/v sucrose, 20 mM Tris/Acetate pH 7.2, 2 mM $MgCl_2$, 10 mM glucose, 5 mM taurine) and mixed gently. The suspension was then passed though gauze to remove clumps. This filtrate was centrifuged through a 25-60% sucrose gradient at 25000 rpm for an hour at 4° C. The pinkish layer containing the POS was removed and washed with wash solution 1 (20 mM tris acetate pH 7.2 and 5 mM taurine), wash solution 2 (10% sucrose, 20 mM tris acetate pH 7.2 and 5 mM taurine) and wash solution 3 (10% sucrose, 20 mM sodium phosphate pH 7.2 and 5 mM taurine) by centrifuging at 3000 g for 10 mins respectively before resuspending in DMEM containing 2.5% sucrose and stored at −80° C. until use. To fluorescently label the POS, an unlabeled aliquot was thawed and centrifuged at 2400 g for 5 min. The pellet was then re-suspended in 200 μl of DMEM. To this solution 1 μl of WGA (Wheat Germ Agglutinin) conjugated with Alexa Fluor 594® (1 mg/ml, ThermoFisher) was mixed and incubated for 10 min at 37° C. After completion of incubation with WGA, the tube was again centrifuged at 2400 g for 5 min and the POS pellet was washed twice with DMEM, after which it was used for phagocytosis assays Phagocytosis Assay. The labelled POS were added to culture media and fed to hiPSC-RPE cells growing in transwells that had a transepithelial electrical resistance (TEER) of >150 $\Omega cm^2$.[1] The cells were fed POS for either 4 hrs or 24 hrs after which any POS that had not been phagocytosed were removed by washing the cells 3 times with DMEM media. The cells were then incubated for 24 hrs or 6 days respectively before imaging. The images were captured and analyzed with NIS-Elements using a Nikon C2 confocal microscope (Nikon Instruments Inc., Mellville, NY).

Immunoprecipitation of GFP-Fused protein and silver staining: CHO-K1 cells were transiently transfected to exogenously express either the Kir7.1 WT protein or the Kir7.1 Trp53Ter protein as N-terminal fusions with GFP. Cells expressing Trp53Ter protein were then treated with NB84[8]. Immunoprecipitation was performed using GFP-Trap agarose beads (ChromoTek, Germany) according to the manufacturer's protocol.[6] In brief, the cells were collected and protein isolated as described above for western blotting. GFP-Trap agarose beads were added to the cell lysate and incubated at 4° C. for 2 hours with constant mixing. The mixture was then centrifuged at 2500 g for 2 mins and the beads were washed twice. SDS-sample buffer was added to the beads and incubated at 95° C. for 10 mins followed by centrifugation at 2500×g. The supernatant was separated on a 4-12% acrylamide gel and protein bands were visualized by silver staining using the Pierce Silver Stain kit (ThermoFisher) according to the manufacturer's instructions.

hiPSC-RPE Transduction. Lentivirus, custom engineered to be devoid of pathogenic elements, and carrying KCNJ13 gene fused at N-terminal with green fluorescent protein (GFP) under the control of EF1a promoter, was generated by Cyagen Biosciences (Santa Clara, CA, USA) and used for transduction[9]. LCA-16 hiPSC-RPE monolayer was infected with pLV-EF1a Kir7.1-GFP at an MOI of 200. The cells were cultured for 4-5 days after infection then used for immunocytochemistry and western blotting.

Electrophysiology. Standard whole cell patch clamp on single cells were performed as described[6] Briefly, the tight monolayer of hiPSC-RPE grown on a 6.5 mm transwell was dissociated into a single cell suspension as follows: the medium in which cells were maintained was completely removed and the cells were washed twice with 0NaCMF solution (135 mM NMDG-Cl, 5 mM KCl, 10 mM HEPES, 10 mM Glucose, 2 mM EDTA-KOH and adjusted to pH 7.4 with NMDG free base). The cells were then incubated with 0NaCMF containing papain (2.5 μl/ml), cysteine (0.3 mg/ml), glutathione (0.25 mg/ml) and taurine (0.05 mg/ml) for 45 mins at 37° C. The cells were rinsed with 0NaCMF solution to remove enzymes, resuspended in HEPES-Ringer's (HR) solution [NaCl (135 mM), KCl (5 mM), $CaCl_2$) (1.8 mM), $MgCl_2$ (1 mM), HEPES (10 mM), D-glucose (10 mM), pH 7.4±0.1 with NaOH, prepared in $ddH_2O$], and kept on ice for up to 8 hrs until used for electrophysiological recording.

Single hiPSC-RPE cells with distinct apical processes were chosen for conventional patch clamping. Patch pipettes with a resistance of 3-5 mQ were fabricated from borosilicate capillaries using a pipet puller (P-1000®, Sutter instruments). The glass electrode was then fire polished using a microforge (MF-830®, Narshige). Data acquisition and the holding potential parameters were controlled using the Clampex® software (Axon instruments). Current recorded from the successful patch was amplified using Axopatch 200-B® (Axon Instruments) and filtered at 2 KHz. The signal was digitized using digidata 1400A® (Axon instruments) and analyzed using Clampfit® (Axon Instruments). During patch clamping, HR solution was continuously perfused as an external solution. The patch pipette was filled with solution containing 30 mM KCl, 83 mM K-gluconate, 5.5 mM EGTA-KOH, 0.05 mM $CaCl_2$), 4 mM $MgCl_2$, 10 mM HEPES, pH adjusted to 7.2 with KOH and filtered using the 0.2 μm filter.

Statistical analysis. The statistical analysis was performed using Origin (version 9.1) with a two-tailed Student's t-test to assess the significant differences. $P<0.05$ was considered statistically significant. ANOVA and post hoc Tukey test was also used for multiple comparisons. The data are expressed as the means±SEM.

REFERENCES FOR METHODS

1. Singh, R. et al. iPS cell modeling of Best disease: insights into the pathophysiology of an inherited macular degeneration. *Hum Mol Genet* 22, 593-607 (2013).
2. Meyer, J. S. et al. Modeling early retinal development with human embryonic and induced pluripotent stem cells. *Proc Natl Acad Sci USA* 106, 16698-703 (2009).
3. Phillips, M. J. et al. Blood-derived human iPS cells generate optic vesicle-like structures with the capacity to form retinal laminae and develop synapses. *Invest Ophthalmol Vis Sci* 53, 2007-19 (2012).
4. Capowski, E. E. et al. Loss of MITF expression during human embryonic stem cell differentiation disrupts retinal pigment epithelium development and optic vesicle cell proliferation. *Hum Mol Genet* 23, 6332-44 (2014).
5. Singh, R. et al. Functional analysis of serially expanded human iPS cell-derived RPE cultures. *Invest Ophthalmol Vis Sci* 54, 6767-78 (2013).
6. Pattnaik, B. R. et al. A Novel KCNJ13 Nonsense Mutation and Loss of Kir7.1 Channel Function Causes Leber Congenital Amaurosis (LCA16). *Hum Mutat* 36, 720-7 (2015).
7. Parinot, C., Rieu, Q., Chatagnon, J., Finnemann, S. C. & Nandrot, E. F. Large-scale purification of porcine or bovine photoreceptor outer segments for phagocytosis assays on retinal pigment epithelial cells. *J Vis Exp* (2014).
8. Brendel, C. et al. Readthrough of nonsense mutations in Rett syndrome: evaluation of novel aminoglycosides and generation of a new mouse model. *J Mol Med* (*Berl*) 89, 389-98 (2011).
9. Yanez-Munoz, R. J. et al. Effective gene therapy with nonintegrating lentiviral vectors. *Nat Med* 12, 348-53 (2006).

REFERENCES FOR EXAMPLE 1 BESIDES METHODS

Pattnaik, B. R. et al. A Novel KCNJ13 Nonsense Mutation and Loss of Kir7.1 Channel Function Causes Leber Congenital Amaurosis (LCA16). *Hum Mutat* 36, 720-7 (2015).

2. Sergouniotis, P. I. et al. Recessive mutations in KCNJ13, encoding an inwardly rectifying potassium channel subunit, cause leber congenital amaurosis. *Am J Hum Genet* 89, 183-90(2011).
3. Perez-Roustit, S. et al. Leber Congenital Amaurosis with Large Retinal Pigment Clumps Caused by Compound Heterozygous Mutations in Kcnj13. *Retin Cases Brief Rep* 11, 221-226 (2017).
4. Khan, A. O., Bergmann, C., Neuhaus, C. & Bolz, H. J. A distinct vitreo-retinal dystrophy with early-onset cataract from recessive KCNJ13 mutations. *Ophthalmic Genet* 36, 79-84 (2015).
5. Perez-Roustit, S. et al. Leber Congenital Amaurosis with Large Retinal Pigment Clumps Caused by Compound Heterozygous Mutations in Kcnj13. *Retin Cases Brief Rep* (2016).
6. Hejtmancik, J. F. et al. Mutations in KCNJ13 cause autosomal-dominant snowflake vitreoretinal degeneration. *Am J Hum Genet* 82, 174-80 (2008).
7. Krapivinsky, G. et al. A novel inward rectifier K+ channel with unique pore properties. *Neuron* 20, 995-1005 (1998).
8. Derst, C. et al. Partial gene structure and assignment to chromosome 2q37 of the human inwardly rectifying K+ channel (Kir7.1) gene (KCNJ13). *Genomics* 54, 560-3 (1998).
9. McCloskey, C. et al. The inwardly rectifying K+ channel KIR7.1 controls uterine excitability throughout pregnancy. *EMBO Mol Med* 6, 1161-74 (2014).
10. Ghamari-Langroudi, M. et al. G-protein-independent coupling of MC4R to Kir7.1 in hypothalamic neurons. *Nature* (2015).
11. Shahi, P. K. et al. Abnormal Electroretinogram after Kir7.1 Channel Suppression Suggests Role in Retinal Electrophysiology. *Sci Rep* 7, 10651 (2017).
12. Singh, R. et al. iPS cell modeling of Best disease: insights into the pathophysiology of an inherited macular degeneration. *Hum Mol Genet* 22, 593-607 (2013).
13. Yang, D., Pan, A., Swaminathan, A., Kumar, G. & Hughes, B. A. Expression and localization of the inwardly rectifying potassium channel Kir7.1 in native bovine retinal pigment epithelium. *Invest Ophthalmol Vis Sci* 44, 3178-85 (2003).
14. Shimura, M. et al. Expression and permeation properties of the K(+) channel Kir7.1 in the retinal pigment epithelium. *J Physiol* 531, 329-46 (2001).
15. Nudelman, I. et al. Repairing faulty genes by aminoglycosides: development of new derivatives of geneticin (G418) with enhanced suppression of diseases-causing nonsense mutations. *Bioorg Med Chem* 18, 3735-46 (2010).
16. Goldmann, T. et al. A comparative evaluation of NB30, NB54 and PTC124 in translational read-through efficacy for treatment of an USH1C nonsense mutation. *EMBO Mol Med* 4, 1186-99 (2012).
17. Ramsden, C. M. et al. Rescue of the MERTK phagocytic defect in a human iPSC disease model using translational read-through inducing drugs. *Sci Rep* 7, 51 (2017).
18. Bennett, J. et al. Safety and durability of effect of contralateral-eye administration of AAV2 gene therapy in patients with childhood-onset blindness caused by RPE65 mutations: a follow-on phase 1 trial. *Lancet* 388, 661-72 (2016).
19. Dalkara, D., Goureau, O., Marazova, K. & Sahel, J. A. Let There Be Light: Gene and Cell Therapy for Blindness. *Hum Gene Ther* 27, 134-47 (2016).
20. White, M., Whittaker, R., Gandara, C. & Stoll, E. A. A Guide to Approaching Regulatory Considerations for Lentiviral-Mediated Gene Therapies. *Hum Gene Ther Methods* 28, 163-176 (2017).

Example 2—Kir7.1 Gene-Therapy in Cell Culture Models and In Vivo

Figure 8:
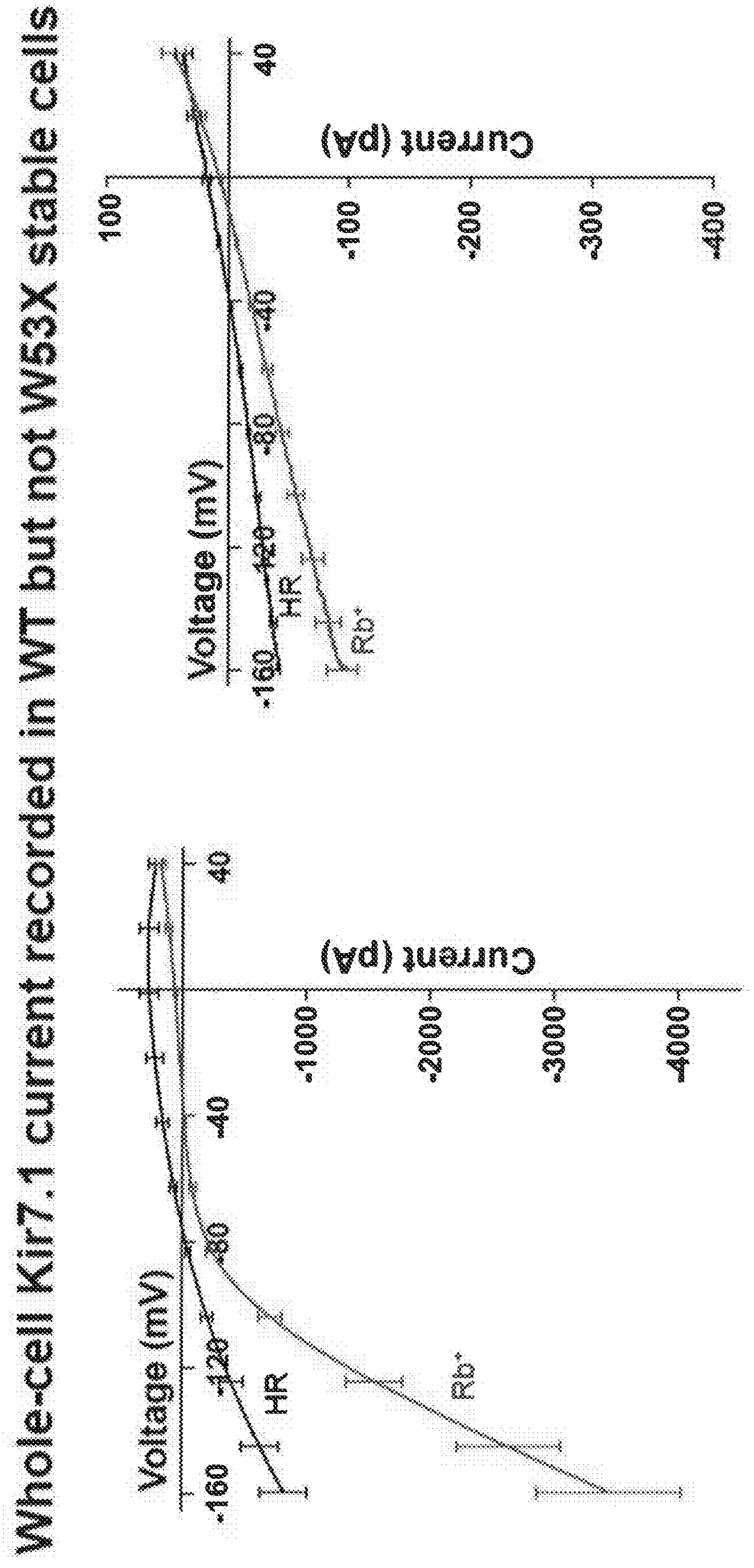
FIG. 8 shows whole-cell current voltage relationship from wildtype (left panel) and W53X mutant (right panel) stable cells. Inwardly rectifying K+ current (black trace) in the wildtype stable cell was significantly increased by Rb+ (red trace). In the W53X mutant stable cells on the right, neither K+ nor Rb+ current was recorded (p=1.05E-0.5).

To test the efficacy of gene therapy in a cell culture model of LCA16, we tested the ability of AAV-Kir7.1 to rescue the physiological defects in CHO cells harboring a W53×mutation in the Kcnj13 gene. FIG. 8 shows whole-cell current voltage relationship from wildtype (left panel) and W53× mutant (right panel) stable cells. Inwardly rectifying K+ current (black trace) in the wildtype stable cell was significantly increased by Rb+ (red trace). In the W53×mutant stable cells on the right, neither K+ nor Rb+ current was recorded (p=1.05E-0.5).

Figures 9A, 9B, 9C, 9D, 9E:
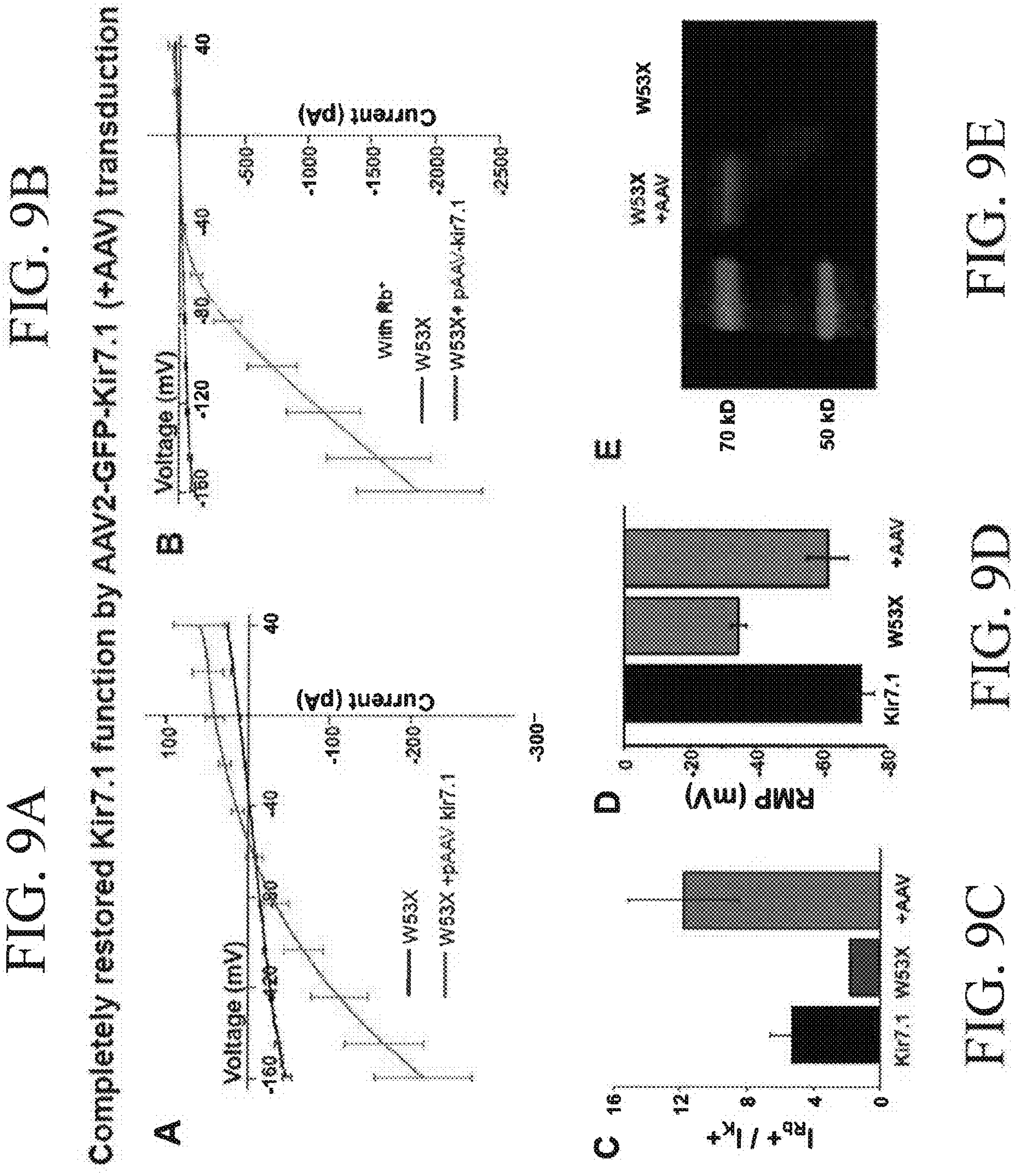
FIG. 9A-9E shows gene augmentation of W53X mutant expressing CHO cells had recovery of average inwardly rectifying K+ current (FIG. 9A. IV plot in red trace) compared to no current before (FIG. 9A. plot in black trace).

FIG. 9 shows gene augmentation of W53×mutant expressing CHO cells had recovery of average inwardly rectifying K+ current (FIG. 9A. IV plot in red trace) compared to no current before (FIG. 9A. plot in black trace). (FIG. 9B) Average higher Rb+ current (red trace) in W53× mutant expressing cells after gene augmentation. (FIG. 9C) Net increase in Rb+ permeability increased (Blue) through Kir7.1 channel after gene augmentation. (FIG. 9D) Complete recovery of resting membrane potential (RMP) after AAV-Kir7.1 transduction of W53×expressing cells represented as blue box. (FIG. 9E) Western blot results showing expression of full length protein product after gene augmentation in lane W53X+AAV (red band).

FIG. 10 shows Kir7.1 expression (green) in W53×mutant line after gene augmentation through AAV-Kir7.1 (FIG. 10A). (FIG. 10B) A higher magnification image shows membrane localization of the Kir7.1 protein alongside membrane marker WGA-Alexa 594. In the lower panel is the line scan for red and green showing membrane marker and Kir7.1 co-localize.

Figure 11:
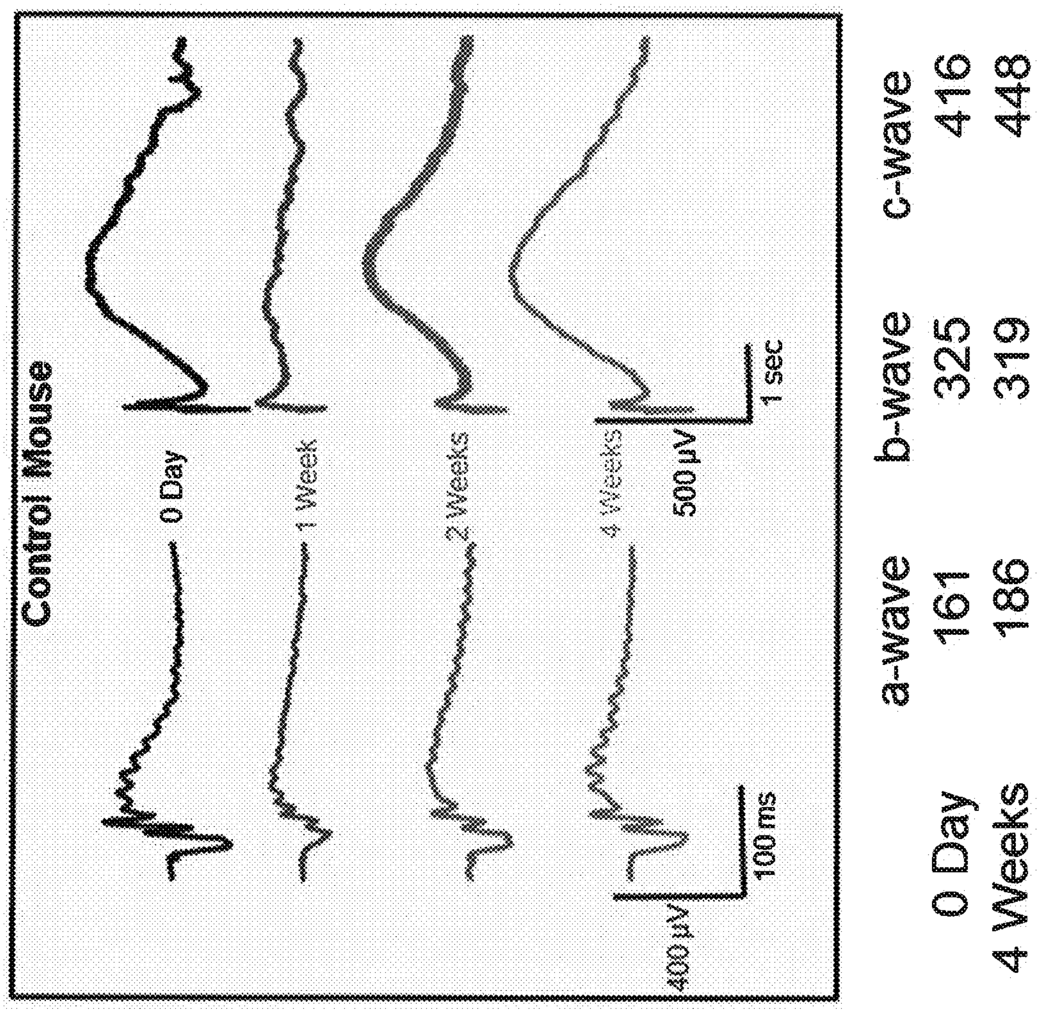
FIG. 11 shows Kir7.1 gene-therapy in vivo. On the left is a control mouse showing normal wave form of electroretinogram and no change after gene augmentation. In the middle is a conditional knock out mice showing no c-wave in the right black trace. This wave which directly depends on Kir7.1 expression is completely recovered 4 weeks after gene therapy. Average result is shown in box plot with significant recovery of c-wave in experimental gene therapy.
Figure 11:
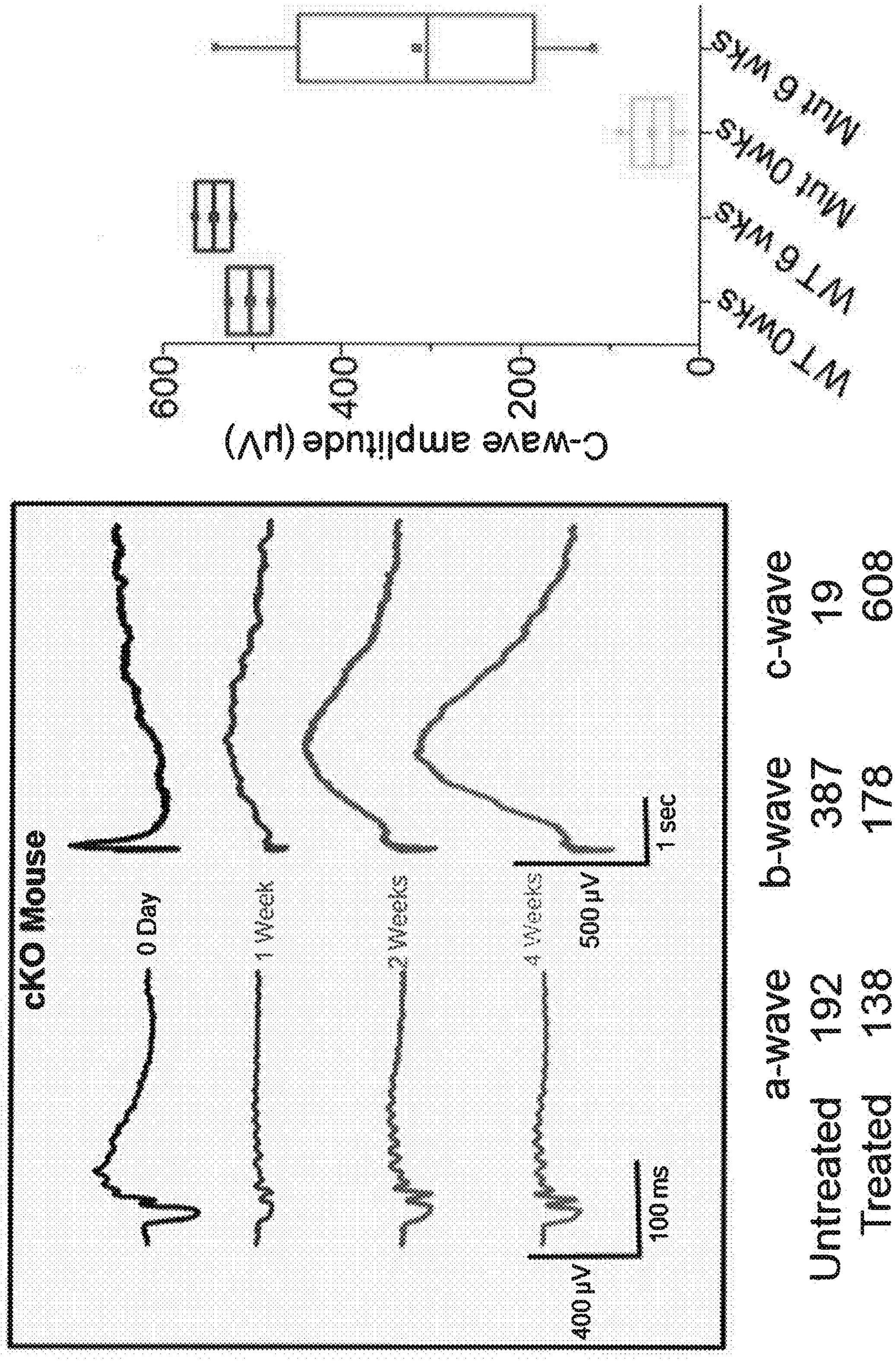

To test the efficacy of gene therapy in vivo, both wild-type and a mouse lacking the Kcnj13 gene were tested. In FIG. 11 left box is an example of a wild type mouse that received 2 μl of Lenti-EF1a-eGFPKir7.1 by sub-retinal injection. Electrophysiological results are obtained before (black trace) and 1 (blue trace), 2 (red trace), and 4 (green trace) weeks post injection. In FIG. 11 left box, retina responses recorded as normal a- and b-wave are shown on the left and RPE cell response c-wave is shown on the right. Only in the 1$^{st}$ week after injection there was a reduction in retina response otherwise there was hardly any effect of gene therapy on electrophysiological outcome. In FIG. 11 right box we show results from mice lacking Kcnj13 gene that received 2 μl of Lenti-EF1a-eGFPKir7.1. On the right panel is the RPE response of c-wave, that was completely abolished in these mice (black trace) with slight reduction in a- and b-wave shown in the left panel. Immediately post gene-therapy, we noticed increase in c-wave response starting a week after injection (blue trace on the right panel). Traces show continued increase in c-wave during the following 2 (red trace) and 4 (green) weeks post gene therapy. Average measurements in 4 wild-type and four mice lacking Kcnj13 gene is shown as box plot with significant recovery in c-wave and no effect on wild-type mice vision. Numbers below the figure shows actual amplitude of a-, b- and c-wave measurements in wild-type and mice lacking Kcnj13.

Figures 14A, 14B:
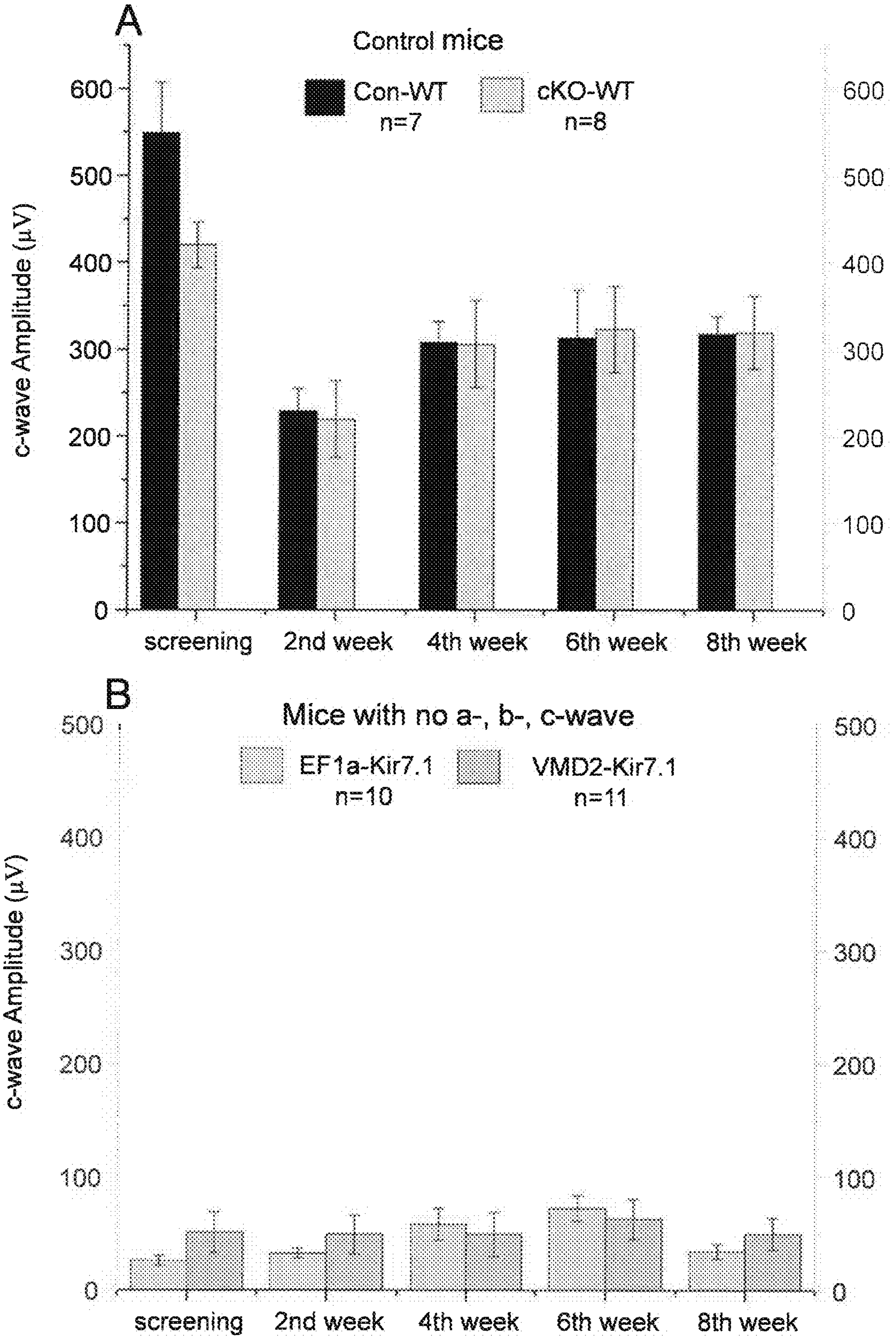
FIGS. 14A-14F demonstrates functional recovery of Retinal Pigment Epithelial (RPE) cells lacking Kir7.1 protein after gene therapy.
Figure 14C:
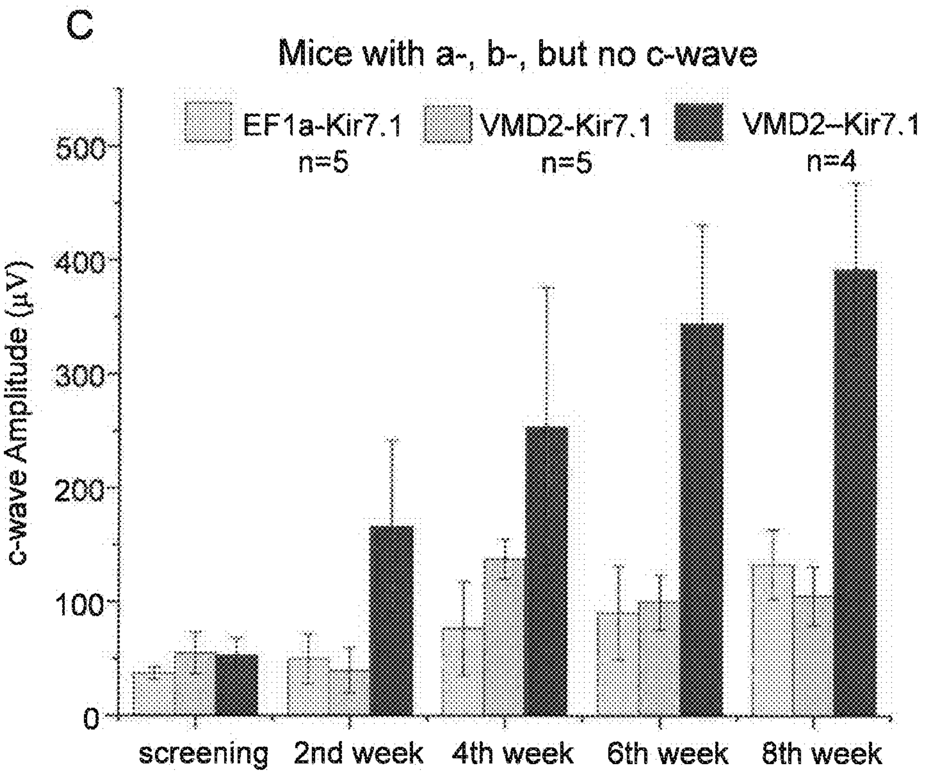
Figures 14D, 14E, 14F:
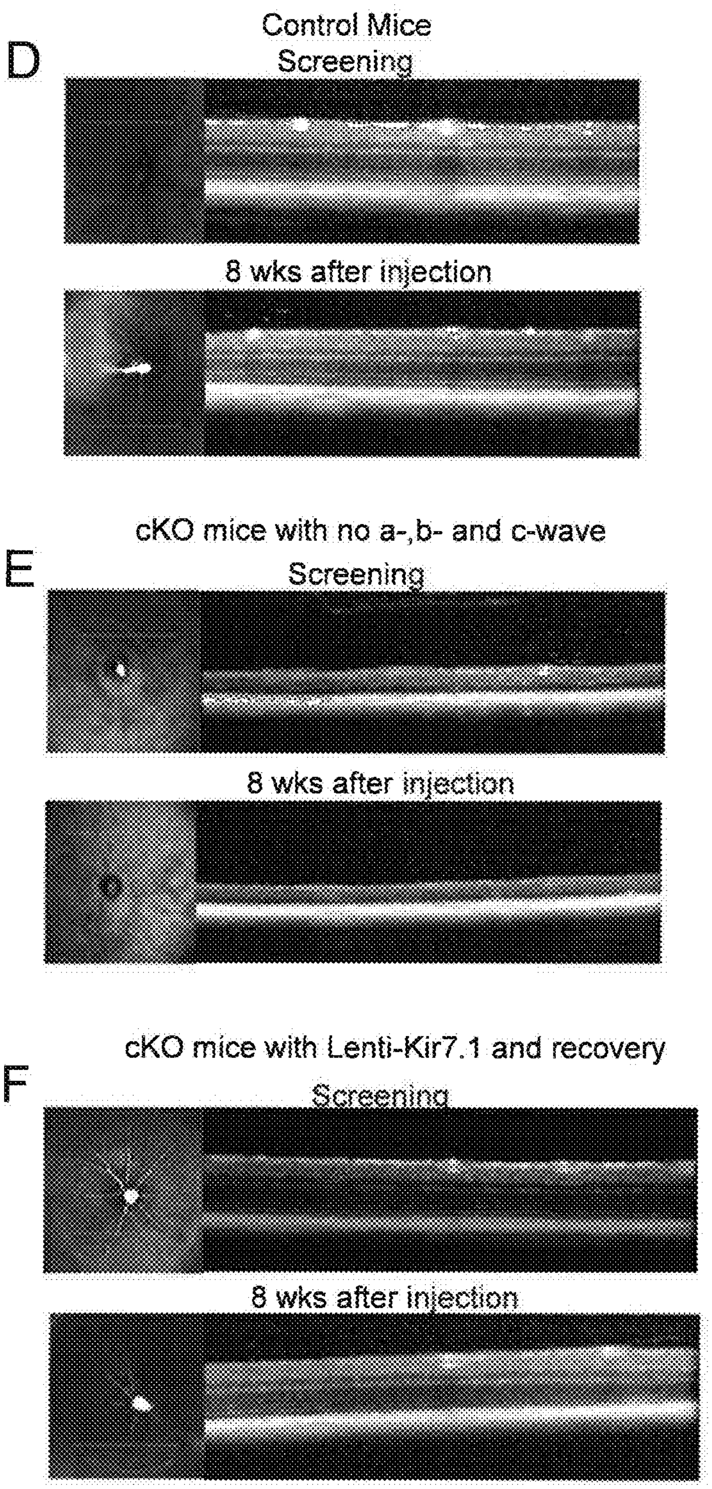
Figure 15A:
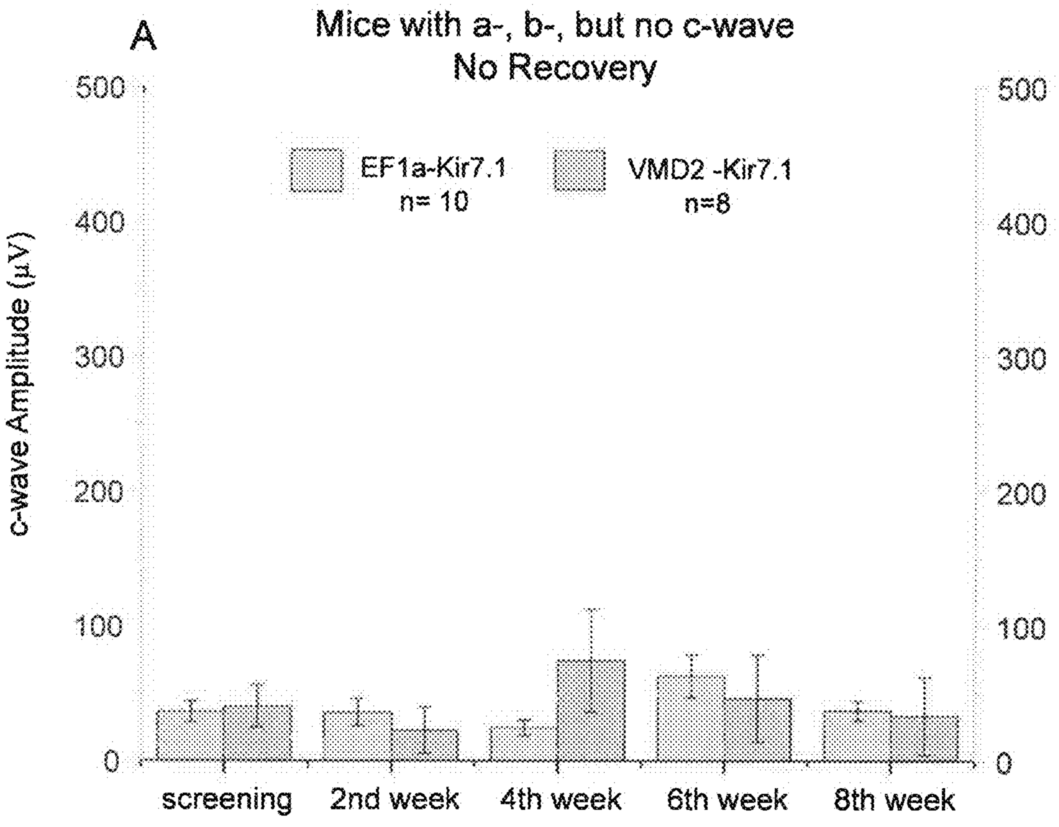
FIGS. 15A-15E demonstrates results of a subset of mice that did not show c-wave recovery.
Figures 15B, 15C, 15D, 15E:
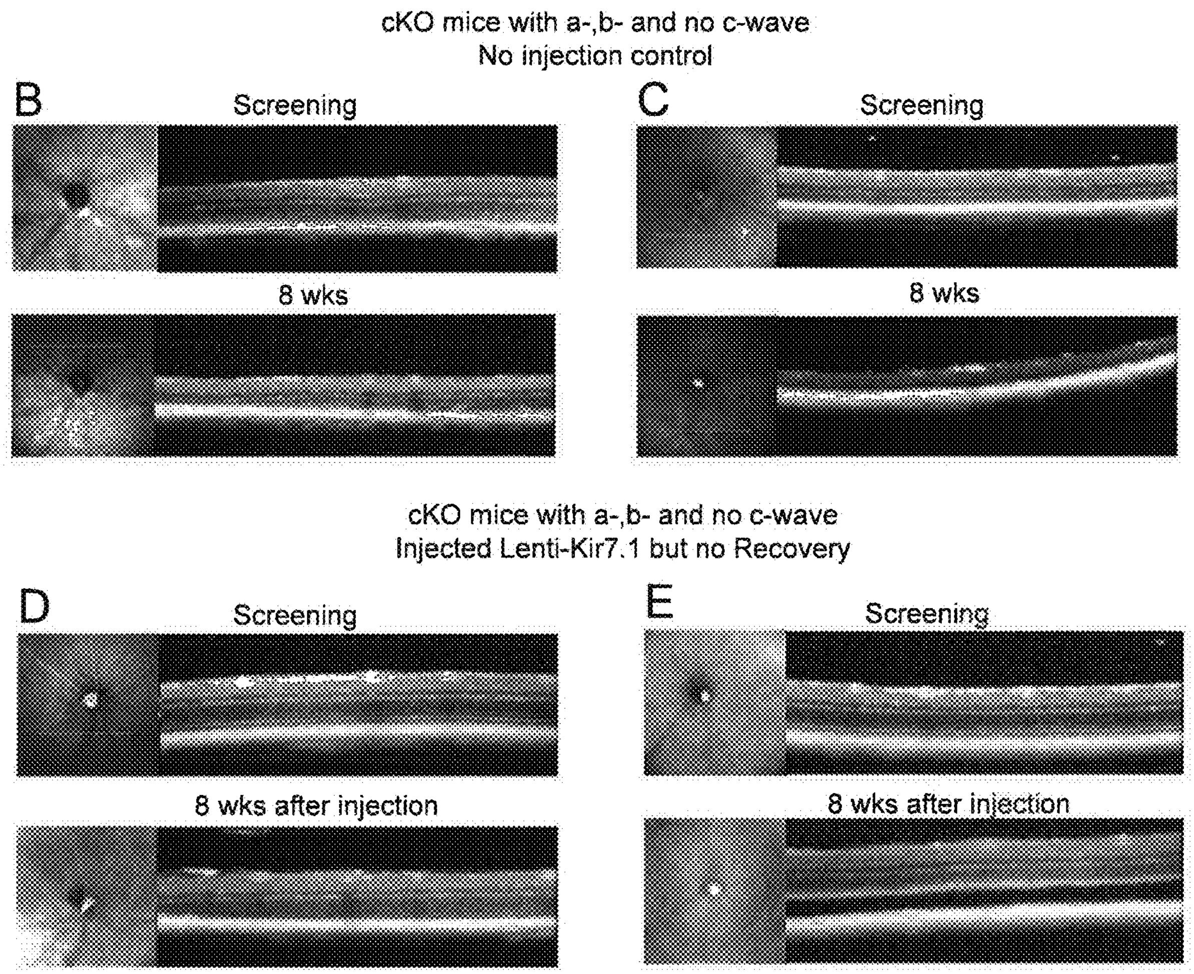

Further, FIGS. 14A-F show functional recovery of Retinal Pigment Epithelial (RPE) cells lacking Kir7.1 protein after gene therapy in the cKO mouse model. FIG. 14A shows injection control on WT mice and the cKO control mice depicting the RPE response functional after 8 weeks with PBS injection. ERG response from the Kir7.1 cKO mice which showed no a-, b- and c-wave during the screening (FIG. 14B). Delivery of the Kir7.1 with lentivirus carrying either constitutive EF1a promoter or RPE specific VMD2 promoter failed to rescue the RPE function due to the severe phenotype as both RPE and photoreceptors were degenerated C-wave from RPE is recovered in the cKO mice, by subretinal delivery of lentivirus carrying kcnj13 gene driven by EF1a and VMD2 promoter, where the photoreceptors were not degenerated but had no response from the RPE cells during screening (FIG. 14C). FIGS. 14D-F show representative optical coherence tomography (OCT) images showing the retinal structure from the control mice, cKO mice (no-a-,b-c-wave) with no recovery and c-wave recovered mice (a-, b- but no-c-wave) during screening and post 8 weeks after lentiviral gene delivery, respectively. Thus, the in vivo data shows that expressing Kir 7.1 in RPE can restore vision in these deficient mice.

Material and Methods

Animals

To elucidate the physiological role of KCNJ13 gene in the RPE cells, in vivo, we used a strain that is lacking this gene. Vision in these mice was measured using electroretinography (ERG). The mice were housed and bred at the University of Wisconsin Biotron (Madison, WI)

Electroretinography

The mice were dark adapted overnight prior to performing ERG. The mice were anesthetized with Ketamine/Xylazine (80:16 mg/kg) cocktail injected intra-peritoneally. While maintaining the body temperature at 37° C. with a heating pad, the pupil of the mouse was dilated with a drop of tropicamide (Bausch+Lomb, Rochester, NY). ERGs were performed using the Espion recording system (Diagnosys) by placing a corneal contact lens (Ocusciences Inc., MO) on the dilated eyes along with Gonak, a 2.5% hypromellose ophthalmic demulcent solution (GONIOVISC, HUB Pharmaceuticals, LLC, CA). A reference and the ground electrode were placed in the mouth and the back respectively. The protocol for ERG consisted of recordings from flash intensities from 0.1 to 30 cd·s·m-2 and 60 Hz line noise was removed using the filter. For c-wave measurements, we used a 5 msec flash of 25 cd·s·m-2 intensity to acquire data during a 5 sec interval. ERG analysis was performed on the mice before and after the sub-retinal injection.

Sub-Retinal Injection

The KCNJ13 knockout mice with no c-waveforms were used for this purpose. The mice were maintained under tightly controlled temperature (23±5° C.), humidity (40-50%) and light/dark (12/12 h) cycle conditions in 200 lux light environment. Prior to the injection, the mice were anesthetized and pupils were dilated as described above. 2 μl of Lentivirus or Adeno-associated virus (AAV) carrying the functional full length KCNJ13 gene fused with eGFP and driven by EF1a or VMD2 promoters were delivered to the RPE cells through sub-retinal injection using a 10 mm 34 gauge needle. We used a 10 μl Nanofil syringe and UMP3, NanoFil RPE-KIT and Micro4 controller (World precision Instruments, Inc., Sarasota, FL). ERG was performed on these mice at 1 wk, 2 wks, 4 wks and 8 wks post injection and data were analyzed.

Transgene Expression Detection eGFP fluorescence was detected using confocal microscopy after preparing a flat mount of the isolated RPE. Eyes from the Lentivirus/AAV carrying eGFP-KCNJ13 gene injected mice were retrieved one week post injection. Enucleated eyes from the sacrificed mice were rinsed twice with PBS, a puncture was made at or a serrata with a 28 gauge needle and the eyes were opened along the corneal incisions. The lens was then carefully removed. The eye cup was flattened making incisions radially to the center resulting in a "starfish" appearance. The retina was then separated gently from the RPE layer. The separated RPE and retina were flat mounted on the cover-glass slide and were imaged with NIS-Elements using a Nikon C2 confocal microscope (Nikon Instruments Inc., Mellville, NY). We used 488 nm Diode Lasers for green excitation and images were captured by Low Noise PMT C2 detectors in a Plan Apo VC 20×/0.75, 1 mm WD lens.

Example 3—Preparation of AAV Viral Vectors for Delivery of Kir7.1 Protein

AAV Viral Vector Construction

Figure 12:
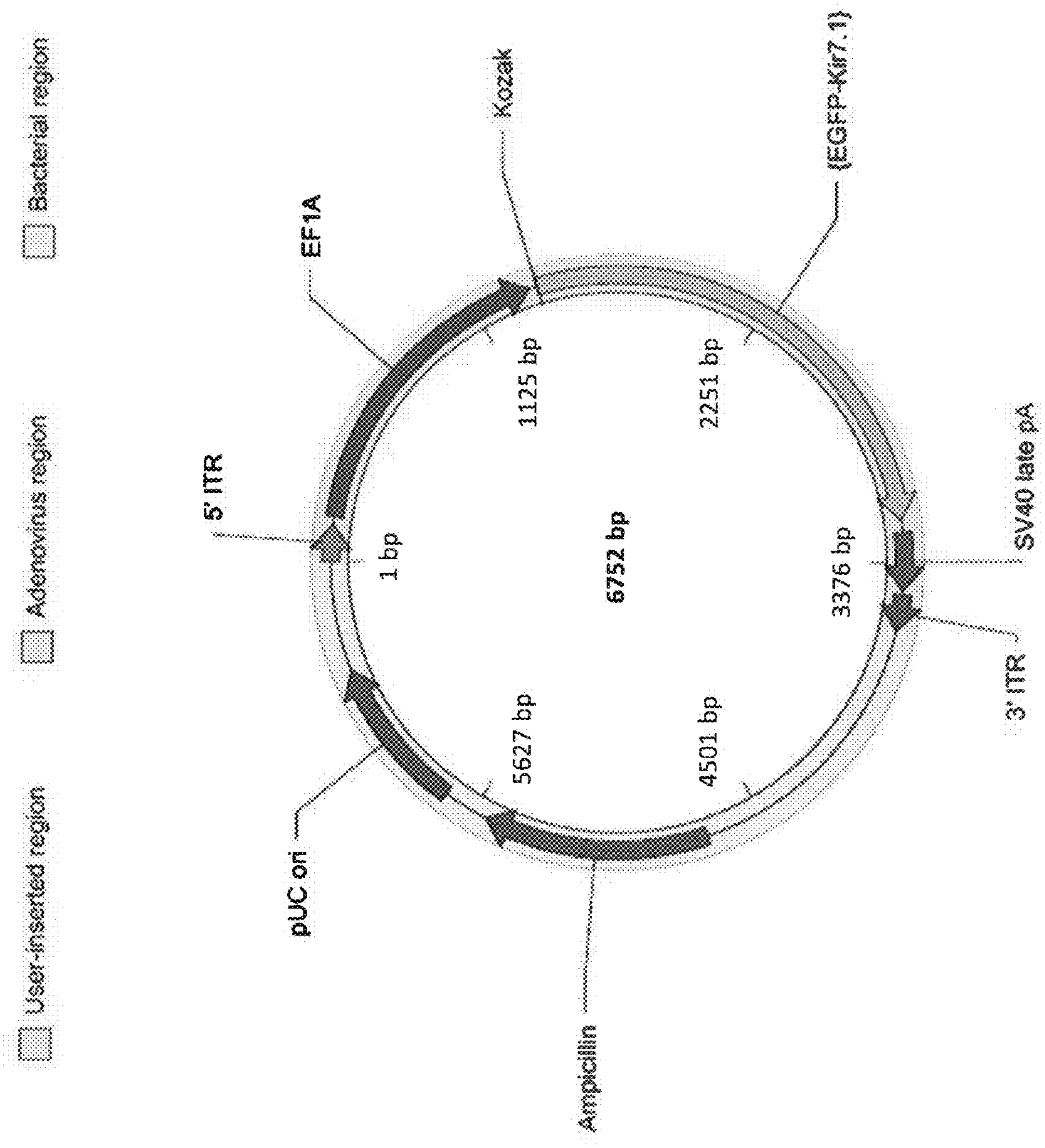
FIG. 12 shows a vector map for an exemplary AAV viral vector for delivery of a Kir7.1 protein.

AAV vectors for the delivery of Kir7.1 protein were produced using VectorBuilder software of Cyagen Biosciences and packaging services from Cyagen Biosciences. The following Tables 1-3 and FIG. 12 summarize the construction of AAV vectors that successfully rescued physiological defects in a Kcnj13 gene.

TABLE 1

| Vector Summary | |
|---|---|
| Vector ID | VB161122-1168yrz |
| Vector Name (official) | pAAV[Exp]-EFIA > [EGFP-Kir7.1] |
| Date Created (Pacific Time) | 2016 Nov. 22 |
| Size | 6752 bp |
| Vector Type | Adeno-associated virus gene expression vector |
| Inserted Promoter | EFIA |
| Inserted ORF | [EGFP-Kir7.1] |
| Copy Number | High |
| Bacterial Resistance | Ampicillin |
| Cloning Host | Stb13 |

Table 2 and Table 3 in FIG. 16 have the color-coded segments and sequence for the AAV vector encoding Kir7.1 (SEQ ID NO.9).

AAV Viral Vector Packaging

The adeno-associated virus (AAV) vector system is a popular and versatile tool for in vitro and in vivo gene delivery. AAV is effective in transducing many mammalian cell types, and, unlike adenovirus, has very low immunogenicity, being almost entirely nonpathogenic in vivo. This makes AAV the ideal viral vector system for many animal studies.

An AAV vector is first constructed as a plasmid in *E. coli*. It is then transfected into packaging cells along with helper plasmids, where the region of the vector between the two inverted terminal repeats (ITRs) is packaged into live virus. When the virus is added to target cells, the double-stranded linear DNA genome is delivered into cells where it enters the nucleus and remains as episomal DNA without integration into the host genome. Any gene(s) placed in-between the two ITRs are introduced into target cells along with the rest of viral genome.

A major practical advantage of AAV is that in most cases AAV can be handled in biosafety level 1 (BSL1) facilities. This is due to AAV being inherently replication-deficient, producing little or no inflammation, and causing no known human disease.

Many strains of AAV have been identified in nature. They are divided into different serotypes based on different antigenicity of the capsid protein on the viral surface. Different serotypes can render the virus with different tissue tropism (i.e. tissue specificity of infection). Different AAV serotypes have tropism for different cell types, and certain cell types may be hard to transduce by any serotype. See, e.g., *Curr Opin Pharmacol.* 24:59-67 (2015). We found that the AAV2 serotype may be used to effectively transduce retinal pigment epithelium (RPE) cells either in vitro or in vivo. See, e.g., Examples 1 and 2.

Figure 13:
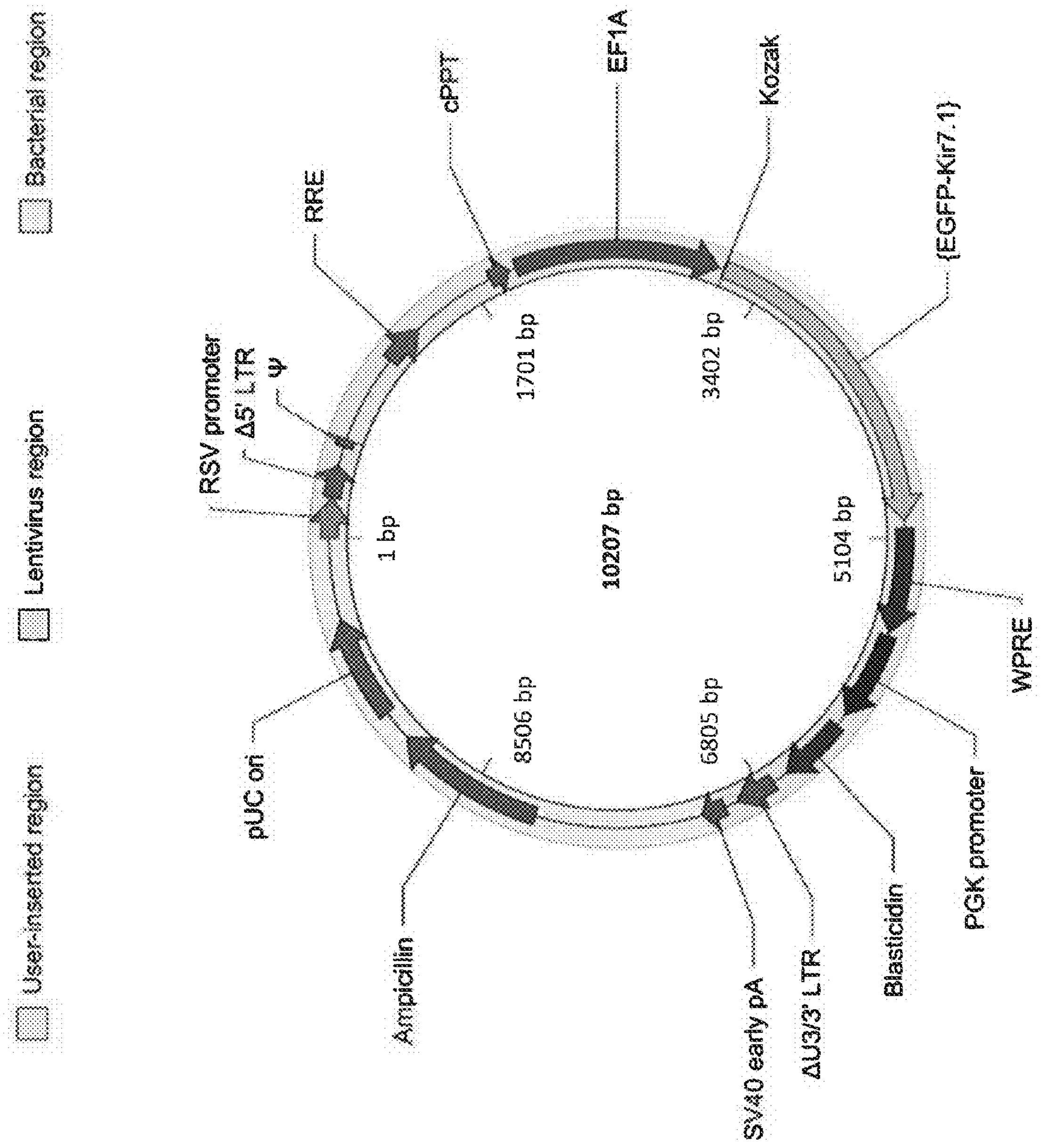
FIG. 13 shows a vector map for an exemplary Lentivirus viral vector for delivery of a Kir7.1 protein.

Example 4—Preparation of Lentivirus Viral Vectors for Delivery of Kir7.1 Protein Lentivirus Viral Vector Construction Lentivirus vectors for the delivery of Kir7.1 protein were produced using VectorBuilder software of Cyagen Biosciences and packaging services from Cyagen Biosciences. The following Tables 4-6 and FIG. 13 summarize the construction of Lentivirus vectors that successfully rescued physiological defects in the KCNJ13 gene.

TABLE 4

| Vector Summary | |
|---|---|
| Vector ID | VB161020-1047mdf |
| Vector Name (official) | pLV[Exp]-Bsd-EFIA > [EGFP-Kir7.1] |
| Date Created (Pacific Time) | 2016 Oct. 19 |
| Size | 10207 bp |
| Vector Type | Lentivirus gene expression vector (3rd generation) |
| Inserted Promoter | EFIA |
| Inserted ORF | [EGFP-Kir7.1] |
| Inserted Marker | Bsd |
| Copy Number | High |
| Bacterial Resistance | Ampicillin |
| Cloning Host | Stb13 |

Table 5 and 6 found in FIG. 17 provide the color index and sequence listing for the lentiviral vector (SEQ ID NO 10).

Lentivirus Viral Vector Packaging

The lentiviral vector system is a highly efficient vehicle for introducing genes permanently into mammalian cells. Lentiviral vectors are derived from HIV, which is a member of the retrovirus family. Wildtype lentivirus has a plus-strand linear RNA genome.

A lentiviral vector is first constructed as a plasmid in *E. coli*. It is then transfected into packaging cells along with several helper plasmids. Inside the packaging cells, vector DNA located between the two long terminal repeats (LTRs) is transcribed into RNA, and viral proteins expressed by the helper plasmids further package the RNA into virus. Live virus is then released into the supernatant, which can be used to infect target cells directly or after concentration.

By design, lentiviral vectors lack the genes required for viral packaging and transduction (these genes are instead carried by helper plasmids used during virus packaging). As a result, virus produced from lentiviral vectors has the important safety feature of being replication incompetent (meaning that they can transduce target cells but cannot replicate in them).

The Lentivirus viral vectors described herein may be derived from the third-generation lentiviral vector system. See, e.g., *J Virol.* 72:8463 (1998). It is optimized for high copy number replication in *E. coli*, high-titer packaging of live virus, efficient viral transduction of a wide range of cells, efficient vector integration into the host genome, and high-level transgene expression.

The packaging system for the lentivirus viral vectors described herein may add the VSV-G envelop protein to the viral surface. This protein has broad tropism and we found that it may help transduce retinal pigment epithelium (RPE) cells either in vitro or in vivo.

We claim:

1. A gene therapy vector comprising a VMD2 promoter operably connected to a polynucleotide encoding a Kir7.1 polypeptide, wherein the VMD2 promoter comprises SEQ ID NO: 4 and is active in the retinal pigment epithelium (RPE) in the eye of a subject, and wherein the Kir7.1 polypeptide comprises SEQ ID NO: 1.

2. The gene therapy vector of claim 1, wherein the gene therapy vector is a viral vector.

3. The gene therapy vector of claim 2, wherein the viral vector is selected from the group consisting of a retroviral vector, an adeno-associated viral (AAV) vector, and an adenoviral vector.

4. The gene therapy vector of claim 3, wherein the viral vector is a lentiviral vector.

5. The gene therapy vector of claim 3, wherein the viral vector is an adeno-associated viral vector (AAV).

6. The gene therapy vector of claim 5, wherein the AAV vector is an AAV2 vector.

7. The gene therapy vector of claim 2, wherein the viral vector is a virus particle and comprises a VSV-G envelope protein.

8. A lentiviral vector or adeno-associated viral (AAV) vector comprising SEQ ID NO: 6 (VMD2-Kir7.1).

9. A therapeutic composition comprising the gene therapy vector of claim 1 and a pharmaceutically-acceptable carrier.

10. A method of treating a subject having a condition associated with insufficient expression or function of a Kir7.1 polypeptide comprising subretinally administering between $10^6$ and $10^{14}$ copies of the gene therapy vector of claim 1 to at least one eye of the subject, wherein the condition is Leber congenital amaurosis 16 (LCA16), retinitis pigmentosa, or snowflake vitreoretinal degeneration (SVD).

11. The method of claim 10, wherein the condition is associated with at least one loss-of-function mutation in a KCNJ13 gene.

12. The method of claim 11, wherein the at least one loss-of-function mutation results in a substitution to SEQ ID NO: 1 selected from the group consisting of W53Ter, Q116R, I120T, T153I, R162Q, R166Ter, L241P, E276A, S105I, and G219Ter.

13. The method of claim 10, wherein the subject is human.

14. A method of expressing a Kir7.1 polypeptide in a retinal pigment epithelium (RPE) cell comprising contacting the RPE cell with the gene therapy vector of claim 1 (i) in vitro or (ii) in vivo by subretinal administration of between $10^6$ and $10^{14}$ copies of the gene therapy vector.

15. The method of claim 10, wherein a c-wave of the eye of the subject is increased after administration of the gene therapy vector in the eye of the subject as compared to the response in the eye of the subject prior to administration of the gene therapy vector.

16. The method of claim 10, wherein the vision of the subject is restored.

* * * * *

SEQUENCE LISTING

<160> NUMBER OF SEQ ID NOS: 20

<210> SEQ ID NO 1
<211> LENGTH: 360
<212> TYPE: PRT
<213> ORGANISM: Homo sapiens

<400> SEQUENCE: 1

Met Asp Ser Ser Asn Cys Lys Val Ile Ala Pro Leu Leu Ser Gln Arg
1 5 10 15

Tyr Arg Arg Met Val Thr Lys Asp Gly His Ser Thr Leu Gln Met Asp
20 25 30

Gly Ala Gln Arg Gly Leu Ala Tyr Leu Arg Asp Ala Trp Gly Ile Leu
35 40 45

Met Asp Met Arg Trp Arg Trp Met Met Leu Val Phe Ser Ala Ser Phe
50 55 60

Val Val His Trp Leu Val Phe Ala Val Leu Trp Tyr Val Leu Ala Glu
65 70 75 80

Met Asn Gly Asp Leu Glu Leu Asp His Asp Ala Pro Pro Glu Asn His
85 90 95

Thr Ile Cys Val Lys Tyr Ile Thr Ser Phe Thr Ala Ala Phe Ser Phe
100 105 110

Ser Leu Glu Thr Gln Leu Thr Ile Gly Tyr Gly Thr Met Phe Pro Ser
115 120 125

Gly Asp Cys Pro Ser Ala Ile Ala Leu Leu Ala Ile Gln Met Leu Leu
130 135 140

Gly Leu Met Leu Glu Ala Phe Ile Thr Gly Ala Phe Val Ala Lys Ile
145 150 155 160

Ala Arg Pro Lys Asn Arg Ala Phe Ser Ile Arg Phe Thr Asp Thr Ala
165 170 175

Val Val Ala His Met Asp Gly Lys Pro Asn Leu Ile Phe Gln Val Ala
180 185 190

Asn Thr Arg Pro Ser Pro Leu Thr Ser Val Arg Val Ser Ala Val Leu
195 200 205

Tyr Gln Glu Arg Glu Asn Gly Lys Leu Tyr Gln Thr Ser Val Asp Phe
210 215 220

His Leu Asp Gly Ile Ser Ser Asp Glu Cys Pro Phe Phe Ile Phe Pro
225 230 235 240

Leu Thr Tyr Tyr His Ser Ile Thr Pro Ser Ser Pro Leu Ala Thr Leu
245 250 255

Leu Gln His Glu Asn Pro Ser His Phe Glu Leu Val Val Phe Leu Ser
260 265 270

Ala Met Gln Glu Gly Thr Gly Glu Ile Cys Gln Arg Arg Thr Ser Tyr
275 280 285

Leu Pro Ser Glu Ile Met Leu His His Cys Phe Ala Ser Leu Leu Thr
290 295 300

Arg Gly Ser Lys Gly Glu Tyr Gln Ile Lys Met Glu Asn Phe Asp Lys
305 310 315 320

Thr Val Pro Glu Phe Pro Thr Pro Leu Val Ser Lys Ser Pro Asn Arg
325 330 335

Thr Asp Leu Asp Ile His Ile Asn Gly Gln Ser Ile Asp Asn Phe Gln
340 345 350

Ile Ser Glu Thr Gly Leu Thr Glu
355 360

<210> SEQ ID NO 2
<211> LENGTH: 1083
<212> TYPE: DNA
<213> ORGANISM: Homo sapiens

<400> SEQUENCE: 2
atggacagca gtaattgcaa agttattgct cctctcctaa gtcaaagata ccggaggatg 60
gtcaccaagg atggccacag cacacttcaa atggatggcg ctcaaagagg tcttgcatat 120
cttcgagatg cttggggaat cctaatggac atgcgctggc gttggatgat gttggtcttt 180
tctgcttctt ttgttgtcca ctggcttgtc tttgcagtgc tctggtatgt tctggctgag 240
atgaatggtg atctggaact agatcatgat gccccacctg aaaaccacac tatctgtgtc 300
aagtatatca ccagtttcac agctgcattc tccttctccc tggagacaca actcacaatt 360
ggttatggta ccatgttccc cagtggtgac tgtccaagtg caatcgcctt acttgccata 420
caaatgctcc taggcctcat gctagaggct tttatcacag gtgcttttgt ggcgaagatt 480
gcccggccaa aaaatcgagc tttttcaatt cgctttactg acatagcagt agtagctcac 540
atggatggca aacctaatct tatcttccaa gtggccaaca cccgacctag ccctctaacc 600
agtgtccggg tctcagctgt actctatcag gaaagagaaa atggcaaact ctaccagacc 660
agtgtggatt tccaccttga tggcatcagt tctgacgaat gtccattctt catctttcca 720
ctaacgtact atcactccat tacaccatca agtcctctgg ctactctgct ccagcatgaa 780
aatccttctc actttgaatt agttgtattc ctttcagcaa tgcaggaggg cactggagaa 840
atatgccaaa ggaggacatc ctacctacag tctgaaatca tgttacatca ctgttttgca 900
tctctgttga cccgaggttc caaatgtgaa tatcaaatca agatggagaa ttttgacaag 960
actgtccctg aatttccaac tcctctggtt tctaaaagcc caaacaggac tgacctggat 1020
atccacatca atggacaaag cattgacaat tttcagatct ctgaaacagg actgacagaa 1080
taa 1083

<210> SEQ ID NO 3
<211> LENGTH: 1179
<212> TYPE: DNA
<213> ORGANISM: Homo sapiens

<400> SEQUENCE: 3
ggctccggtg cccgtcagtg ggcagagcgc acatcgccca cagtccccga gaagttgggg 60
ggaggggtcg gcaattgaac cggtgcctag agaaggtggc gcggggtaaa ctgggaaagt 120
gatgtcgtgt actggctccg cctttttccc gagggtgggg gagaaccgta tataagtgca 180
gtagtcgccg tgaacgttct ttttcgcaac gggtttgccg ccagaacaca ggtaagtgcc 240
gtgtgtggtt cccgcgggcc tggcctcttt acgggttatg gcccttgcgt gccttgaatt 300
acttccacct ggctgcagta cgtgattctt gatcccgagc ttcgggttgg aagtgggtgg 360
gagagttcga ggccttgcgc ttaaggagcc ccttcgcctc gtgcttgagt tgaggcctgg 420
cctgggcgct ggggccgccg cgtgcgaatc tggtggcacc ttcgcgcctg tctcgctgct 480
ttcgataagt ctctagccat ttaaaatttt tgatgacctg ctgcgacgct ttttttctgg 540
caagatagtc ttgtaaatgc gggccaagat ctgcacactg gtatttcggt ttttggggcc 600
gcgggcggcg acggggcccg tgcgtcccag cgcacatgtt cggcgaggcg gggcctgcga 660
gcgcggccac cgagaatcgg acgggggtag tctcaagctg gccggcctgc tctggtgcct 720
ggtctcgcgc cgccgtgtat cgccccgccc tgggcggcaa ggctggcccg gtcggcacca 780

```
gttgcgtgag cggaaagatg gccgcttccc ggccctgctg cagggagctc aaaatggagg    840
acgcggcgct cgggagagcg ggcgggtgag tcacccacac aaaggaaaag ggcctttccg    900
tcctcagccg tcgcttcatg tgactccacg gagtaccggg cgccgtccag gcacctcgat    960
tagttctcga gcttttggag tacgtcgtct ttaggttggg gggaggggtt ttatgcgatg   1020
gagtttcccc acactgagtg ggtggagact gaagttaggc cagcttggca cttgatgtaa   1080
ttctccttgg aatttgccct ttttgagttt ggatcttggt tcattctcaa gcctcagaca   1140
gtggttcaaa gtttttttct tccatttcag gtgtcgtga                           1179
```

<210> SEQ ID NO 4
<211> LENGTH: 626
<212> TYPE: DNA
<213> ORGANISM: Homo sapiens

<400> SEQUENCE: 4

```
aattctgtca ttttactagg gtgatgaaat tcccaagcaa caccatcctt ttcagataag     60
ggcactgagg ctgagagagg agctgaaacc tacccggggt caccacacac aggtggcaag    120
gctgggacca gaaaccagga ctgttgactg cagcccggta ttcattcttt ccatagccca    180
cagggctgtc aaagacccca gggcctagtc agaggctcct ccttcctgga gagttcctgg    240
cacagaagtt gaagctcagc acagccccct aacccccaac tctctctgca aggcctcagg    300
ggtcagaaca ctggtggagc agatccttta gcctctggat tttagggcca tggtagaggg    360
ggtgttgccc taaattccag ccctggtctc agcccaacac cctccaagaa gaaattagag    420
gggccatggc caggctgtgc tagccgttgc ttctgagcag attacaagaa gggactaaga    480
caaggactcc tttgtggagg tcctggctta gggagtcaag tgacggcggc tcagcactca    540
cgtgggcagt gccagcctct aagagtgggc aggggcactg gccacagagt cccagggagt    600
cccaccagcc tagtcgccag gtcgac                                         626
```

<210> SEQ ID NO 5
<211> LENGTH: 3048
<212> TYPE: DNA
<213> ORGANISM: Artificial Sequence
<220> FEATURE:
<223> OTHER INFORMATION: synthetic

<400> SEQUENCE: 5

```
ggctccggtg cccgtcagtg ggcagagcgc acatcgccca cagtccccga gaagttgggg     60
ggaggggtcg gcaattgaac cggtgcctag agaaggtggc gcggggtaaa ctgggaaagt    120
gatgtcgtgt actggctccg cctttttccc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccacct ggctgcagta cgtgattctt gatcccgagc ttcgggttgg aagtgggtgg    360
gagagttcga ggccttgcgc ttaaggagcc ccttcgcctc gtgcttgagt tgaggcctgg    420
cctgggcgct ggggccgccg cgtgcgaatc tggtggcacc ttcgcgcctg tctcgctgct    480
ttcgataagt ctctagccat ttaaaatttt tgatgacctg ctgcgacgct ttttttctgg    540
caagatagtc ttgtaaatgc gggccaagat ctgcacactg gtatttcggt ttttggggcc    600
gcgggcggcg acggggcccg tgcgtcccag cgcacatgtt cggcgaggcg gggcctgcga    660
gcgcggccac cgagaatcgg acgggggtag tctcaagctg gccggcctgc tctggtgcct    720
```

-continued

```
ggtctcgcgc cgccgtgtat cgccccgccc tgggcggcaa ggctggcccg gtcggcacca    780
gttgcgtgag cggaaagatg gccgcttccc ggccctgctg cagggagctc aaaatggagg    840
acgcggcgct cgggagagcg ggcgggtgag tcacccacac aaaggaaaag ggcctttccg    900
tcctcagccg tcgcttcatg tgactccacg gagtaccggg cgccgtccag gcacctcgat    960
tagttctcga gcttttggag tacgtcgtct ttaggttggg gggaggggtt ttatgcgatg   1020
gagtttcccc acactgagtg ggtggagact gaagttaggc cagcttggca cttgatgtaa   1080
ttctccttgg aatttgccct ttttgagttt ggatcttggt tcattctcaa gcctcagaca   1140
gtggttcaaa gtttttttct tccatttcag gtgtcgtgac aagtttgtac aaaaaagcag   1200
gctgccacca tggtgagcaa gggcgaggag ctgttcaccg ggtggtgcc catcctggtc    1260
gagctggacg gcgacgtaaa cggccacaag ttcagcgtgt ccggcgaggg cgagggcgat   1320
gccacctacg gcaagctgac cctgaagttc atctgcacca ccggcaagct gcccgtgccc   1380
tggcccaccc tcgtgaccac cctgacctac ggcgtgcagt gcttcagccg ctaccccgac   1440
cacatgaagc agcacgactt cttcaagtcc gccatgcccg aaggctacgt ccaggagcgc   1500
accatcttct tcaaggacga cggcaactac aagacccgcg ccgaggtgaa gttcgagggc   1560
gacaccctgg tgaaccgcat cgagctgaag ggcatcgact tcaaggagga cggcaacatc   1620
ctggggcaca agctggagta caactacaac agccacaacg tctatatcat ggccgacaag   1680
cagaagaacg gcatcaaggt gaacttcaag atccgccaca acatcgagga cggcagcgtg   1740
cagctcgccg accactacca gcagaacacc cccatcggcg acggccccgt gctgctgccc   1800
gacaaccact acctgagcac ccagtccgcc ctgagcaaag accccaacga gaagcgcgat   1860
cacatggtcc tgctggagtt cgtgaccgcc gccgggatca ctctcggcat ggacgagctg   1920
tacaagtccg gactcagatc tcgagctcaa gcttcgaatt ctgacagcag taattgcaaa   1980
gttattgctc ctctcctaag tcaaagatac cggaggatgg tcaccaagga tggccacagc   2040
acacttcaaa tggatggcgc tcaaagaggt cttgcatatc ttcgagatgc ttggggaatc   2100
ctaatggaca tgcgctggcg ttggatgatg ttggtctttt ctgcttcttt tgttgtccac   2160
tggcttgtct ttgcagtgct ctggtatgtt ctggctgaga tgaatggtga tctggaacta   2220
gatcatgatg ccccacctga aaaccacact atctgtgtca agtatatcac cagtttcaca   2280
gctgcattct ccttctccct ggagacacaa ctcacaattg gttatggtac catgttcccc   2340
agtggtgact gtccaagtgc aatcgcctta cttgccatac aaatgctcct aggcctcatg   2400
ctagaggctt ttatcacagg tgcttttgtg gcgaagattg cccggccaaa aaatcgagct   2460
ttttcaattc gctttactga cacagcagta gtagctcaca tggatggcaa acctaatctt   2520
atcttccaag tggccaacac ccgacctagc cctctaacca gtgtccgggt ctcagctgta   2580
ctctatcagg aaagagaaaa tggcaaactc taccagacca gtgtggattt ccaccttgat   2640
ggcatcagtt ctgacgaatg tccattcttc atctttccac taacgtacta tcactccatt   2700
acaccatcaa gtcctctggc tactctgctc cagcatgaaa atccttctca ctttgaatta   2760
gttgtattcc tttcagcaat gcaggagggc actggagaaa tatgccaaag gaggacatcc   2820
tacctaccgt ctgaaatcat gttacatcac tgttttgcat ctctgttgac ccgaggttcc   2880
aaaggtgaat atcaaatcaa gatggagaat tttgacaaga ctgtccctga atttccaact   2940
cctctggttt ctaaaagccc aaacaggact gacctggata tccacatcaa tggacaaagc   3000
attgacaatt ttcagatctc tgaaacagga ctgacagaat aaggatcc                3048
```

-continued

<210> SEQ ID NO 6
<211> LENGTH: 2495
<212> TYPE: DNA
<213> ORGANISM: Artificial Sequence
<220> FEATURE:
<223> OTHER INFORMATION: synthetic

<400> SEQUENCE: 6
aattctgtca ttttactagg gtgatgaaat tcccaagcaa caccatcctt ttcagataag 60
ggcactgagg ctgagagagg agctgaaacc tacccggggt caccacacac aggtggcaag 120
gctgggacca gaaaccagga ctgttgactg cagcccggta ttcattcttt ccatagccca 180
cagggctgtc aaagacccca gggcctagtc agaggctcct ccttcctgga gagttcctgg 240
cacagaagtt gaagctcagc acagccccct aacccccaac tctctctgca aggcctcagg 300
ggtcagaaca ctggtggagc agatccttta gcctctggat tttagggcca tggtagaggg 360
ggtgttgccc taaattccag ccctggtctc agcccaacac cctccaagaa gaaattagag 420
gggccatggc caggctgtgc tagccgttgc ttctgagcag attacaagaa gggactaaga 480
caaggactcc tttgtggagg tcctggctta gggagtcaag tgacggcggc tcagcactca 540
cgtgggcagt gccagcctct aagagtgggc aggggcactg gccacagagt cccagggagt 600
cccaccagcc tagtcgccag gtcgaccaag tttgtacaaa aaagcaggct gccaccatgg 660
tgagcaaggg cgaggagctg ttcaccgggg tggtgcccat cctggtcgag ctggacggcg 720
acgtaaacgg ccacaagttc agcgtgtccg gcgagggcga gggcgatgcc acctacggca 780
agctgaccct gaagttcatc tgcaccaccg gcaagctgcc cgtgccctgg cccaccctcg 840
tgaccaccct gacctacggc gtgcagtgct tcagccgcta ccccgaccac atgaagcagc 900
acgacttctt caagtccgcc atgcccgaag gctacgtcca ggagcgcacc atcttcttca 960
aggacgacgg caactacaag acccgcgccg aggtgaagtt cgagggcgac accctggtga 1020
accgcatcga gctgaagggc atcgacttca aggaggacgg caacatcctg gggcacaagc 1080
tggagtacaa ctacaacagc cacaacgtct atatcatggc cgacaagcag aagaacggca 1140
tcaaggtgaa cttcaagatc cgccacaaca tcgaggacgg cagcgtgcag ctcgccgacc 1200
actaccagca gaacaccccc atcggcgacg gccccgtgct gctgcccgac aaccactacc 1260
tgagcaccca gtccgccctg agcaaagacc ccaacgagaa gcgcgatcac atggtcctgc 1320
tggagttcgt gaccgccgcc gggatcactc tcggcatgga cgagctgtac aagtccggac 1380
tcagatctcg agctcaagct tcgaattctg acagcagtaa ttgcaaagtt attgctcctc 1440
tcctaagtca aagataccgg aggatggtca ccaaggatgg ccacagcaca cttcaaatgg 1500
atggcgctca aagaggtctt gcatatcttc gagatgcttg gggaatccta atggacatgc 1560
gctggcgttg gatgatgttg gtcttttctg cttcttttgt tgtccactgg cttgtctttg 1620
cagtgctctg gtatgttctg gctgagatga atggtgatct ggaactagat catgatgccc 1680
cacctgaaaa ccacactatc tgtgtcaagt atatcaccag tttcacagct gcattctcct 1740
tctccctgga gacacaactc acaattggtt atggtaccat gttccccagt ggtgactgtc 1800
caagtgcaat cgccttactt gccatacaaa tgctcctagg cctcatgcta gaggctttta 1860
tcacaggtgc ttttgtggcg aagattgccc ggccaaaaaa tcgagctttt tcaattcgct 1920
ttactgacac agcagtagta gctcacatgg atggcaaacc taatcttatc ttccaagtgg 1980
ccaacacccg acctagccct ctaaccagtg tccgggtctc agctgtactc tatcaggaaa 2040
gagaaaatgg caaactctac cagaccagtg tggatttcca ccttgatggc atcagttctg 2100

-continued

```
acgaatgtcc attcttcatc tttccactaa cgtactatca ctccattaca ccatcaagtc   2160

ctctggctac tctgctccag catgaaaatc cttctcactt tgaattagtt gtattccttt   2220

cagcaatgca ggagggcact ggagaaatat gccaaaggag gacatcctac ctaccgtctg   2280

aaatcatgtt acatcactgt tttgcatctc tgttgacccg aggttccaaa ggtgaatatc   2340

aaatcaagat ggagaatttt gacaagactg tccctgaatt tccaactcct ctggtttcta   2400

aaagcccaaa caggactgac ctggatatcc acatcaatgg acaaagcatt gacaattttc   2460

agatctctga aacaggactg acagaataag gatcc                              2495
```

<210> SEQ ID NO 7
<211> LENGTH: 26
<212> TYPE: DNA
<213> ORGANISM: Artificial Sequence
<220> FEATURE:
<223> OTHER INFORMATION: synthetic

<400> SEQUENCE: 7

```
gcttcgaatt ccgacagcag taattg                                          26
```

<210> SEQ ID NO 8
<211> LENGTH: 26
<212> TYPE: DNA
<213> ORGANISM: Artificial Sequence
<220> FEATURE:
<223> OTHER INFORMATION: synthetic

<400> SEQUENCE: 8

```
atccggtgga tccttattct gtcagt                                          26
```

<210> SEQ ID NO 9
<211> LENGTH: 6752
<212> TYPE: DNA
<213> ORGANISM: Artificial Sequence
<220> FEATURE:
<223> OTHER INFORMATION: synthetic

<400> SEQUENCE: 9

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tatcgatcaa ctttgtatag aaaagttggg ctccggtgcc    180

cgtcagtggg cagagcgcac atcgcccaca gtccccgaga agttgggggg aggggtcggc    240

aattgaaccg gtgcctagag aaggtggcgc ggggtaaact gggaaagtga tgtcgtgtac    300

tggctccgcc tttttcccga gggtggggga gaaccgtata taagtgcagt agtcgccgtg    360

aacgttcttt ttcgcaacgg gtttgccgcc agaacacagg taagtgccgt gtgtggttcc    420

cgcgggcctg gcctctttac gggttatggc ccttgcgtgc cttgaattac ttccacctgg    480

ctgcagtacg tgattcttga tcccgagctt cgggttggaa gtgggtggga gagttcgagg    540

ccttgcgctt aaggagcccc ttcgcctcgt gcttgagttg aggcctggcc tgggcgctgg    600

ggccgccgcg tgcgaatctg gtggcacctt cgcgcctgtc tcgctgcttt cgataagtct    660

ctagccattt aaaatttttg atgacctgct gcgacgcttt ttttctggca agatagtctt    720

gtaaatgcgg gccaagatct gcacactggt atttcggttt ttggggccgc gggcggcgac    780

ggggcccgtg cgtcccagcg cacatgttcg gcgaggcggg gcctgcgagc gcggccaccg    840

agaatcggac gggggtagtc tcaagctggc cggcctgctc tggtgcctgg tctcgcgccg    900

ccgtgtatcg ccccgccctg ggcggcaagg ctggcccggt cggcaccagt tgcgtgagcg    960
```

-continued gaaagatggc cgcttcccgg ccctgctgca gggagctcaa aatggaggac gcggcgctcg 1020
ggagagcggg cgggtgagtc acccacacaa aggaaaaggg cctttccgtc ctcagccgtc 1080
gcttcatgtg actccacgga gtaccgggcg ccgtccaggc acctcgatta gttctcgagc 1140
ttttggagta cgtcgtcttt aggttggggg gaggggtttt atgcgatgga gtttccccac 1200
actgagtggg tggagactga agttaggcca gcttggcact tgatgtaatt ctccttggaa 1260
tttgcccttt ttgagtttgg atcttggttc attctcaagc ctcagacagt ggttcaaagt 1320
ttttttcttc catttcaggt gtcgtgacaa gtttgtacaa aaaagcaggc tgccaccatg 1380
gtgagcaagg gcgaggagct gttcaccggg gtggtgccca tcctggtcga gctggacggc 1440
gacgtaaacg gccacaagtt cagcgtgtcc ggcgagggcg agggcgatgc cacctacggc 1500
aagctgaccc tgaagttcat ctgcaccacc ggcaagctgc ccgtgccctg gcccaccctc 1560
gtgaccaccc tgacctacgg cgtgcagtgc ttcagccgct accccgacca catgaagcag 1620
cacgacttct tcaagtccgc catgcccgaa ggctacgtcc aggagcgcac catcttcttc 1680
aaggacgacg gcaactacaa gacccgcgcc gaggtgaagt tcgagggcga caccctggtg 1740
aaccgcatcg agctgaaggg catcgacttc aaggaggacg gcaacatcct ggggcacaag 1800
ctggagtaca actacaacag ccacaacgtc tatatcatgg ccgacaagca gaagaacggc 1860
atcaaggtga acttcaagat ccgccacaac atcgaggacg gcagcgtgca gctcgccgac 1920
cactaccagc agaacacccc catcggcgac ggccccgtgc tgctgcccga caaccactac 1980
ctgagcaccc agtccgccct gagcaaagac cccaacgaga agcgcgatca catggtcctg 2040
ctggagttcg tgaccgccgc cgggatcact ctcggcatgg acgagctgta caagtccgga 2100
ctcagatctc gagctcaagc ttcgaattct gacagcagta attgcaaagt tattgctcct 2160
ctcctaagtc aaagataccg gaggatggtc accaaggatg gccacagcac acttcaaatg 2220
gatggcgctc aaagaggtct tgcatatctt cgagatgctt ggggaatcct aatggacatg 2280
cgctggcgtt ggatgatgtt ggtcttttct gcttcttttg ttgtccactg gcttgtcttt 2340
gcagtgctct ggtatgttct ggctgagatg aatggtgatc tggaactaga tcatgatgcc 2400
ccacctgaaa accacactat ctgtgtcaag tatatcacca gtttcacagc tgcattctcc 2460
ttctccctgg agacacaact cacaattggt tatggtacca tgttccccag tggtgactgt 2520
ccaagtgcaa tcgccttact tgccatacaa atgctcctag gcctcatgct agaggctttt 2580
atcacaggtg cttttgtggc gaagattgcc cggccaaaaa atcgagcttt ttcaattcgc 2640
tttactgaca cagcagtagt agctcacatg gatggcaaac ctaatcttat cttccaagtg 2700
gccaacaccc gacctagccc tctaaccagt gtccgggtct cagctgtact ctatcaggaa 2760
agagaaaatg gcaaactcta ccagaccagt gtggatttcc accttgatgg catcagttct 2820
gacgaatgtc cattcttcat ctttccacta acgtactatc actccattac accatcaagt 2880
cctctggcta ctctgctcca gcatgaaaat ccttctcact ttgaattagt tgtattcctt 2940
tcagcaatgc aggagggcac tggagaaata tgccaaagga ggacatccta cctaccgtct 3000
gaaatcatgt tacatcactg ttttgcatct ctgttgaccc gaggttccaa aggtgaatat 3060
caaatcaaga tggagaattt tgacaagact gtccctgaat ttccaactcc tctggtttct 3120
aaaagcccaa acaggactga cctggatatc cacatcaatg gacaaagcat tgacaatttt 3180
cagatctctg aaacaggact gacagaataa ggatccaccc agctttcttg tacaaagtgg 3240
tgatggccgg ccgcttcgag cagacatgat aagatacatt gatgagtttg gacaaaccac 3300

-continued

```
aactagaatg cagtgaaaaa aatgctttat ttgtgaaatt tgtgatgcta ttgctttatt   3360
tgtaaccatt ataagctgca ataaacaagt taacaacaac aattgcattc attttatgtt   3420
tcaggttcag ggggaggtgt gggaggtttt ttaaagcaag taaaacctct acaaatgtgg   3480
taatcgatag atctaggaac ccctagtgat ggagttggcc actccctctc tgcgcgctcg   3540
ctcgctcact gaggccgggc gaccaaaggt cgcccgacgc ccgggctttg cccgggcggc   3600
ctcagtgagc gagcgagcgc gcagctgcct gcaggcagct tggcactggc cgtcgtttta   3660
caacgtcgtg actgggaaaa ccctggcgtt acccaactta atcgccttgc agcacatccc   3720
cctttcgcca gctggcgtaa tagcgaagag gcccgcaccg atcgcccttc ccaacagttg   3780
cgcagcctga atggcgaatg gcgcctgatg cggtattttc tccttacgca tctgtgcggt   3840
atttcacacc gcatacgtca aagcaaccat agtacgcgcc ctgtagcggc gcattaagcg   3900
cggcgggtgt ggtggttacg cgcagcgtga ccgctacact tgccagcgcc ctagcgcccg   3960
ctcctttcgc tttcttccct tcctttctcg ccacgttcgc cggctttccc cgtcaagctc   4020
taaatcgggg gctcccttta gggttccgat ttagtgcttt acggcacctc gaccccaaaa   4080
aacttgattt gggtgatggt tcacgtagtg ggccatcgcc ctgatagacg gtttttcgcc   4140
ctttgacgtt ggagtccacg ttctttaata gtggactctt gttccaaact ggaacaacac   4200
tcaaccctat ctcgggctat tcttttgatt tataagggat tttgccgatt tcggcctatt   4260
ggttaaaaaa tgagctgatt taacaaaaat ttaacgcgaa ttttaacaaa atattaacgt   4320
ttacaatttt atggtgcact ctcagtacaa tctgctctga tgccgcatag ttaagccagc   4380
cccgacaccc gccaacaccc gctgacgcgc cctgacgggc ttgtctgctc ccggcatccg   4440
cttacagaca agctgtgacc gtctccggga gctgcatgtg tcagaggttt tcaccgtcat   4500
caccgaaacg cgcgagacga aagggcctcg tgatacgcct atttttatag gttaatgtca   4560
tgataataat ggtttcttag acgtcaggtg gcacttttcg gggaaatgtg cgcggaaccc   4620
ctatttgttt atttttctaa atacattcaa atatgtatcc gctcatgaga caataaccct   4680
gataaatgct tcaataatat tgaaaaagga agagtatgag tattcaacat ttccgtgtcg   4740
cccttattcc cttttttgcg gcattttgcc ttcctgtttt tgctcaccca gaaacgctgg   4800
tgaaagtaaa agatgctgaa gatcagttgg gtgcacgagt gggttacatc gaactggatc   4860
tcaacagcgg taagatcctt gagagttttc gccccgaaga acgttttcca atgatgagca   4920
cttttaaagt tctgctatgt ggcgcggtat tatcccgtat tgacgccggg caagagcaac   4980
tcggtcgccg catacactat tctcagaatg acttggttga gtactcacca gtcacagaaa   5040
agcatcttac ggatggcatg acagtaagag aattatgcag tgctgccata accatgagtg   5100
ataacactgc ggccaactta cttctgacaa cgatcggagg accgaaggag ctaaccgctt   5160
ttttgcacaa catgggggat catgtaactc gccttgatcg ttgggaaccg gagctgaatg   5220
aagccatacc aaacgacgag cgtgacacca cgatgcctgt agcaatggca acaacgttgc   5280
gcaaactatt aactggcgaa ctacttactc tagcttcccg gcaacaatta atagactgga   5340
tggaggcgga taaagttgca ggaccacttc tgcgctcggc ccttccggct ggctggttta   5400
ttgctgataa atctggagcc ggtgagcgtg ggtctcgcgg tatcattgca gcactggggc   5460
cagatggtaa gccctcccgt atcgtagtta tctacacgac ggggagtcag gcaactatgg   5520
atgaacgaaa tagacagatc gctgagatag gtgcctcact gattaagcat tggtaactgt   5580
cagaccaagt ttactcatat atactttaga ttgatttaaa acttcatttt taatttaaaa   5640
ggatctaggt gaagatcctt tttgataatc tcatgaccaa aatcccttaa cgtgagtttt   5700
```

-continued cgttccactg agcgtcagac cccgtagaaa agatcaaagg atcttcttga gatccttttt 5760
ttctgcgcgt aatctgctgc ttgcaaacaa aaaaaccacc gctaccagcg gtggtttgtt 5820
tgccggatca agagctacca actctttttc cgaaggtaac tggcttcagc agagcgcaga 5880
taccaaatac tgttcttcta gtgtagccgt agttaggcca ccacttcaag aactctgtag 5940
caccgcctac atacctcgct ctgctaatcc tgttaccagt ggctgctgcc agtggcgata 6000
agtcgtgtct taccgggttg gactcaagac gatagttacc ggataaggcg cagcggtcgg 6060
gctgaacggg gggttcgtgc acacagccca gcttggagcg aacgacctac accgaactga 6120
gatacctaca gcgtgagcta tgagaaagcg ccacgcttcc cgaagggaga aaggcggaca 6180
ggtatccggt aagcggcagg gtcggaacag gagagcgcac gagggagctt ccagggggaa 6240
acgcctggta tctttatagt cctgtcgggt ttcgccacct ctgacttgag cgtcgatttt 6300
tgtgatgctc gtcagggggg cggagcctat ggaaaaacgc cagcaacgcg gcctttttac 6360
ggttcctggc cttttgctgg ccttttgctc acatgttctt tcctgcgtta tcccctgatt 6420
ctgtggataa ccgtattacc gcctttgagt gagctgatac cgctcgccgc agccgaacga 6480
ccgagcgcag cgagtcagtg agcgaggaag cggaagagcg cccaatacgc aaaccgcctc 6540
tccccgcgcg ttggccgatt cattaatgca gctggcacga caggtttccc gactggaaag 6600
cgggcagtga gcgcaacgca attaatgtga gttagctcac tcattaggca ccccaggctt 6660
tacactttat gcttccggct cgtatgttgt gtggaattgt gagcggataa caatttcaca 6720
caggaaacag ctatgaccat gattacgaat tg 6752

<210> SEQ ID NO 10
<211> LENGTH: 6752
<212> TYPE: DNA
<213> ORGANISM: Artificial Sequence
<220> FEATURE:
<223> OTHER INFORMATION: synthetic

<400> SEQUENCE: 10
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tatcgatcaa ctttgtatag aaaagttggg ctccggtgcc 180
cgtcagtggg cagagcgcac atcgcccaca gtccccgaga agttgggggg aggggtcggc 240
aattgaaccg gtgcctagag aaggtggcgc ggggtaaact gggaaagtga tgtcgtgtac 300
tggctccgcc tttttcccga gggtggggga gaaccgtata taagtgcagt agtcgccgtg 360
aacgttcttt ttcgcaacgg gtttgccgcc agaacacagg taagtgccgt gtgtggttcc 420
cgcgggcctg gcctctttac gggttatggc ccttgcgtgc cttgaattac ttccacctgg 480
ctgcagtacg tgattcttga tcccgagctt cgggttggaa gtgggtggga gagttcgagg 540
ccttgcgctt aaggagcccc ttcgcctcgt gcttgagttg aggcctggcc tgggcgctgg 600
ggccgccgcg tgcgaatctg gtggcacctt cgcgcctgtc tcgctgcttt cgataagtct 660
ctagccattt aaaatttttg atgacctgct gcgacgcttt ttttctggca agatagtctt 720
gtaaatgcgg gccaagatct gcacactggt atttcggttt ttggggccgc gggcggcgac 780
ggggcccgtg cgtcccagcg cacatgttcg gcgaggcggg gcctgcgagc gcggccaccg 840
agaatcggac gggggtagtc tcaagctggc cggcctgctc tggtgcctgg tctcgcgccg 900
ccgtgtatcg ccccgccctg ggcggcaagg ctggcccggt cggcaccagt tgcgtgagcg 960

-continued

```
gaaagatggc cgcttcccgg ccctgctgca gggagctcaa aatggaggac gcggcgctcg   1020
ggagagcggg cgggtgagtc acccacacaa aggaaaaggg cctttccgtc ctcagccgtc   1080
gcttcatgtg actccacgga gtaccgggcg ccgtccaggc acctcgatta gttctcgagc   1140
ttttggagta cgtcgtcttt aggttggggg gaggggtttt atgcgatgga gtttccccac   1200
actgagtggg tggagactga agttaggcca gcttggcact tgatgtaatt ctccttggaa   1260
tttgcccttt ttgagtttgg atcttggttc attctcaagc ctcagacagt ggttcaaagt   1320
tttttcttc catttcaggt gtcgtgacaa gtttgtacaa aaaagcaggc tgccaccatg   1380
gtgagcaagg gcgaggagct gttcaccggg gtggtgccca tcctggtcga gctggacggc   1440
gacgtaaacg gccacaagtt cagcgtgtcc ggcgagggcg agggcgatgc cacctacggc   1500
aagctgaccc tgaagttcat ctgcaccacc ggcaagctgc ccgtgccctg gcccaccctc   1560
gtgaccaccc tgacctacgg cgtgcagtgc ttcagccgct accccgacca catgaagcag   1620
cacgacttct tcaagtccgc catgcccgaa ggctacgtcc aggagcgcac catcttcttc   1680
aaggacgacg gcaactacaa gacccgcgcc gaggtgaagt tcgagggcga caccctggtg   1740
aaccgcatcg agctgaaggg catcgacttc aaggaggacg gcaacatcct ggggcacaag   1800
ctggagtaca actacaacag ccacaacgtc tatatcatgg ccgacaagca gaagaacggc   1860
atcaaggtga acttcaagat ccgccacaac atcgaggacg gcagcgtgca gctcgccgac   1920
cactaccagc agaacacccc catcggcgac ggccccgtgc tgctgcccga caaccactac   1980
ctgagcaccc agtccgccct gagcaaagac cccaacgaga agcgcgatca catggtcctg   2040
ctggagttcg tgaccgccgc cgggatcact ctcggcatgg acgagctgta caagtccgga   2100
ctcagatctc gagctcaagc ttcgaattct gacagcagta attgcaaagt tattgctcct   2160
ctcctaagtc aaagataccg gaggatggtc accaaggatg gccacagcac acttcaaatg   2220
gatggcgctc aaagaggtct tgcatatctt cgagatgctt ggggaatcct aatggacatg   2280
cgctggcgtt ggatgatgtt ggtcttttct gcttcttttg ttgtccactg gcttgtcttt   2340
gcagtgctct ggtatgttct ggctgagatg aatggtgatc tggaactaga tcatgatgcc   2400
ccacctgaaa accacactat ctgtgtcaag tatatcacca gtttcacagc tgcattctcc   2460
ttctccctgg agacacaact cacaattggt tatggtacca tgttccccag tggtgactgt   2520
ccaagtgcaa tcgccttact tgccatacaa atgctcctag gcctcatgct agaggctttt   2580
atcacaggtg cttttgtggc gaagattgcc cggccaaaaa atcgagcttt ttcaattcgc   2640
tttactgaca cagcagtagt agctcacatg gatggcaaac ctaatcttat cttccaagtg   2700
gccaacaccc gacctagccc tctaaccagt gtccgggtct cagctgtact ctatcaggaa   2760
agagaaaatg gcaaactcta ccagaccagt gtggatttcc accttgatgg catcagttct   2820
gacgaatgtc cattcttcat ctttccacta acgtactatc actccattac accatcaagt   2880
cctctggcta ctctgctcca gcatgaaaat ccttctcact ttgaattagt tgtattcctt   2940
tcagcaatgc aggagggcac tggagaaata tgccaaagga ggacatccta cctaccgtct   3000
gaaatcatgt tacatcactg ttttgcatct ctgttgaccc gaggttccaa aggtgaatat   3060
caaatcaaga tggagaattt tgacaagact gtccctgaat ttccaactcc tctggtttct   3120
aaaagcccaa acaggactga cctggatatc cacatcaatg gacaaagcat tgacaatttt   3180
cagatctctg aaacaggact gacagaataa ggatccaccc agctttcttg tacaaagtgg   3240
tgatggccgg ccgcttcgag cagacatgat aagatacatt gatgagtttg gacaaaccac   3300
aactagaatg cagtgaaaaa aatgctttat ttgtgaaatt tgtgatgcta ttgctttatt   3360
```

-continued

```
tgtaaccatt ataagctgca ataaacaagt taacaacaac aattgcattc attttatgtt   3420
tcaggttcag ggggaggtgt gggaggtttt ttaaagcaag taaaacctct acaaatgtgg   3480
taatcgatag atctaggaac ccctagtgat ggagttggcc actccctctc tgcgcgctcg   3540
ctcgctcact gaggccgggc gaccaaaggt cgcccgacgc ccgggctttg cccgggcggc   3600
ctcagtgagc gagcgagcgc gcagctgcct gcaggcagct tggcactggc cgtcgtttta   3660
caacgtcgtg actgggaaaa ccctggcgtt acccaactta atcgccttgc agcacatccc   3720
cctttcgcca gctggcgtaa tagcgaagag gcccgcaccg atcgcccttc ccaacagttg   3780
cgcagcctga atggcgaatg gcgcctgatg cggtattttc tccttacgca tctgtgcggt   3840
atttcacacc gcatacgtca aagcaaccat agtacgcgcc ctgtagcggc gcattaagcg   3900
cggcgggtgt ggtggttacg cgcagcgtga ccgctacact tgccagcgcc ctagcgcccg   3960
ctcctttcgc tttcttccct tcctttctcg ccacgttcgc cggctttccc cgtcaagctc   4020
taaatcgggg gctcccttta gggttccgat ttagtgcttt acggcacctc gaccccaaaa   4080
aacttgattt gggtgatggt tcacgtagtg ggccatcgcc ctgatagacg gtttttcgcc   4140
ctttgacgtt ggagtccacg ttctttaata gtggactctt gttccaaact ggaacaacac   4200
tcaaccctat ctcgggctat tcttttgatt tataagggat tttgccgatt tcggcctatt   4260
ggttaaaaaa tgagctgatt taacaaaaat ttaacgcgaa ttttaacaaa atattaacgt   4320
ttacaatttt atggtgcact ctcagtacaa tctgctctga tgccgcatag ttaagccagc   4380
cccgacaccc gccaacaccc gctgacgcgc cctgacgggc ttgtctgctc ccggcatccg   4440
cttacagaca agctgtgacc gtctccggga gctgcatgtg tcagaggttt tcaccgtcat   4500
caccgaaacg cgcgagacga aagggcctcg tgatacgcct atttttatag gttaatgtca   4560
tgataataat ggtttcttag acgtcaggtg gcacttttcg gggaaatgtg cgcggaaccc   4620
ctatttgttt atttttctaa atacattcaa atatgtatcc gctcatgaga caataaccct   4680
gataaatgct tcaataatat tgaaaaagga agagtatgag tattcaacat ttccgtgtcg   4740
cccttattcc cttttttgcg gcattttgcc ttcctgtttt tgctcaccca gaaacgctgg   4800
tgaaagtaaa agatgctgaa gatcagttgg gtgcacgagt gggttacatc gaactggatc   4860
tcaacagcgg taagatcctt gagagttttc gccccgaaga acgttttcca atgatgagca   4920
cttttaaagt tctgctatgt ggcgcggtat tatcccgtat tgacgccggg caagagcaac   4980
tcggtcgccg catacactat tctcagaatg acttggttga gtactcacca gtcacagaaa   5040
agcatcttac ggatggcatg acagtaagag aattatgcag tgctgccata accatgagtg   5100
ataacactgc ggccaactta cttctgacaa cgatcggagg accgaaggag ctaaccgctt   5160
ttttgcacaa catgggggat catgtaactc gccttgatcg ttgggaaccg gagctgaatg   5220
aagccatacc aaacgacgag cgtgacacca cgatgcctgt agcaatggca acaacgttgc   5280
gcaaactatt aactggcgaa ctacttactc tagcttcccg gcaacaatta atagactgga   5340
tggaggcgga taaagttgca ggaccacttc tgcgctcggc ccttccggct ggctggttta   5400
ttgctgataa atctggagcc ggtgagcgtg ggtctcgcgg tatcattgca gcactggggc   5460
cagatggtaa gccctcccgt atcgtagtta tctacacgac ggggagtcag gcaactatgg   5520
atgaacgaaa tagacagatc gctgagatag gtgcctcact gattaagcat tggtaactgt   5580
cagaccaagt ttactcatat atactttaga ttgatttaaa acttcatttt taatttaaaa   5640
ggatctaggt gaagatcctt tttgataatc tcatgaccaa aatcccttaa cgtgagtttt   5700
```

-continued

```
cgttccactg agcgtcagac cccgtagaaa agatcaaagg atcttcttga gatccttttt   5760

ttctgcgcgt aatctgctgc ttgcaaacaa aaaaaccacc gctaccagcg gtggtttgtt   5820

tgccggatca agagctacca actctttttc cgaaggtaac tggcttcagc agagcgcaga   5880

taccaaatac tgttcttcta gtgtagccgt agttaggcca ccacttcaag aactctgtag   5940

caccgcctac atacctcgct ctgctaatcc tgttaccagt ggctgctgcc agtggcgata   6000

agtcgtgtct taccgggttg gactcaagac gatagttacc ggataaggcg cagcggtcgg   6060

gctgaacggg gggttcgtgc acacagccca gcttggagcg aacgacctac accgaactga   6120

gatacctaca gcgtgagcta tgagaaagcg ccacgcttcc cgaagggaga aaggcggaca   6180

ggtatccggt aagcggcagg gtcggaacag gagagcgcac gagggagctt ccagggggaa   6240

acgcctggta tctttatagt cctgtcgggt ttcgccacct ctgacttgag cgtcgatttt   6300

tgtgatgctc gtcagggggg cggagcctat ggaaaaacgc cagcaacgcg gcctttttac   6360

ggttcctggc cttttgctgg ccttttgctc acatgttctt tcctgcgtta tcccctgatt   6420

ctgtggataa ccgtattacc gcctttgagt gagctgatac cgctcgccgc agccgaacga   6480

ccgagcgcag cgagtcagtg agcgaggaag cggaagagcg cccaatacgc aaaccgcctc   6540

tccccgcgcg ttggccgatt cattaatgca gctggcacga caggtttccc gactggaaag   6600

cgggcagtga gcgcaacgca attaatgtga gttagctcac tcattaggca ccccaggctt   6660

tacactttat gcttccggct cgtatgttgt gtggaattgt gagcggataa caatttcaca   6720

caggaaacag ctatgaccat gattacgaat tg                                 6752


<210> SEQ ID NO 11
<211> LENGTH: 31
<212> TYPE: DNA
<213> ORGANISM: Artificial Sequence
<220> FEATURE:
<223> OTHER INFORMATION: synthetic

<400> SEQUENCE: 11

ccgctcgagt accttccaag tgctgtcaaa c                                    31


<210> SEQ ID NO 12
<211> LENGTH: 30
<212> TYPE: DNA
<213> ORGANISM: Artificial Sequence
<220> FEATURE:
<223> OTHER INFORMATION: synthetic

<400> SEQUENCE: 12

cgacgcgtca tgctgaattc cttaatttgc                                      30


<210> SEQ ID NO 13
<211> LENGTH: 30
<212> TYPE: DNA
<213> ORGANISM: Artificial Sequence
<220> FEATURE:
<223> OTHER INFORMATION: synthetic

<400> SEQUENCE: 13

ctagctagct cctcccagcg taacgtgagc                                      30


<210> SEQ ID NO 14
<211> LENGTH: 28
<212> TYPE: DNA
<213> ORGANISM: Artificial Sequence
<220> FEATURE:
<223> OTHER INFORMATION: synthetic
```

<400> SEQUENCE: 14
gaagatctct agtggcagcc ccatggtg 28

<210> SEQ ID NO 15
<211> LENGTH: 32
<212> TYPE: DNA
<213> ORGANISM: Artificial Sequence
<220> FEATURE:
<223> OTHER INFORMATION: synthetic

<400> SEQUENCE: 15
ctagctagcc tgtcctctta ggcagataca ga 32

<210> SEQ ID NO 16
<211> LENGTH: 30
<212> TYPE: DNA
<213> ORGANISM: Artificial Sequence
<220> FEATURE:
<223> OTHER INFORMATION: synthetic

<400> SEQUENCE: 16
gaagatctag agccttcatg ttgactgcta 30

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
gaaagttggg gatgaggcga 20

<210> SEQ ID NO 18
<211> LENGTH: 33
<212> TYPE: DNA
<213> ORGANISM: Artificial Sequence
<220> FEATURE:
<223> OTHER INFORMATION: synthetic

<400> SEQUENCE: 18
caatcaaagc ttcctcagag ctgccgggcg gct 33

<210> SEQ ID NO 19
<211> LENGTH: 21
<212> TYPE: DNA
<213> ORGANISM: Artificial Sequence
<220> FEATURE:
<223> OTHER INFORMATION: synthetic

<400> SEQUENCE: 19
gacatgcgct ggcgttggat g 21

<210> SEQ ID NO 20
<211> LENGTH: 21
<212> TYPE: DNA
<213> ORGANISM: Artificial Sequence
<220> FEATURE:
<223> OTHER INFORMATION: synthetic

<400> SEQUENCE: 20
gacatgcgct agcgttggat g 21